(12) United States Patent
Romanov et al.

(10) Patent No.: US 7,700,284 B2
(45) Date of Patent: Apr. 20, 2010

(54) REPORTER TRANSCRIPTION UNIT POPULATIONS AND KITS COMPRISING SAME

(75) Inventors: Sergei R. Romanov, Chapel Hill, NC (US); Alex Medvedev, Durham, NC (US); Sergei S. Makarov, Chapel Hill, NC (US)

(73) Assignee: Attagene, Inc., Morrisville, NC (US)

( * ) Notice: Subject to any disclaimer, the term of this patent is extended or adjusted under 35 U.S.C. 154(b) by 255 days.

(21) Appl. No.: 11/271,190

(22) Filed: Nov. 10, 2005

(65) Prior Publication Data

US 2006/0160108 A1 Jul. 20, 2006

Related U.S. Application Data

(60) Provisional application No. 60/626,663, filed on Nov. 10, 2004.

(51) Int. Cl.
| | |
|---|---|
| C12Q 1/68 | (2006.01) |
| C12N 15/63 | (2006.01) |
| C12N 15/85 | (2006.01) |
| C12N 5/14 | (2006.01) |
| C12N 15/11 | (2006.01) |
| C07H 21/04 | (2006.01) |

(52) U.S. Cl. .................. 435/6; 435/320.1; 435/325; 435/419; 536/23.1; 536/24.1

(58) Field of Classification Search .............. None
See application file for complete search history.

(56) References Cited

U.S. PATENT DOCUMENTS

| | | | |
|---|---|---|---|
| 6,924,113 B2 | 8/2005 | Li | |
| 2003/0028910 A1 * | 2/2003 | Giguere et al. | 800/18 |
| 2003/0143547 A1 | 7/2003 | Li et al. | |
| 2003/0148287 A1 | 8/2003 | Li et al. | |
| 2004/0214166 A1 | 10/2004 | Li | |

OTHER PUBLICATIONS

International Search Report from PCT/US05/41111, Apr. 5, 2007, Attagene, Inc.
Baldwin et al., 2001 "Control of Oncogenesis and Cancer Therapy Resistance by the Transcription Factor NF-KappaB", *J. Clin Invest*, 107:241-246.
Jeyaseelan et al., 2001 "Real-Time Detection of Gene Promoter Activity: Quantitation of Toxin Gene Transcription," *Nucleic Acids Research*, 29(12): e58 pp. 1-5.
Makarov et al., 2000 "NF-kappaB as a Therapeutic Target in Chronic Inflammation: Recent Advances," *Mol. Med Today*, 6:441-448.
Romanov et al., 2008, "Homogeneous Reporter System Enables Quantitative Functional Assessment of Multiple Transcription Factors," Nature Methods, vol. 5(3):253-260.

* cited by examiner

*Primary Examiner*—Shubo (Joe) Zhou
(74) *Attorney, Agent, or Firm*—Jones Day

(57) ABSTRACT

Compositions, methods and kits are provided that are useful, for example, for determining activities of multiple cis-regulatory sequences, such as promoters and enhancers, and/or multiple trans-acting factors, such as transcription factors, in a cell. In particular, in certain embodiments, compositions are provided comprising a population of polynucleotide reporter transcription units (RTUs) in which each RTU comprises a reporter sequence, a processing tag located in the reporter sequence; and a cis-regulatory element operably linked to the reporter sequence, wherein the reporter sequences between any two RTUs in the population, outside of the processing tags, are substantially identical and wherein the positions of the processing tags within the reporter sequences distinguish between any two RTUs differing, for example, in their cis-regulatory elements. The compositions, methods and kits can further be used, for example, to identify a cell type or disease state, for example, in a biological organism.

36 Claims, 35 Drawing Sheets

Figure 1:
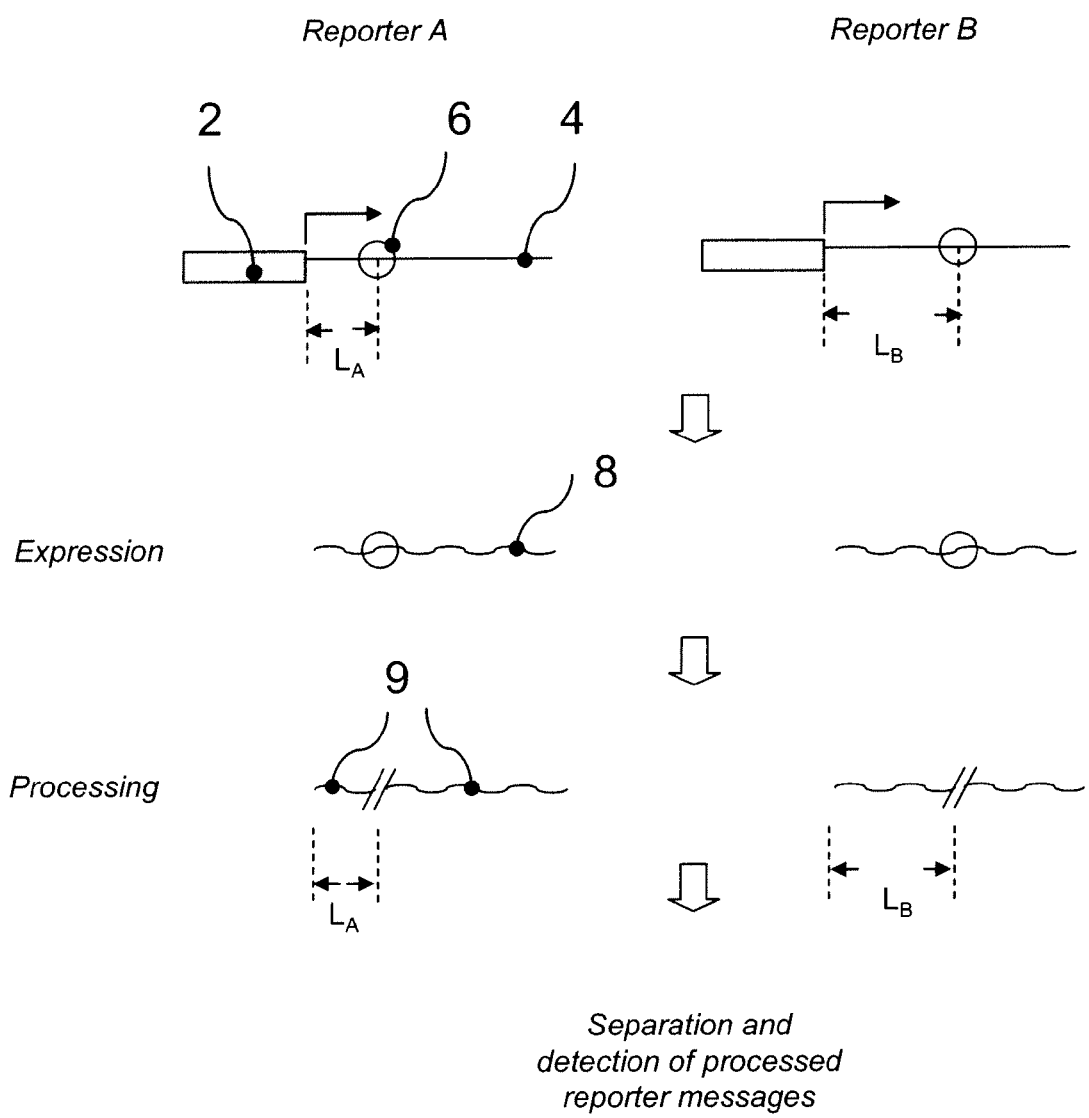

Separation and detection of processed reporter messages

Figure 11A

SEQ ID NO:13 (parental SEAP):
AAATACGAGATCCACCGAGACTCCACACTGGACCCCTCCCTGATGGAGATGACAGAGGC
TGCCCTGCGCCTGCTGAGCAGGAACCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCCTGCGAGGGAGCTCC
ATCTTCGGGCTGGCCCTGGCAAGGCCCGGGACAGGAAGGCCTACACGGTCCTCCTATA
CGGAAACGGTCCAGGCTATGTGCTCAAGGACGGCGCCCGGCCGGATGTTACCGAGAGCG
AGAGCGGGAGCCCCGAGTATCGGCAGCAGTCAGCAGTGCCCCTGGACGAAGAGACCCAC
GCAGGCGAGGACGTGGCGGTGTTCGCGCGCGGCCCGCAGGCGCACCTGGTTCACGGCGT
GCAGGAGCAGACCTTCATAGCGCACGTCATGGCCTTCGCCGCCTGCCTGGAGCCCTACAC
CGCCTGCGACCTGGCGCCCCCGCCGGCACCACCGACGCCGCGCACCCGGGTTACTCTAG
ATAGATTGTATCGGCGCTGTTCCTGC

SEQ ID NO:14 (Hpa22):
AAATACGAGATCCACCGAGACTCCACACTGGACCCCTCCCTGATGGAGATGACAGAGGC
TGCCCTGCGCCTGCTGAGCAGGAACCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCCTGCGAGGGAGCTCC
ATCTTCGGGCTGGCCCTGGCAAGGCCCGGGACAGGAAGGCCTACACGGTCCTCCTATA
CGGAAACGGTCCAGGCTATGTGCTCAAGGACGGCGCCCGGCCGGATGTTACCGAGAGCG
AGAGCGGGAGCCCCGAGTATCGGCAGCAGTCAGCAGTGCCCCTGGACGAAGAGACCCAC
GCAGGCGAGGACGTGGCGGTGTTCGCGCGCGGCCCGCAGGCGCACCTGGTTCACGGCGT
GCAGGAGCAGACCTTCATAGCGCACGTCATGGCCTTCGCCGCCTGCCTGTTAACGAGCC
CTACACCGCCTGCGACCTGGCGCCCCCGCCGGCACCACCGACGCCGCGCACCCGGGTT
ACTCTAGATAGATTGTATCGGCGCTGTTCCTGC

SEQ ID NO:15 (Hpa23):
AAATACGAGATCCACCGAGACTCCACACTGGACCCCTCCCTGATGGAGATGACAGAGGC
TGCCCTGCGCCTGCTGAGCAGGAACCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCCTGCGAGGGAGCTCC
ATCTTCGGGCTGGCCCCTGGCAAGGCCCGGGACAGGAAGGCCTACACGGTCCTCCTATA
CGGAAACGGTCCAGGCTATGTGCTCAAGGACGGCGCCCGGCCGGATGTTACCGAGAGCG
AGAGCGGGAGCCCCGAGTATCGGCAGCAGTCAGCAGTGCCCCTGGACGAAGAGACCCAC
GCAGGCGAGGACGTGGCGGTGTTCGCGCGCGGCCCGCAGGCGCACCTGGTTCACGGCGT
GCAGGAGCAGACCTTCATAGCGCACGTCATGGCCTTCGTTAACCGCCTGCCTGGAGCCC
TACACCGCCTGCGACCTGGCGCCCCCGCCGGCACCACCGACGCCGCGCACCCGGGTTA
CTCTAGATAGATTGTATCGGCGCTGTTCCTGC

Figure 11B

SEQ ID NO:16 (Hpa6):
AAATACGAGATCCACCGAGACTCCACACTGGACCCCTCCCTGATGGAGATGACAGAGGC
TGCCCTGCGCCTGCTGAGCAGGAACCCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCTGCGAGGGAGCTCC
ATCTTCGGGCTGGCCCCTGGCAAGGCCCGGGACAGGAAGGCCTACACGGTCCTCCTATA
CGGAAACGGTCCAGGCTATGTGCTCAAGGACGGCGCCCGGCCGGATGTTACCGAGAGCG
AGAGCGGGAGCCCCGAGTATCGGCAGCAGTCAGCAGTGCCCCTGGACGAAGAGACCCAC
GCAGGCGAGGACGTGGCGGTGTTCGCGCGCGGCCCGCAGGCGCACCTGGTTCACGGCGT
GCAGGAGCAGACCTTCATAGCGCACGTTAACGCCTTCGCCGCCTGCCTGGAGCCCTACA
CCGCCTGCGACCTGGCGCCCCCGCCGGCACCACCGACGCCGCGCACCCGGGTTACTCTA
GATAGATTGTATCGGCGCTGTTCCTGC

SEQ ID NO:17 (Hpa33):
AAATACGAGATCCACCGAGACTCCACACTGGACCCCTCCCTGATGGAGATGACAGAGGC
TGCCCTGCGCCTGCTGAGCAGGAACCCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCTGCGAGGGAGCTCC
ATCTTCGGGCTGGCCCCTGGCAAGGCCCGGGACAGGAAGGCCTACACGGTCCTCCTATA
CGGAAACGGTCCAGGCTATGTGCTCAAGGACGGCGCCCGGCCGGATGTTACCGAGAGCG
AGAGCGGGAGCCCCGAGTATCGGCAGCAGTCAGCAGTGCCCCTGGACGAAGAGACCCAC
GCAGGCGAGGACGTGGCGGTGTTCGCGCGCGGCCCGCAGGCGCACCTGGTTCACGGCGT
GCAGGAGCAGACCTTCATAGCGTTAACACGTCATGGCCTTCGCCGCCTGCCTGGAGCCC
TACACCGCCTGCGACCTGGCGCCCCCGCCGGCACCACCGACGCCGCGCACCCGGGTTA
CTCTAGATAGATTGTATCGGCGCTGTTCCTGC

SEQ ID NO:18 (Hpa20):
AAATACGAGATCCACCGAGACTCCACACTGGACCCCTCCCTGATGGAGATGACAGAGGC
TGCCCTGCGCCTGCTGAGCAGGAACCCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCTGCGAGGGAGCTCC
ATCTTCGGGCTGGCCCCTGGCAAGGCCCGGGACAGGAAGGCCTACACGGTCCTCCTATA
CGGAAACGGTCCAGGCTATGTGCTCAAGGACGGCGCCCGGCCGGATGTTACCGAGAGCG
AGAGCGGGAGCCCCGAGTATCGGCAGCAGTCAGCAGTGCCCCTGGACGAAGAGACCCAC
GCAGGCGAGGACGTGGCGGTGTTCGCGCGCGGCCCGCAGGCGCACCTGGTTCACGGCGT
GCAGGAGCAGACCGTTAACATAGCGCACGTCATGGCCTTCGCCGCCTGCCTGGAGCCCT
ACACCGCCTGCGACCTGGCGCCCCCGCCGGCACCACCGACGCCGCGCACCCGGGTTAC
TCTAGATAGATTGTATCGGCGCTGTTCCTGC

Figure 11C

SEQ ID NO:19 (Hpa8):
AAATACGAGATCCACCGAGACTCCACACTGGACCCCTCCCTGATGGAGATGACAGAGGC
TGCCCTGCGCCTGCTGAGCAGGAACCCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCTGCGAGGGAGCTCC
ATCTTCGGGCTGGCCCCTGGCAAGGCCCGGGACAGGAAGGCCTACACGGTCCTCCTATA
CGGAAACGGTCCAGGCTATGTGCTCAAGGACGGCGCCCGGCCGGATGTTACCGAGAGCG
AGAGCGGGAGCCCCGAGTATCGGCAGCAGTCAGCAGTGCCCCTGGACGAAGAGACCCAC
GCAGGCGAGGACGTGGCGGTGTTCGCGCGCGGCCCGCAGGCGCACCTGGTTCACGGCGT
GCAGTTAACGAGCAGACCTTCATAGCGCACGTCATGGCCTTCGCCGCCTGCCTGGAGCC
CTACACCGCCTGCGACCTGGCGCCCCCGCCGGCACCACCGACGCCGCGCACCCGGGTT
ACTCTAGATAGATTGTATCGGCGCTGTTCCTGC

SEQ ID NO:20 (Hpa4):
AAATACGAGATCCACCGAGACTCCACACTGGACCCCTCCCTGATGGAGATGACAGAGGC
TGCCCTGCGCCTGCTGAGCAGGAACCCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCTGCGAGGGAGCTCC
ATCTTCGGGCTGGCCCCTGGCAAGGCCCGGGACAGGAAGGCCTACACGGTCCTCCTATA
CGGAAACGGTCCAGGCTATGTGCTCAAGGACGGCGCCCGGCCGGATGTTACCGAGAGCG
AGAGCGGGAGCCCCGAGTATCGGCAGCAGTCAGCAGTGCCCCTGGACGAAGAGACCCAC
GCAGGCGAGGACGTGGCGGTGTTCGCGCGCGGCCCGCAGGCGCACCTGGTTAACGGCGT
GCAGGAGCAGACCTTCATAGCGCACGTCATGGCCTTCGCCGCCTGCCTGGAGCCCTACAC
CGCCTGCGACCTGGCGCCCCCGCCGGCACCACCGACGCCGCGCACCCGGGTTACTCTAG
ATAGATTGTATCGGCGCTGTTCCTGC

SEQ ID NO:21 (Hpa34):
AAATACGAGATCCACCGAGACTCCACACTGGACCCCTCCCTGATGGAGATGACAGAGGC
TGCCCTGCGCCTGCTGAGCAGGAACCCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCTGCGAGGGAGCTCC
ATCTTCGGGCTGGCCCCTGGCAAGGCCCGGGACAGGAAGGCCTACACGGTCCTCCTATA
CGGAAACGGTCCAGGCTATGTGCTCAAGGACGGCGCCCGGCCGGATGTTACCGAGAGCG
AGAGCGGGAGCCCCGAGTATCGGCAGCAGTCAGCAGTGCCCCTGGACGAAGAGACCCAC
GCAGGCGAGGACGTGGCGGTGTTCGCGCGCGGCCCGCAGGCGTTAACCTGGTTCACGGC
GTGCAGGAGCAGACCTTCATAGCGCACGTCATGGCCTTCGCCGCCTGCCTGGAGCCCTAC
ACCGCCTGCGACCTGGCGCCCCCGCCGGCACCACCGACGCCGCGCACCCGGGTTACTCT
AGATAGATTGTATCGGCGCTGTTCCTGC

Figure 11D

SEQ ID NO:22 (Hpa9):
AAATACGAGATCCACCGAGACTCCACACTGGACCCCTCCCTGATGGAGATGACAGAGGC
TGCCCTGCGCCTGCTGAGCAGGAACCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCCTGCGAGGGAGCTCC
ATCTTCGGGCTGGCCCCTGGCAAGGCCCGGGACAGGAAGGCCTACACGGTCCTCCTATA
CGGAAACGGTCCAGGCTATGTGCTCAAGGACGGCGCCCGGCCGGATGTTACCGAGAGCG
AGAGCGGGAGCCCCGAGTATCGGCAGCAGTCAGCAGTGCCCCTGGACGAAGAGACCCAC
GCAGGCGAGGACGTGGCGGTGTTCGCGCGCGGCCCGTTAACAGGCGCACCTGGTTCACG
GCGTGCAGGAGCAGACCTTCATAGCGCACGTCATGGCCTTCGCCGCCTGCCTGGAGCCCT
ACACCGCCTGCGACCTGGCGCCCCCGCCGGCACCACCGACGCCGCGCACCCGGGTTAC
TCTAGATAGATTGTATCGGCGCTGTTCCTGC

SEQ ID NO:23 (Hpa28):
AAATACGAGATCCACCGAGACTCCACACTGGACCCCTCCCTGATGGAGATGACAGAGGC
TGCCCTGCGCCTGCTGAGCAGGAACCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCCTGCGAGGGAGCTCC
ATCTTCGGGCTGGCCCCTGGCAAGGCCCGGGACAGGAAGGCCTACACGGTCCTCCTATA
CGGAAACGGTCCAGGCTATGTGCTCAAGGACGGCGCCCGGCCGGATGTTACCGAGAGCG
AGAGCGGGAGCCCCGAGTATCGGCAGCAGTCAGCAGTGCCCCTGGACGAAGAGACCCAC
GCAGGCGAGGACGTGGCGGTGTTCGCGCGTTAACGGCCCGCAGGCGCACCTGGTTCACG
GCGTGCAGGAGCAGACCTTCATAGCGCACGTCATGGCCTTCGCCGCCTGCCTGGAGCCCT
ACACCGCCTGCGACCTGGCGCCCCCGCCGGCACCACCGACGCCGCGCACCCGGGTTAC
TCTAGATAGATTGTATCGGCGCTGTTCCTGC

SEQ ID NO:24 (Hpa5):
AAATACGAGATCCACCGAGACTCCACACTGGACCCCTCCCTGATGGAGATGACAGAGGC
TGCCCTGCGCCTGCTGAGCAGGAACCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCCTGCGAGGGAGCTCC
ATCTTCGGGCTGGCCCCTGGCAAGGCCCGGGACAGGAAGGCCTACACGGTCCTCCTATA
CGGAAACGGTCCAGGCTATGTGCTCAAGGACGGCGCCCGGCCGGATGTTACCGAGAGCG
AGAGCGGGAGCCCCGAGTATCGGCAGCAGTCAGCAGTGCCCCTGGACGAAGAGACCCAC
GCAGGCGAGGACGTGGCGGTGTTAACGCGCGCGGCCCGCAGGCGCACCTGGTTCACGGC
GTGCAGGAGCAGACCTTCATAGCGCACGTCATGGCCTTCGCCGCCTGCCTGGAGCCCTAC
ACCGCCTGCGACCTGGCGCCCCCGCCGGCACCACCGACGCCGCGCACCCGGGTTACTCT
AGATAGATTGTATCGGCGCTGTTCCTGC

Figure 11E

SEQ ID NO:25 (Hpa21):
AAATACGAGATCCACCGAGACTCCACACTGGACCCCTCCCTGATGGAGATGACAGAGGC
TGCCCTGCGCCTGCTGAGCAGGAACCCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCCTGCGAGGGAGCTCC
ATCTTCGGGCTGGCCCCTGGCAAGGCCCGGGACAGGAAGGCCTACACGGTCCTCCTATA
CGGAAACGGTCCAGGCTATGTGCTCAAGGACGGCGCCCGGCCGGATGTTACCGAGAGCG
AGAGCGGGAGCCCCGAGTATCGGCAGCAGTCAGCAGTGCCCCTGGACGAAGAGACCCAC
GCAGGCGAGGACGTTAACGGCGGTGTTCGCGCGCGGCCCGCAGGCGCACCTGGTTCACG
GCGTGCAGGAGCAGACCTTCATAGCGCACGTCATGGCCTTCGCCGCCTGCCTGGAGCCCT
ACACCGCCTGCGACCTGGCGCCCCCGCCGGCACCACCGACGCCGCGCACCCGGGTTAC
TCTAGATAGATTGTATCGGCGCTGTTCCTGC

SEQ ID NO:26 (Hpa27):
AAATACGAGATCCACCGAGACTCCACACTGGACCCCTCCCTGATGGAGATGACAGAGGC
TGCCCTGCGCCTGCTGAGCAGGAACCCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCCTGCGAGGGAGCTCC
ATCTTCGGGCTGGCCCCTGGCAAGGCCCGGGACAGGAAGGCCTACACGGTCCTCCTATA
CGGAAACGGTCCAGGCTATGTGCTCAAGGACGGCGCCCGGCCGGATGTTACCGAGAGCG
AGAGCGGGAGCCCCGAGTATCGGCAGCAGTCAGCAGTGCCCCTGGACGAAGAGACCCAC
GCAGGTTAACGAGGACGTGGCGGTGTTCGCGCGCGGCCCGCAGGCGCACCTGGTTCACG
GCGTGCAGGAGCAGACCTTCATAGCGCACGTCATGGCCTTCGCCGCCTGCCTGGAGCCCT
ACACCGCCTGCGACCTGGCGCCCCCGCCGGCACCACCGACGCCGCGCACCCGGGTTAC
TCTAGATAGATTGTATCGGCGCTGTTCCTGC

SEQ ID NO:27 (Hpa11):
AAATACGAGATCCACCGAGACTCCACACTGGACCCCTCCCTGATGGAGATGACAGAGGC
TGCCCTGCGCCTGCTGAGCAGGAACCCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCCTGCGAGGGAGCTCC
ATCTTCGGGCTGGCCCCTGGCAAGGCCCGGGACAGGAAGGCCTACACGGTCCTCCTATA
CGGAAACGGTCCAGGCTATGTGCTCAAGGACGGCGCCCGGCCGGATGTTACCGAGAGCG
AGAGCGGGAGCCCCGAGTATCGGCAGCAGTCAGCAGTGCCCCTGGACGAAGAGACCCA
GTTAACCGCAGGCGAGGACGTGGCGGTGTTCGCGCGCGGCCCGCAGGCGCACCTGGTTC
ACGGCGTGCAGGAGCAGACCTTCATAGCGCACGTCATGGCCTTCGCCGCCTGCCTGGAG
CCCTACACCGCCTGCGACCTGGCGCCCCCGCCGGCACCACCGACGCCGCGCACCCGGG
TTACTCTAGATAGATTGTATCGGCGCTGTTCCTGC

Figure 11F

SEQ ID NO:28 (Hpa10):
AAATACGAGATCCACCGAGACTCCACACTGGACCCCTCCCTGATGGAGATGACAGAGGC
TGCCCTGCGCCTGCTGAGCAGGAACCCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCCTGCGAGGGAGCTCC
ATCTTCGGGCTGGCCCCTGGCAAGGCCCGGGACAGGAAGGCCTACACGGTCCTCCTATA
CGGAAACGGTCCAGGCTATGTGCTCAAGGACGGCGCCCGGCCGGATGTTACCGAGAGCG
AGAGCGGGAGCCCCGAGTATCGGCAGCAGTCAGCAGTGCCCTGTTAACGACGAAGAG
ACCCACGCAGGCGAGGACGTGGCGGTGTTCGCGCGCGGCCCGCAGGCGCACCTGGTTCA
CGGCGTGCAGGAGCAGACCTTCATAGCGCACGTCATGGCCTTCGCCGCCTGCCTGGAGCC
CTACACCGCCTGCGACCTGGCGCCCCCGCCGGCACCACCGACGCCGCGCACCCGGGTT
ACTCTAGATAGATTGTATCGGCGCTGTTCCTGC

SEQ ID NO:29 (Hpa2):
AAATACGAGATCCACCGAGACTCCACACTGGACCCCTCCCTGATGGAGATGACAGAGGC
TGCCCTGCGCCTGCTGAGCAGGAACCCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCCTGCGAGGGAGCTCC
ATCTTCGGGCTGGCCCCTGGCAAGGCCCGGGACAGGAAGGCCTACACGGTCCTCCTATA
CGGAAACGGTCCAGGCTATGTGCTCAAGGACGGCGCCCGGCCGGATGTTACCGAGAGCG
AGAGCGGGAGCCCCGAGTATCGGCAGCAGTTAACAGTGCCCCTGGACGAAGAGACCCA
CGCAGGCGAGGACGTGGCGGTGTTCGCGCGCGGCCCGCAGGCGCACCTGGTTCACGGCG
TGCAGGAGCAGACCTTCATAGCGCACGTCATGGCCTTCGCCGCCTGCCTGGAGCCCTACA
CCGCCTGCGACCTGGCGCCCCCGCCGGCACCACCGACGCCGCGCACCCGGGTTACTCTA
GATAGATTGTATCGGCGCTGTTCCTGC

SEQ ID NO:30 (Hpa24):
AAATACGAGATCCACCGAGACTCCACACTGGACCCCTCCCTGATGGAGATGACAGAGGC
TGCCCTGCGCCTGCTGAGCAGGAACCCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCCTGCGAGGGAGCTCC
ATCTTCGGGCTGGCCCCTGGCAAGGCCCGGGACAGGAAGGCCTACACGGTCCTCCTATA
CGGAAACGGTCCAGGCTATGTGCTCAAGGACGGCGCCCGGCCGGATGTTACCGAGAGCG
AGAGCGGGAGCCCCGAGTATCGGTTAACAGCAGTCAGCAGTGCCCTGGACGAAGAGA
CCCACGCAGGCGAGGACGTGGCGGTGTTCGCGCGCGGCCCGCAGGCGCACCTGGTTCAC
GGCGTGCAGGAGCAGACCTTCATAGCGCACGTCATGGCCTTCGCCGCCTGCCTGGAGCCC
TACACCGCCTGCGACCTGGCGCCCCCGCCGGCACCACCGACGCCGCGCACCCGGGTTA
CTCTAGATAGATTGTATCGGCGCTGTTCCTGC

Figure 11G

SEQ ID NO:31 (Hpa29):
AAATACGAGATCCACCGAGACTCCACACTGGACCCCTCCCTGATGGAGATGACAGAGGC
TGCCCTGCGCCTGCTGAGCAGGAACCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCACGTCTTCTCCTTCGGAGGCTACCCCTGCGAGGGAGCTCC
ATCTTCGGGCTGGCCCCTGGCAAGGCCCGGGACAGGAAGGCCTACACGGTCCTCCTATA
CGGAAACGGTCCAGGCTATGTGCTCAAGGACGGCGCCCGGCCGGATGTTACCGAGAGCG
AGAGCGGGAGCCCCGTTAACGTATCGGCAGCAGTCAGCAGTGCCCTGGACGAAGAGA
CCCACGCAGGCGAGGACGTGGCGGTGTTCGCGCGCGGCCCGCAGGCGCACCTGGTTCAC
GGCGTGCAGGAGCAGACCTTCATAGCGCACGTCATGGCCTTCGCCGCCTGCCTGGAGCCC
TACACCGCCTGCGACCTGGCGCCCCCGCCGGCACCACCGACGCCGCGCACCCGGGTTA
CTCTAGATAGATTGTATCGGCGCTGTTCCTGC

SEQ ID NO:32 (Hpa7):
AAATACGAGATCCACCGAGACTCCACACTGGACCCCTCCCTGATGGAGATGACAGAGGC
TGCCCTGCGCCTGCTGAGCAGGAACCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCACGTCTTCTCCTTCGGAGGCTACCCCTGCGAGGGAGCTCC
ATCTTCGGGCTGGCCCCTGGCAAGGCCCGGGACAGGAAGGCCTACACGGTCCTCCTATA
CGGAAACGGTCCAGGCTATGTGCTCAAGGACGGCGCCCGGCCGGATGTTACCGAGAGCG
AGAGCGGGTTAACGCCCCGAGTATCGGCAGCAGTCAGCAGTGCCCTGGACGAAGAGA
CCCACGCAGGCGAGGACGTGGCGGTGTTCGCGCGCGGCCCGCAGGCGCACCTGGTTCAC
GGCGTGCAGGAGCAGACCTTCATAGCGCACGTCATGGCCTTCGCCGCCTGCCTGGAGCCC
TACACCGCCTGCGACCTGGCGCCCCCGCCGGCACCACCGACGCCGCGCACCCGGGTTA
CTCTAGATAGATTGTATCGGCGCTGTTCCTGC

SEQ ID NO:33 (Hpa25):
AAATACGAGATCCACCGAGACTCCACACTGGACCCCTCCCTGATGGAGATGACAGAGGC
TGCCCTGCGCCTGCTGAGCAGGAACCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCACGTCTTCTCCTTCGGAGGCTACCCCTGCGAGGGAGCTCC
ATCTTCGGGCTGGCCCCTGGCAAGGCCCGGGACAGGAAGGCCTACACGGTCCTCCTATA
CGGAAACGGTCCAGGCTATGTGCTCAAGGACGGCGCCCGGCCGGATGTTACCGAGA**GTT
AAC**GAGAGCGGGAGCCCCGAGTATCGGCAGCAGTCAGCAGTGCCCTGGACGAAGAGA
CCCACGCAGGCGAGGACGTGGCGGTGTTCGCGCGCGGCCCGCAGGCGCACCTGGTTCAC
GGCGTGCAGGAGCAGACCTTCATAGCGCACGTCATGGCCTTCGCCGCCTGCCTGGAGCCC
TACACCGCCTGCGACCTGGCGCCCCCGCCGGCACCACCGACGCCGCGCACCCGGGTTA
CTCTAGATAGATTGTATCGGCGCTGTTCCTGC

Figure 11H

SEQ ID NO:34 (Hpa1):
AAATACGAGATCCACCGAGACTCCACACTGGACCCCTCCCTGATGGAGATGACAGAGGC
TGCCCTGCGCCTGCTGAGCAGGAACCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCCTGCGAGGGAGCTCC
ATCTTCGGGCTGGCCCCTGGCAAGGCCCGGGACAGGAAGGCCTACACGGTCCTCCTATA
CGGAAACGGTCCAGGCTATGTGCTCAAGGACGGCGCCCGGCCGGATGTTAACGAGAGC
GAGAGCGGGAGCCCCGAGTATCGGCAGCAGTCAGCAGTGCCCCTGGACGAAGAGACCC
ACGCAGGCGAGGACGTGGCGGTGTTCGCGCGCGGCCCGCAGGCGCACCTGGTTCACGGC
GTGCAGGAGCAGACCTTCATAGCGCACGTCATGGCCTTCGCCGCCTGCCTGGAGCCCTAC
ACCGCCTGCGACCTGGCGCCCCCGCCGGCACCACCGACGCCGCGCACCCGGGTTACTCT
AGATAGATTGTATCGGCGCTGTTCCTGC

SEQ ID NO:35 (Hpa13):
AAATACGAGATCCACCGAGACTCCACACTGGACCCCTCCCTGATGGAGATGACAGAGGC
TGCCCTGCGCCTGCTGAGCAGGAACCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCCTGCGAGGGAGCTCC
ATCTTCGGGCTGGCCCCTGGCAAGGCCCGGGACAGGAAGGCCTACACGGTCCTCCTATA
CGGAAACGGTCCAGGCTATGTGTTAACTCAAGGACGGCGCCCGGCCGGATGTTACCGAG
AGCGAGAGCGGGAGCCCCGAGTATCGGCAGCAGTCAGCAGTGCCCCTGGACGAAGAGA
CCCACGCAGGCGAGGACGTGGCGGTGTTCGCGCGCGGCCCGCAGGCGCACCTGGTTCAC
GGCGTGCAGGAGCAGACCTTCATAGCGCACGTCATGGCCTTCGCCGCCTGCCTGGAGCCC
TACACCGCCTGCGACCTGGCGCCCCCGCCGGCACCACCGACGCCGCGCACCCGGGTTA
CTCTAGATAGATTGTATCGGCGCTGTTCCTGC

SEQ ID NO:36 (Hpa35):
AAATACGAGATCCACCGAGACTCCACACTGGACCCCTCCCTGATGGAGATGACAGAGGC
TGCCCTGCGCCTGCTGAGCAGGAACCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCCTGCGAGGGAGCTCC
ATCTTCGGGCTGGCCCCTGGCAAGGCCCGGGACAGGAAGGCCTACACGGTCCTCCTATA
CGGAAACGGTCCAGGTTAACTATGTGCTCAAGGACGGCGCCCGGCCGGATGTTACCGAG
AGCGAGAGCGGGAGCCCCGAGTATCGGCAGCAGTCAGCAGTGCCCCTGGACGAAGAGA
CCCACGCAGGCGAGGACGTGGCGGTGTTCGCGCGCGGCCCGCAGGCGCACCTGGTTCAC
GGCGTGCAGGAGCAGACCTTCATAGCGCACGTCATGGCCTTCGCCGCCTGCCTGGAGCCC
TACACCGCCTGCGACCTGGCGCCCCCGCCGGCACCACCGACGCCGCGCACCCGGGTTA
CTCTAGATAGATTGTATCGGCGCTGTTCCTGC

Figure 11I

SEQ ID NO:37 (Hpa3):
AAATACGAGATCCACCGAGACTCCACACTGGACCCCTCCCTGATGGAGATGACAGAGGC
TGCCCTGCGCCTGCTGAGCAGGAACCCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCCTGCGAGGGAGCTCC
ATCTTCGGGCTGGCCCCTGGCAAGGCCCGGGACAGGAAGGCCTACACGGTCCTCCTATA
CGTTAACGGTCCAGGCTATGTGCTCAAGGACGGCGCCCGGCCGGATGTTACCGAGAGCG
AGAGCGGGAGCCCCGAGTATCGGCAGCAGTCAGCAGTGCCCCTGGACGAAGAGACCCAC
GCAGGCGAGGACGTGGCGGTGTTCGCGCGCGGCCCGCAGGCGCACCTGGTTCACGGCGT
GCAGGAGCAGACCTTCATAGCGCACGTCATGGCCTTCGCCGCCTGCCTGGAGCCCTACAC
CGCCTGCGACCTGGCGCCCCCGCCGGCACCACCGACGCCGCGCACCCGGGTTACTCTAG
ATAGATTGTATCGGCGCTGTTCCTGC

SEQ ID NO:38 (Hpa14):
AAATACGAGATCCACCGAGACTCCACACTGGACCCCTCCCTGATGGAGATGACAGAGGC
TGCCCTGCGCCTGCTGAGCAGGAACCCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCCTGCGAGGGAGCTCC
ATCTTCGGGCTGGCCCCTGGCAAGGCCCGGGACAGGAAGGCCTACACGGTTAACCTCCT
ATACGGAAACGGTCCAGGCTATGTGCTCAAGGACGGCGCCCGGCCGGATGTTACCGAGA
GCGAGAGCGGGAGCCCCGAGTATCGGCAGCAGTCAGCAGTGCCCCTGGACGAAGAGAC
CCACGCAGGCGAGGACGTGGCGGTGTTCGCGCGCGGCCCGCAGGCGCACCTGGTTCACG
GCGTGCAGGAGCAGACCTTCATAGCGCACGTCATGGCCTTCGCCGCCTGCCTGGAGCCCT
ACACCGCCTGCGACCTGGCGCCCCCGCCGGCACCACCGACGCCGCGCACCCGGGTTAC
TCTAGATAGATTGTATCGGCGCTGTTCCTGC

SEQ ID NO:39 (Hpa15):
AAATACGAGATCCACCGAGACTCCACACTGGACCCCTCCCTGATGGAGATGACAGAGGC
TGCCCTGCGCCTGCTGAGCAGGAACCCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCCTGCGAGGGAGCTCC
ATCTTCGGGCTGGCCCCTGGCAAGGCCCGGGACAGGAAGTTAACGCCTACACGGTCCTC
CTATACGGAAACGGTCCAGGCTATGTGCTCAAGGACGGCGCCCGGCCGGATGTTACCGA
GAGCGAGAGCGGGAGCCCCGAGTATCGGCAGCAGTCAGCAGTGCCCCTGGACGAAGAG
ACCCACGCAGGCGAGGACGTGGCGGTGTTCGCGCGCGGCCCGCAGGCGCACCTGGTTCA
CGGCGTGCAGGAGCAGACCTTCATAGCGCACGTCATGGCCTTCGCCGCCTGCCTGGAGCC
CTACACCGCCTGCGACCTGGCGCCCCCGCCGGCACCACCGACGCCGCGCACCCGGGTT
ACTCTAGATAGATTGTATCGGCGCTGTTCCTGC

Figure 11J

SEQ ID NO:40 (Hpa16):
AAATACGAGATCCACCGAGACTCCACACTGGACCCCTCCCTGATGGAGATGACAGAGGC
TGCCCTGCGCCTGCTGAGCAGGAACCCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCTGCGAGGGAGCTCC
ATCTTCGGGCTGGCCCCTGGCAAGGCCCGGGTTAACAGGAAGGCCTACACGGTCCTCCT
ATACGGAAACGGTCCAGGCTATGTGCTCAAGGACGGCGCCCGGCCGGATGTTACCGAGA
GCGAGAGCGGGAGCCCCGAGTATCGGCAGCAGTCAGCAGTGCCCTGGACGAAGAGAC
CCACGCAGGCGAGGACGTGGCGGTGTTCGCGCGCGGCCCGCAGGCGCACCTGGTTCACG
GCGTGCAGGAGCAGACCTTCATAGCGCACGTCATGGCCTTCGCCGCCTGCCTGGAGCCCT
ACACCGCCTGCGACCTGGCGCCCCCGCCGGCACCACCGACGCCGCGCACCCGGGTTAC
TCTAGATAGATTGTATCGGCGCTGTTCCTGC

SEQ ID NO:41 (Hpa17):
AAATACGAGATCCACCGAGACTCCACACTGGACCCCTCCCTGATGGAGATGACAGAGGC
TGCCCTGCGCCTGCTGAGCAGGAACCCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCTGCGAGGGAGCTCC
ATCTTCGGGCTGGCCCCTGGCAAGTTAACGCCCGGGACAGGAAGGCCTACACGGTCCTC
CTATACGGAAACGGTCCAGGCTATGTGCTCAAGGACGGCGCCCGGCCGGATGTTACCGA
GAGCGAGAGCGGGAGCCCCGAGTATCGGCAGCAGTCAGCAGTGCCCTGGACGAAGAG
ACCCACGCAGGCGAGGACGTGGCGGTGTTCGCGCGCGGCCCGCAGGCGCACCTGGTTCA
CGGCGTGCAGGAGCAGACCTTCATAGCGCACGTCATGGCCTTCGCCGCCTGCCTGGAGCC
CTACACCGCCTGCGACCTGGCGCCCCCGCCGGCACCACCGACGCCGCGCACCCGGGTT
ACTCTAGATAGATTGTATCGGCGCTGTTCCTGC

SEQ ID NO:42 (Hpa18):
AAATACGAGATCCACCGAGACTCCACACTGGACCCCTCCCTGATGGAGATGACAGAGGC
TGCCCTGCGCCTGCTGAGCAGGAACCCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCTGCGAGGGAGCTCC
ATCTTCGGGCTGGTTAACCCCTGGCAAGGCCCGGGACAGGAAGGCCTACACGGTCCTCC
TATACGGAAACGGTCCAGGCTATGTGCTCAAGGACGGCGCCCGGCCGGATGTTACCGAG
AGCGAGAGCGGGAGCCCCGAGTATCGGCAGCAGTCAGCAGTGCCCTGGACGAAGAGA
CCCACGCAGGCGAGGACGTGGCGGTGTTCGCGCGCGGCCCGCAGGCGCACCTGGTTCAC
GGCGTGCAGGAGCAGACCTTCATAGCGCACGTCATGGCCTTCGCCGCCTGCCTGGAGCCC
TACACCGCCTGCGACCTGGCGCCCCCGCCGGCACCACCGACGCCGCGCACCCGGGTTA
CTCTAGATAGATTGTATCGGCGCTGTTCCTGC

Figure 11K

SEQ ID NO:43 (Hpa19):
AAATACGAGATCCACCGAGACTCCACACTGGACCCCTCCCTGATGGAGATGACAGAGGC
TGCCCTGCGCCTGCTGAGCAGGAACCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCCTGCGAGGGAGCTCC
ATCGTTAACGGGCTGGCCCCTGGCAAGGCCCGGGACAGGAAGGCCTACACGGTCCTCCT
ATACGGAAACGGTCCAGGCTATGTGCTCAAGGACGGCGCCCGGCCGGATGTTACCGAGA
GCGAGAGCGGGAGCCCCGAGTATCGGCAGCAGTCAGCAGTGCCCCTGGACGAAGAGAC
CCACGCAGGCGAGGACGTGGCGGTGTTCGCGCGCGGCCCGCAGGCGCACCTGGTTCACG
GCGTGCAGGAGCAGACCTTCATAGCGCACGTCATGGCCTTCGCCGCCTGCCTGGAGCCCT
ACACCGCCTGCGACCTGGCGCCCCCGCCGGCACCACCGACGCCGCGCACCCGGGTTAC
TCTAGATAGATTGTATCGGCGCTGTTCCTGC

SEQ ID NO:44 (Hpa31):
AAATACGAGATCCACCGAGACTCCACACTGGACCCCTCCCTGATGGAGATGACAGAGGC
TGCCCTGCGCCTGCTGAGCAGGAACCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCCTGCGAGGGAGTTAA
CTCCATCTTCGGGCTGGCCCCTGGCAAGGCCCGGGACAGGAAGGCCTACACGGTCCTCCT
ATACGGAAACGGTCCAGGCTATGTGCTCAAGGACGGCGCCCGGCCGGATGTTACCGAGA
GCGAGAGCGGGAGCCCCGAGTATCGGCAGCAGTCAGCAGTGCCCCTGGACGAAGAGAC
CCACGCAGGCGAGGACGTGGCGGTGTTCGCGCGCGGCCCGCAGGCGCACCTGGTTCACG
GCGTGCAGGAGCAGACCTTCATAGCGCACGTCATGGCCTTCGCCGCCTGCCTGGAGCCCT
ACACCGCCTGCGACCTGGCGCCCCCGCCGGCACCACCGACGCCGCGCACCCGGGTTAC
TCTAGATAGATTGTATCGGCGCTGTTCCTGC

SEQ ID NO:45 (Hpa32):
AAATACGAGATCCACCGAGACTCCACACTGGACCCCTCCCTGATGGAGATGACAGAGGC
TGCCCTGCGCCTGCTGAGCAGGAACCCCGCGGCTTCTTCCTCTTCGTGGAGGGTGGTCG
CATCGACCATGGTCATCATGAAAGCAGGGCTTACCGGGCACTGACTGAGACGATCATGT
TCGACGACGCCATTGAGAGGGCGGGCCAGCTCACCAGCGAGGAGGACACGCTGAGCCTC
GTCACTGCCGACCACTCCCACGTCTTCTCCTTCGGAGGCTACCCCCTGTTAACGAGGGAG
CTCCATCTTCGGGCTGGCCCCTGGCAAGGCCCGGGACAGGAAGGCCTACACGGTCCTCCT
ATACGGAAACGGTCCAGGCTATGTGCTCAAGGACGGCGCCCGGCCGGATGTTACCGAGA
GCGAGAGCGGGAGCCCCGAGTATCGGCAGCAGTCAGCAGTGCCCCTGGACGAAGAGAC
CCACGCAGGCGAGGACGTGGCGGTGTTCGCGCGCGGCCCGCAGGCGCACCTGGTTCACG
GCGTGCAGGAGCAGACCTTCATAGCGCACGTCATGGCCTTCGCCGCCTGCCTGGAGCCCT
ACACCGCCTGCGACCTGGCGCCCCCGCCGGCACCACCGACGCCGCGCACCCGGGTTAC
TCTAGATAGATTGTATCGGCGCTGTTCCTGC

Nuclear receptor ligand-binding binding domains (NR LBD) used in RTU constructs:

GR RTU: Glucocorticoid receptor (GR)
ER RTU: Estrogen receptor (ER)
VDR RTU: Vitamin D receptor (VDR)
CAR RTU: Constitutive androstane receptor (CAR)
THR RTU: Thyroid hormone receptor alpha (THRα)

VDR— Vitamin D receptor
GR— Glucocorticoid receptor
ER— Estrogen receptor
THRα— Thyroid hormone receptor α
CAR— Constitutive androstane receptor Mitogen activated protein kinase (MAPK) substrates used in RTU constructs:

ERK RTU: Elk 1 transactivating domain (TAD)
JNK RTU: c-Jun TAD
p38 MAPK: ATF-2 TAD

REPORTER TRANSCRIPTION UNIT POPULATIONS AND KITS COMPRISING SAME

This application claims the benefit of U.S. Provisional Application No. 60/626,663, filed Nov. 10, 2004, the contents of which is incorporated herein by reference in its entirety.

The present invention was made, in part, with grants from the National Institutes of Health (NIH)/Small Business Innovation Research (SBIR) Grant No. CA101271-1 and No. CA101636-02. The government of the United States may have certain rights in this invention.

1. TECHNICAL FIELD

The invention relates to compositions, methods and kits that utilize a polynucleotide reporter system to detect activities of multiple trans-acting factors, such as nuclear hormone receptors and transcription factors, in biological systems.

2. BACKGROUND OF THE INVENTION

Cell identity and behavior are determined by the repertoire of genes that are expressed within the particular cell. Of approximately 26,000 genes that are present in the human genome, only a fraction is expressed within a particular cell type at a given time. Cells alter the pattern of gene expression in order to accommodate the changing environment. Multiple mechanisms are employed by the cell to regulate gene expression. For instance, regulatory sequences such as promoters and enhancers, which are usually found in untranslated regions of genes, contain elements that are specifically recognized by intracellular DNA-binding proteins that are called transcription factors (TFs). The binding of transcription factors to their cognate sites in a regulatory sequence controls the recruitment of the basal transcription machinery that initiates gene transcription. The ability of cis-regulatory sequences and transcription factors to activate transcription is referred to as the transcriptional activity. Gene expression is also known to be regulated at the post-transcriptional level. For example, many RNAs contain cis-regulatory elements that regulate the maturation, stability, and or degradation of RNA transcripts. The multiple mechanisms of regulating transcript levels allow cells to maintain the homeostatic regulation of gene expression.

Impairments of the finely tuned regulation can cause cell death, transformation, or metabolic diseases. Therefore, it is important to put in place technologies that enable the assessment of the activities of the machinery that controls gene expression.

For example, easily detected reporter proteins, such as luciferase, chloramphenicol acetyltransferase, and green fluorescent protein, can be made to be expressed by reporter constructs that are introduced into a cell. Detecting reporter proteins, however, is not well suited for assays intended to measure multiple transcriptional activities. This is due, in part, to the relatively small numbers of protein products amenable to convenient and rapid detection, and to the differences in transcribed amounts and stabilities between different reporter proteins.

Another broad class of approaches to assess gene expression is based on the evaluation of the amounts of gene transcripts, e.g., Northern blotting, reverse transcription PCR, and RNA array hybridization. However, as RNA abundance is regulated by many mechanisms, including the transcriptional regulation, RNA processing, accumulation, and degradation, these methods provide limited information about the activities of cis-regulatory sequences and trans-acting factors. Moreover, while the use of reporter construct libraries to detect multiple transcription factor activities have been described (see, e.g., U.S. patent application Publication Ser. Nos. 2003/0148287 and 2003/0143547), the problems associated detecting RNA abundance, including differences in the transcription levels, methylation, stability, hybridization efficacy, and susceptibilities to RNAses, that exist between different reporter RNAs expressed by reporter construct libraries, have not been addressed.

As transcription factors need to bind their cognate DNA sequence in order to initiate transcription, DNA binding has been widely used as a marker of transcription factor activation. Gel-shift assay, also known as EMSA, is a classical method for assessing DNA binding. However, many mechanisms exist that can effect the activity of transcription factors at multiple levels of regulation independently from DNA binding (Baldwin (2001) *J Clin Invest* 107:241-246). Therefore, DNA binding assays provide only limited information about the ability of transcription factors to activate transcription.

As impaired regulation of various transcription factors has been associated with various human diseases, including chronic inflammatory conditions, autoimmunity, and cancer (see, e.g., Makarov (2000) *Mol Med Today* 6:441-448; Baldwin et al. (2001) *J. Clin Invest* 107:241-246), transcription factors are considered attractive targets for drug development. To screen libraries of synthetic or biological compounds for their ability to selectively modulate the transcriptional activity of transcription factors of interest, one needs an appropriate assay enabling high throughput profiling of numerous transcription factors. To start addressing these questions, the art requires technology that permits the profiling of the activities of numerous transcription factors. The progress in this area has been hampered by the lack of adequate tools.

3. SUMMARY OF THE INVENTION

In one aspect, the present invention relates to compositions, methods and kits utilizing a population of reporter transcription units (RTUs), wherein each RTU of the population comprises a reporter sequence, a processing tag, and a cis-regulatory element operably linked to the reporter sequence. The processing tag can be located in, that is, within or adjacent to, the reporter sequence. As described below, the reporter sequences in the RTUs generally exhibit minimal differences, for example, in the efficacy of transcription and detection and thus afford highly uniform performance of RTUs in the population. Even in embodiments exhibiting substantial identity between the reporter sequences in the RTU population, the combination of the reporter sequences with the processing tags described herein afford minimal cross-interference of individual reporter species that can be detected with very low non-specific background.

In one aspect, compositions are provided comprising a reporter transcription unit (RTU) population comprising polynucleotide RTUs, each RTU comprising a reporter sequence; a processing tag located in the reporter sequence; and a cis-regulatory element operably linked to the reporter sequence, wherein transcription of the reporter sequence is modulated by a trans-acting factor or factors that bind to the cis-regulatory element.

In certain embodiments, the non-processing tag portion of the reporter sequences in the RTU population can be substantially identical, or even identical. In certain embodiments, the substantially identical reporter sequences differ by 10, 9, 8, 7, 6, 5, 4, 3, 2 or even 1 nucleotide. Without intending to be bound by any particular theory or mechanism, substantially identical reporter sequences minimize alterations in detection conditions, thereby allowing the RTU population to be used for highly reproducible assessments.

In some embodiments, the reporter sequences differ by 10, 9, 8, 7, 6, 5, 4, 3, 2 or even 1 nucleotide wherein the differences are due to the processing tag in the reporter sequences.

In certain embodiments, the reporter sequences of the RTU population differ only by location of the processing tags in the reporter sequence.

In some embodiments, the population of RTUs comprises more than 2, 10, 50, 100, 500, 1000, 1500, 2000, 2500 or more non-identical RTUs. Accordingly, activities of more than 2, 10, 50, 100, 500, 1000, 1500, 2000, 2500 or more trans-acting factors or cis-regulatory elements can be determined using the RTU population.

The positions of the processing tags in the reporter sequences can distinguish between any two RTUs having reporter sequences transcriptionally modulated by non-identical trans-acting factors. Processing tags can, for example, be selected from the group consisting of a unique thymine, adenine, cytosine, or guanine nucleotide residue; an endonuclease recognition site; a primer sequence; an extension termination signal; and a mutation in the reporter sequence comprising a deletion, insertion, or substitution.

In certain embodiments, the processing tag can be as short as one nucleotide and can represent a substitution, an insertion or a deletion of a single or several nucleotides in an otherwise common reporter sequence in a RTU population.

In certain embodiments, the positions of the processing tags in the reporter sequences distinguish between any two RTUs having non-identical cis-regulatory elements.

In some embodiments, the cis-regulatory elements in the RTU population can comprise a promoter, an enhancer, an RNA stability signal, and a polyadenylation signal or a combination thereof. Typically, a cis-regulatory element has at least one binding site for a DNA-binding protein.

In another aspect, the present invention provides a population of vectors comprising an RTU population as described herein.

In another aspect, the present invention provides a cell comprising an RTU population as described herein. In certain embodiments, an RTU population is stably incorporated into the genome of the cell. A cell of the present invention can, for example, be selected from the group consisting of a plant, a bacterium, a fungus, and a vertebrate.

In yet another aspect, the present invention provides a tissue or a non-human organism comprising a cell, wherein the cell comprises an RTU population as described herein.

In one aspect, the present invention provides methods of determining activities of multiple trans-acting factors or of multiple cis-regulatory elements in a biological system, where the biological system comprises an RTU population of the present invention.

For example, reporter species of reporter sequences expressed by members of the RTU population can be isolated, typically amplified, and processed to distinguish between different reporter species. Processing can include, for example, (a) cleaving reporter species with an endonuclease, where the processing tags are restriction sites; (b) cleaving reporter species with a mismatch-specific nuclease, where the processing tags comprise one or more nucleotides that do not match a hybridization polynucleotide complementary to the reporter species; (c) thermolysis of uracil-glycosylated reporter species, where the processing tag comprises a uracil in the reporter species that do not otherwise have uracil; and (d) amplifying reporter species, where the processing tag comprises an amplification termination site or a primer sequence.

Reporter species of RTUs can be detected, for example, by detection of processed oligonucleotide detection probes. A detection probe typically comprises a sequence that is complementary to an RTU reporter species encompassing the processing tag. Due to differences between reporter species, for example, differences in the positions of the processing tags, or in the nucleotides comprising the processing tags, and so forth, oligonucleotide detection probes can be used to distinguish between reporter species. In some embodiments, detection probes further comprise a label, e.g., a fluorescent label whose fluorescent properties can be modulated by processing. In some embodiments, detection probes can be in an array or attached to a solid substrate.

In certain embodiments, methods are provided for determining the activities of multiple trans-acting factors or multiple cis-regulatory elements, comprising processing reporter species of the reporter sequences; and detecting at least two of the processed reporter species, thereby determining the relative activities of multiple trans-acting factors or multiple cis-regulatory elements.

In some embodiments, methods are provided to assess the effect of a treatment on a biological system comprising an RTU population comprising determining the effect of the treatment on activities of multiple individual trans-acting factors, or multiple individual cis-regulatory elements in a biological system relative to the activities of the multiple individual trans-acting factors, or the multiple individual cis-regulatory elements in a biological system not subjected to the treatment.

In some embodiments, methods are provided for assessing the effect of a treatment on the activities of multiple trans-acting factors, or multiple cis-regulatory elements, in a biological system, wherein the biological system comprises an RTU population, the method comprising: subjecting the biological system to a treatment; processing reporter species of the reporter sequences; and detecting at least two of the processed reporter species, thereby assessing the effect of the treatment on the activities of multiple trans-acting factors or multiple cis-regulatory elements.

In certain embodiments of the methods provided for assessing the effect of a treatment on the activities of multiple trans-acting factors, or multiple cis-regulatory elements, in a biological system, the method further comprises determining the activities of multiple individual trans-acting factors or multiple cis-regulatory elements in the biological system subjected to the treatment relative to the activities of the multiple trans-acting factors or the multiple cis-regulatory elements in a biological system that is not subjected to the treatment.

In some embodiments, methods are provided for generating a trans-acting factor activity profile, or a cis-regulatory activity profile, for a biological system, wherein the biological system comprises an RTU population, the method comprising: processing reporter species of the reporter sequences of the RTU population and detecting the processed reporter species thereby generating a trans-acting factor activity profile, or a cis-regulatory activity profile, for the biological system. In certain embodiments, such methods further comprise recording, storing or communicating a trans-acting factor activity profile, or a cis-regulatory activity profile, for a biological system comprising an RTU population. In some embodiments, a trans-acting factor activity profile, or a cis-regulatory activity profile, for a biological system is recorded or stored in a tangible medium, such as, for example, paper, plastic transparency or a computer readable storage medium.

In some embodiments, the present invention provides methods for identifying a cell type, comprising: comparing a first trans-acting factor activity profile (or first cis-regulatory activity profile) generated for a cell of interest to a second trans-acting factor activity profile (or second cis-regulatory activity profile) generated for a cell of known cell type to determine if the first trans-acting factor activity profile (or first cis-regulatory activity profile) matches the second trans-acting factor activity profile (or second cis-regulatory activity profile), wherein the cell type of the cell of interest is identified where a match is determined to be present when the first trans-acting factor activity profile (or first cis-regulatory activity profile) is compared to the second trans-acting factor activity profile (or second cis-regulatory activity profile).

In some embodiments, the present invention provides methods for identifying a disease state, comprising comparing a trans-activating factor activity (or a cis-regulatory activity) profile generated in a cell of interest to that in a cell with a predetermined disease state.

In some embodiments, methods are provided for assessing the function of a molecule of interest in a cell, comprising comparing a trans-activating factor activity (or a cis-regulatory activity) profile generated in a cell for which the molecule of interest has been intracellulary introduced, or for which the amount or activity of the molecule of interest in the cell has been modulated, to a trans-activating factor activity (or a cis-regulatory activity) profile generated in a cell for which the molecule of interest is absent, or for which the amount or activity of the molecule of interest in the cell has not been modulated. A molecule of interest can, for example, be a polynucleotide or polypeptide of interest. For example, where the molecule of interest is a polypeptide, modulating its activity in a cell can include, for example, increasing or inhibiting enzymatic activity, increasing or inhibiting binding activity, posttranslationally modifying the polypeptide, and so forth. As another example, where the molecule of interest is polynucleotide, modulating its amount in a cell can include its overexpression, knock-out, e.g., by genetic recombination, knock-down, e.g., by using small interfering RNAs or antisense oligonucleotides, etc., and so forth.

In some embodiments, methods are provided for determining relative numbers of different cell types in a mixed-type cell population, wherein the mixed-type cell population comprises the RTU population of the invention, and wherein each type of cell in the cell population comprises at least one RTU member of the RTU population, the method comprising processing the reporter sequences expressed by the RTU population; and determining the relative amounts of detected processed reporter sequences, thereby determining the relative numbers of different cell types in a mixed-type cell population.

In another aspect, the present invention provides kits comprising an RTU population as described herein. Kits as provided herein can, for example, include cells or vectors that comprise an RTU population. In some embodiments, kits can further comprise directions for use of the RTU population, or for use of cells or vectors comprising the RTU population, as appropriate to the contents of the kit.

In some embodiments, kits can include polynucleotides that be used to create an RTU population. For example, kits can include a population of plasmids wherein each plasmid comprises a reporter sequence, a processing tag, and a multiple cloning site by which a cis-regulatory sequence can be introduced to the plasmid and thereby be operably linked to the reporter sequence.

In certain embodiments, kits can include one or more transacting factor activity profiles or cis-regulatory activity profiles.

4. BRIEF DESCRIPTION OF THE FIGURES

FIG. 1 provides a non-limiting schematic exemplifying how reporter species from two reporter sequences can be distinguished in the methods provided herein. Depicted are individual reporter transcription units (RTUs) (Reporter A and Reporter B) comprising a cis-regulatory sequence (2) operably linked to a reporter sequence (4) having a processing tag (6) differentially positioned within the reporter sequences of the two RTUs such that upon processing expressed reporter transcript (8), processed reporter species (9) are produced that can be distinguished based on the different positions of the processing tag.

Figure 2:
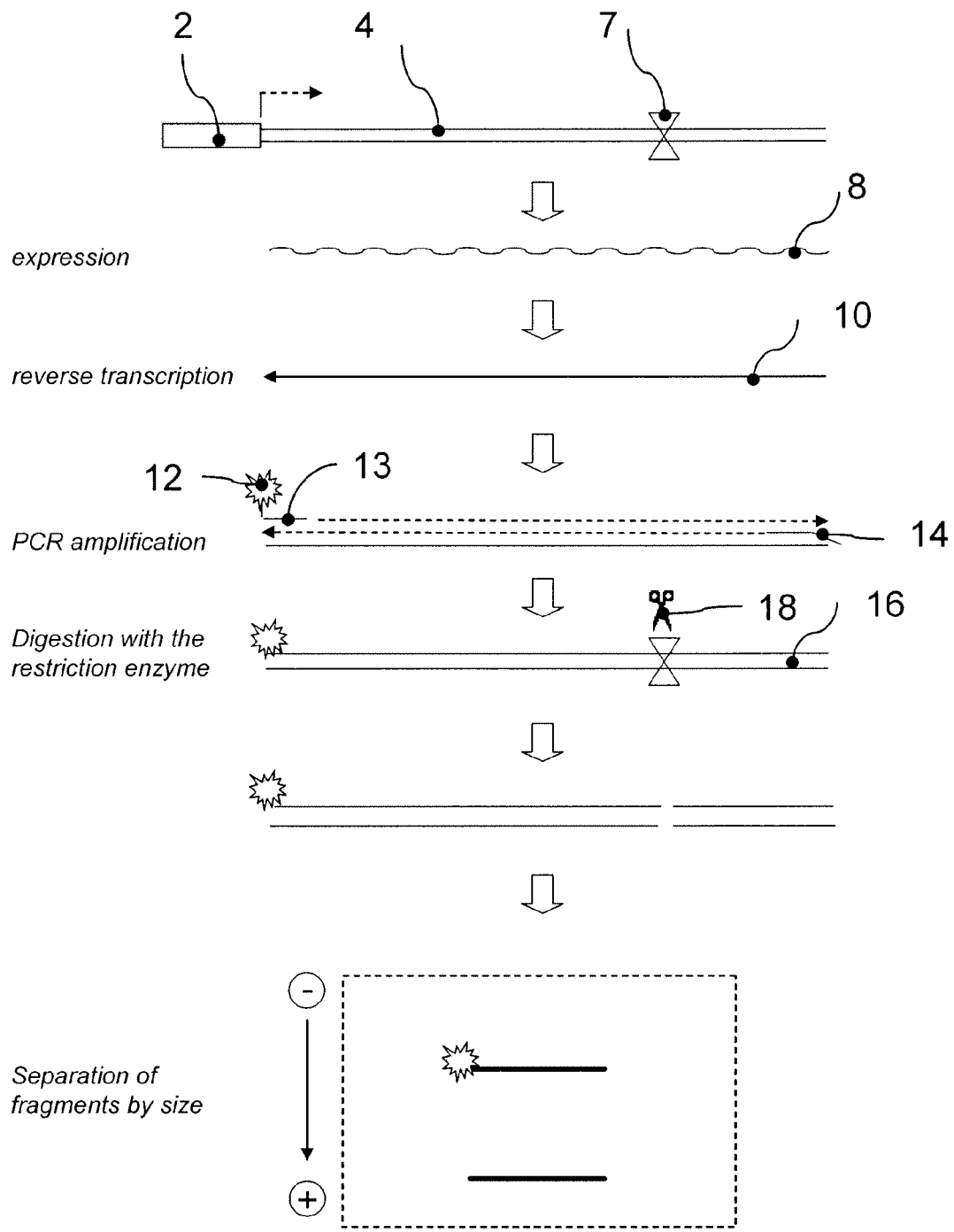

FIG. 2 provides a non-limiting embodiment of the invention wherein the processing tag comprises an endonuclease recognition site. The elements depicted in the figure are as follows: (2) cis-regulatory sequence; (4) reporter sequence; (7) processing tag comprising an endonuclease recognition site; (8) reporter RNA transcript; (10) reporter cDNA; (12) label; (13) forward primer for amplification of the reporter cDNA; (14) reverse primer for amplification of the reporter cDNA; (16) labeled PCR product; and, (18) DNA endonuclease.

Figure 3:
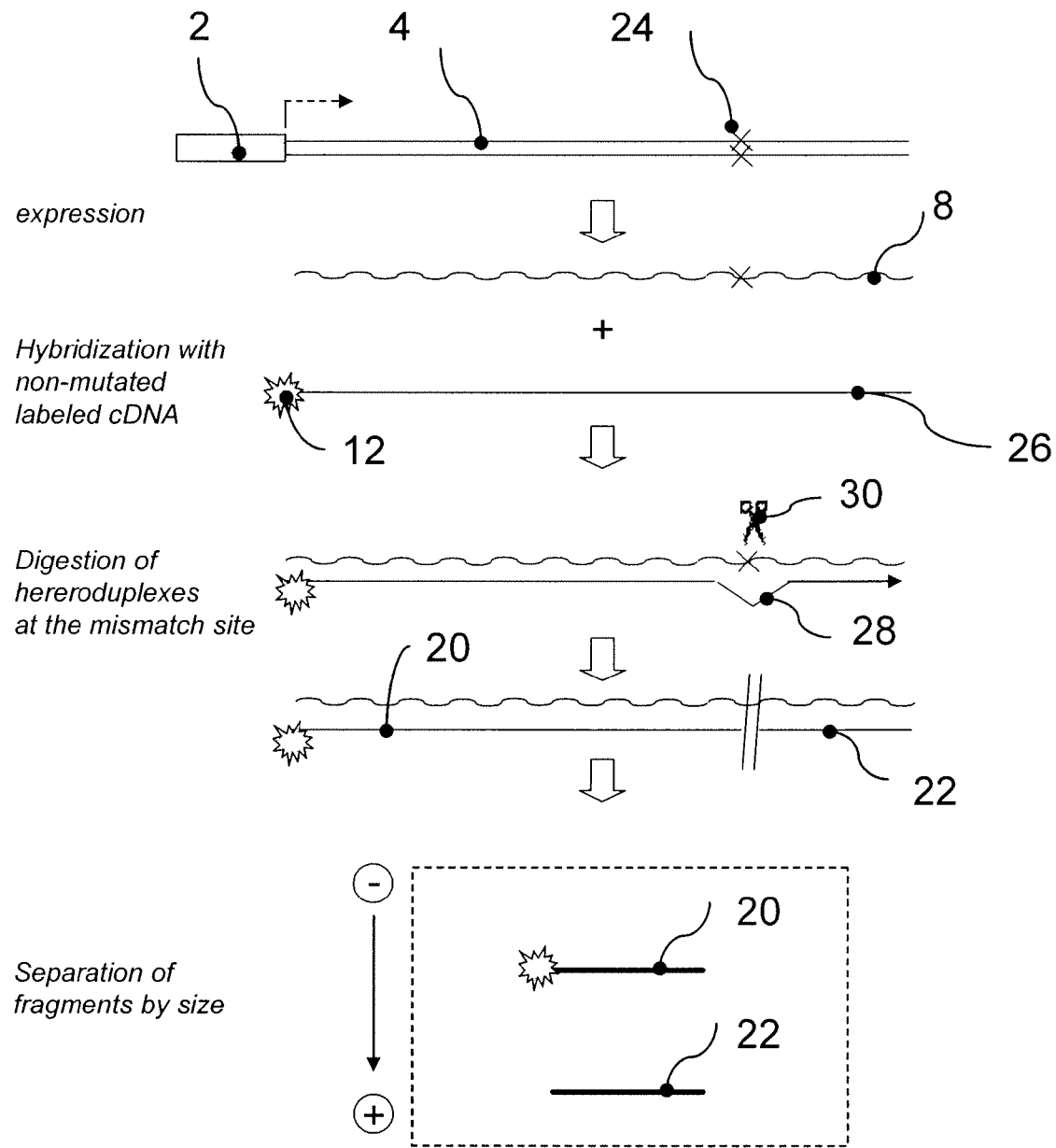

FIG. 3 illustrates a non-limiting embodiment of the invention wherein the processing tag comprises a mutation in the reporter DNA sequence which when hybridized with a wild-type complementary labeled cDNA that does not contain the processing tag will form a mismatch in the strands. A mismatch-specific nuclease is used to cleave the labeled complementary cDNA. The sequences are then separated based on size. The elements shown in the figure are as follows: (2) cis-regulatory sequence; (4) reporter sequence; (24) processing tag comprising a mutation; (8) reporter RNA transcript; (12) label; (26) wild-type (wt) reporter DNA; (30) mismatch-specific nuclease; (28) mismatch site in the double stranded heteroduplex; (20) labeled fragment of processed DNA; and (22) unlabeled fragment of processed DNA.

Figure 4:
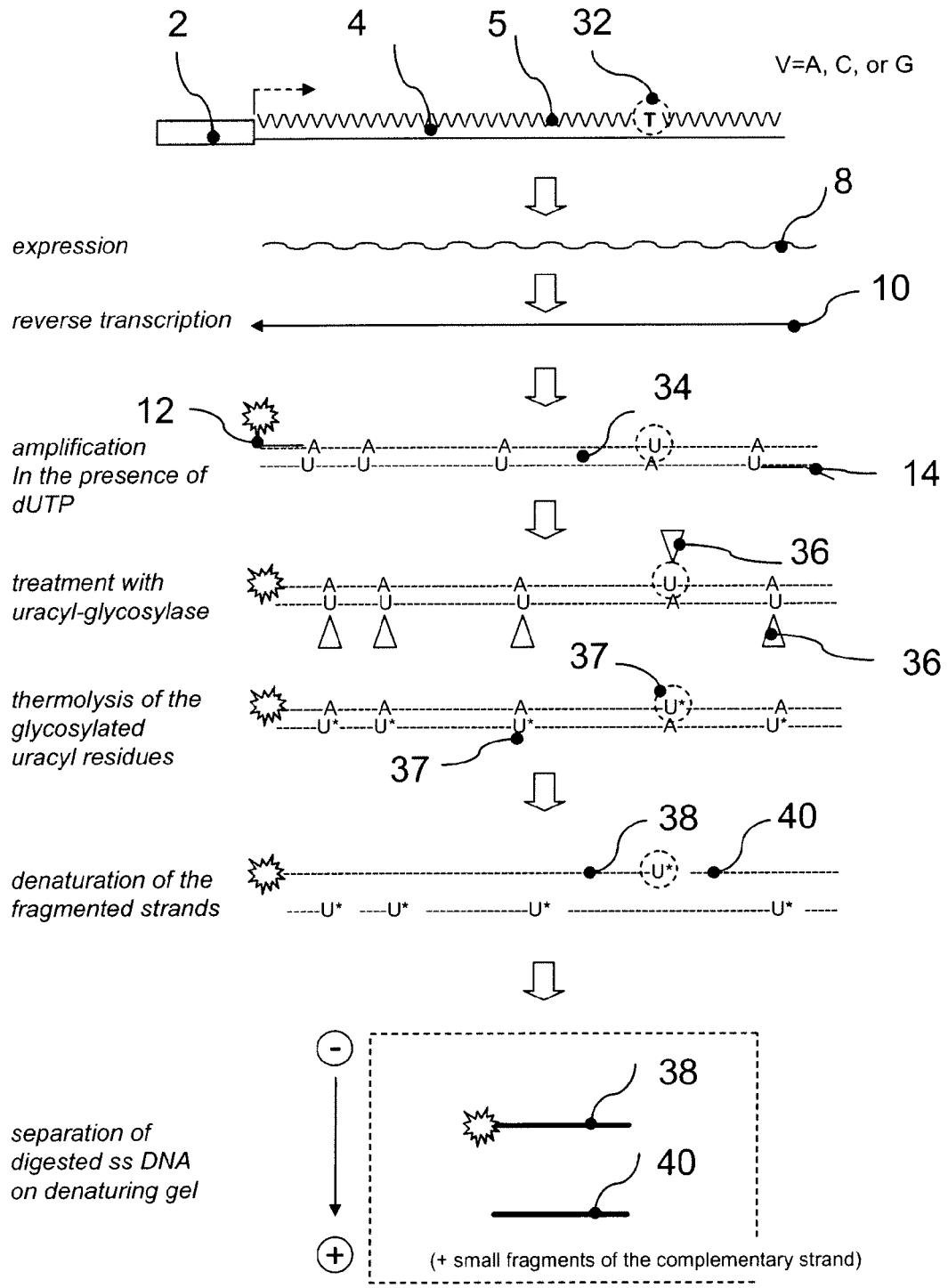

FIG. 4 represents a non-limiting embodiment of the invention wherein the processing tag comprises a unique thymidine residue in one of the strands of reporter DNA. The elements shown are as follows: (2) cis-regulatory sequence; (4) reporter sequence; (5) transcribed strand of the reporter sequence; (32) processing tag comprising a unique thymidine residue; (8) reporter RNA transcript; (10) reporter cDNA; (12) label; (34) uracyl—containing PCR product; (14) reverse primer for amplification of the reporter cDNA; (36) uracyl-glycosydase; (37) deglycosylated uracyl residue; (38) labeled strand of amplified reporter cDNA containing single deglycosylated uracyl residue; and (40) unlabeled fragment of amplified reporter DNA.

FIGS. 5A and 5B represent non-limiting embodiments of the invention wherein the processing tag comprises a termination site. The elements are as follows: (2) cis-regulatory sequence; (4) reporter sequence; (8) reporter RNA transcript; (10) reporter cDNA; (13) forward primer for amplification of the reporter cDNA; and (44) extended labeled fragment strand of reporter cDNA terminated at the processing site (42).

Figure 6:
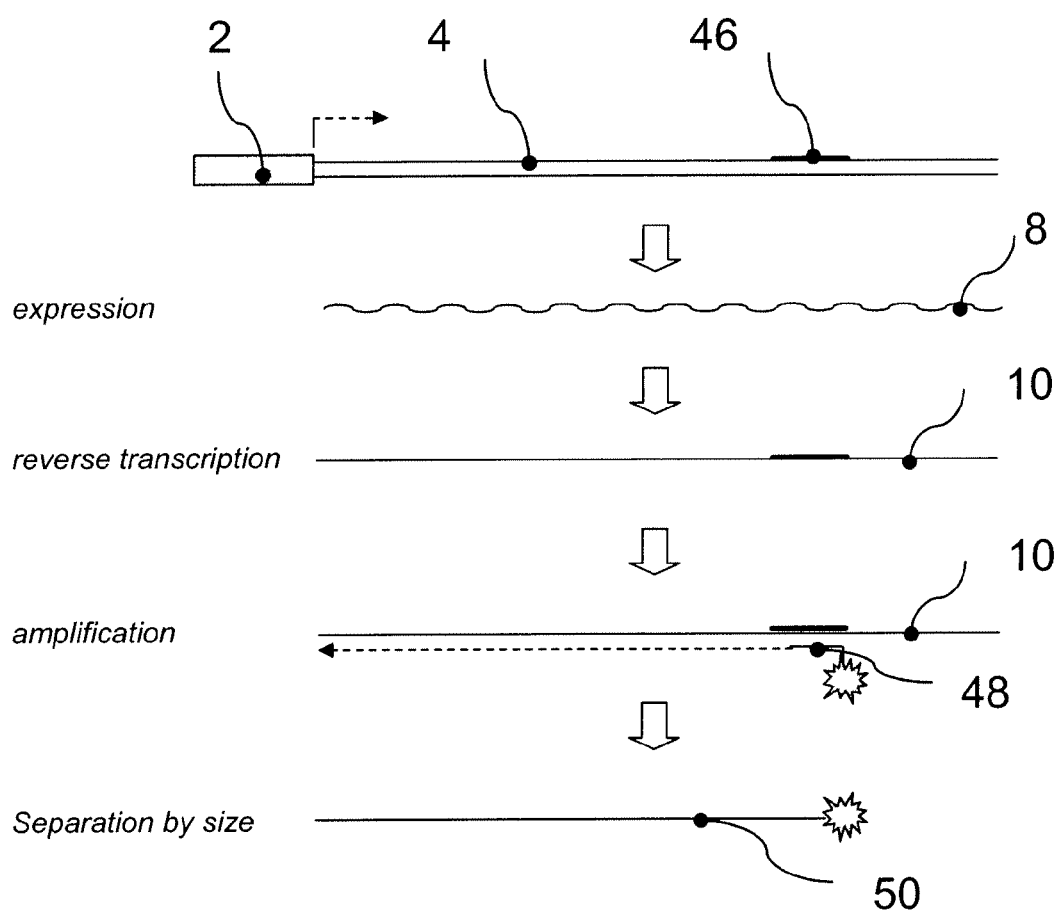

FIG. 6 represents a non-limiting embodiment wherein the processing tag comprises a defined oligonucleotide sequence for primer extension. The elements are as follows: (2) cis-regulatory sequence; (4) reporter sequence; (46) processing tag comprising a defined primer sequence; (8) reporter RNA transcript; (10) reporter cDNA; (48) labeled primer complementary to the defined primer sequence; and (50) labeled primer extension product.

Figure 7:
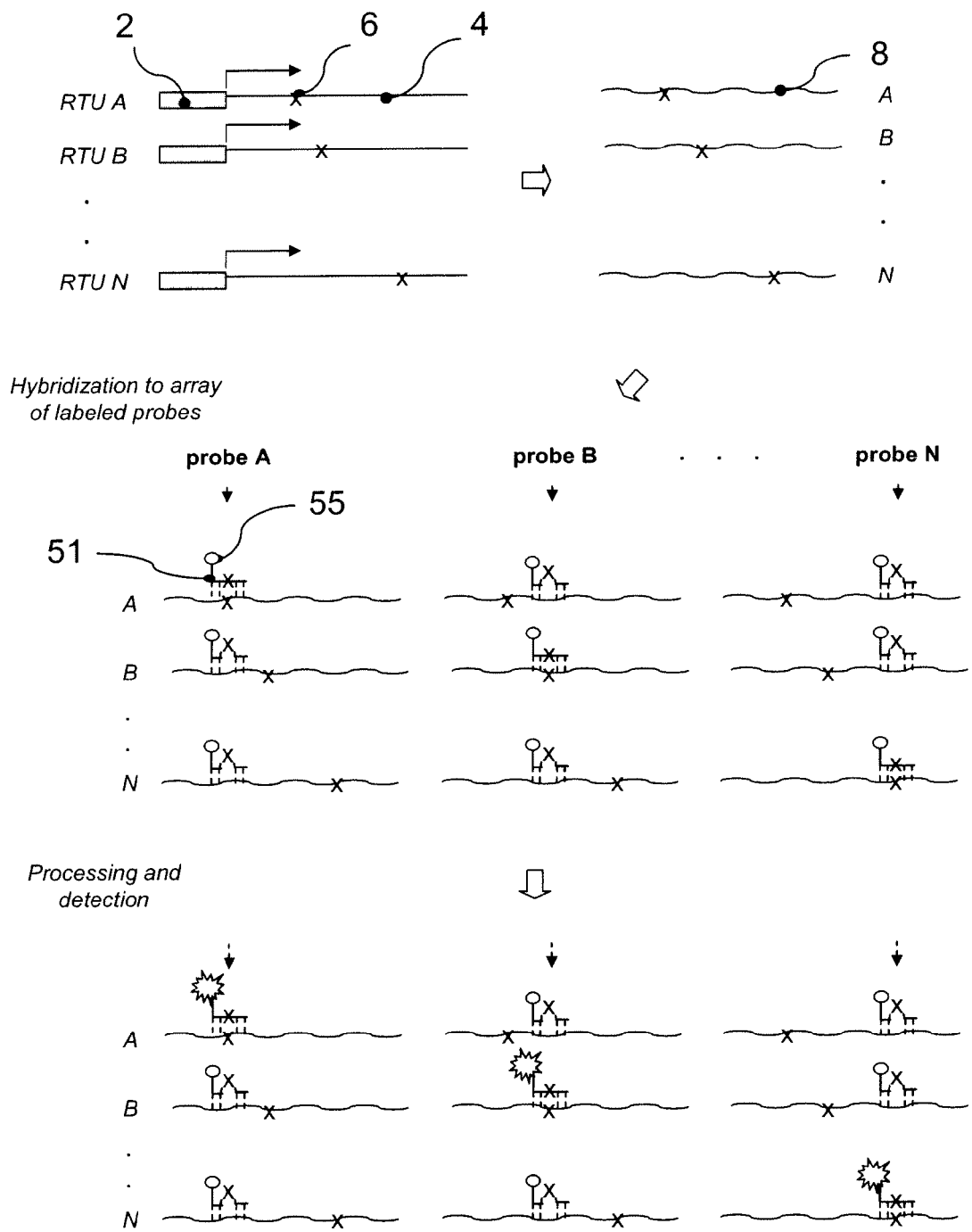

FIG. 7 provides a non-limiting schematic exemplifying how N reporter species can be distinguished in the methods provided herein. Depicted are reporter transcription units (RTUs) wherein an individual RTU comprises a cis-regulatory sequence (2) operably linked to a reporter sequence (4) having a processing tag (6) differentially positioned among the RTUs. Reporter species are annealed with an array of oligonucleotide detection probes (51) wherein an individual detection probe comprises an RTU reporter sequence spanning the processing tag site (marked X) in an individual RTU and further comprises a fluorescent label (55) whose fluorescence can be modulated by processing. The duplexes of reporter species and detection probes are processed as appropriate according to the nature of the processing tag. Only the duplexes wherein oligonucleotide detection probe (51) is completely complementary to the reporter species can be processed and thus can be detected by observing altered fluorescence.

Figure 8:
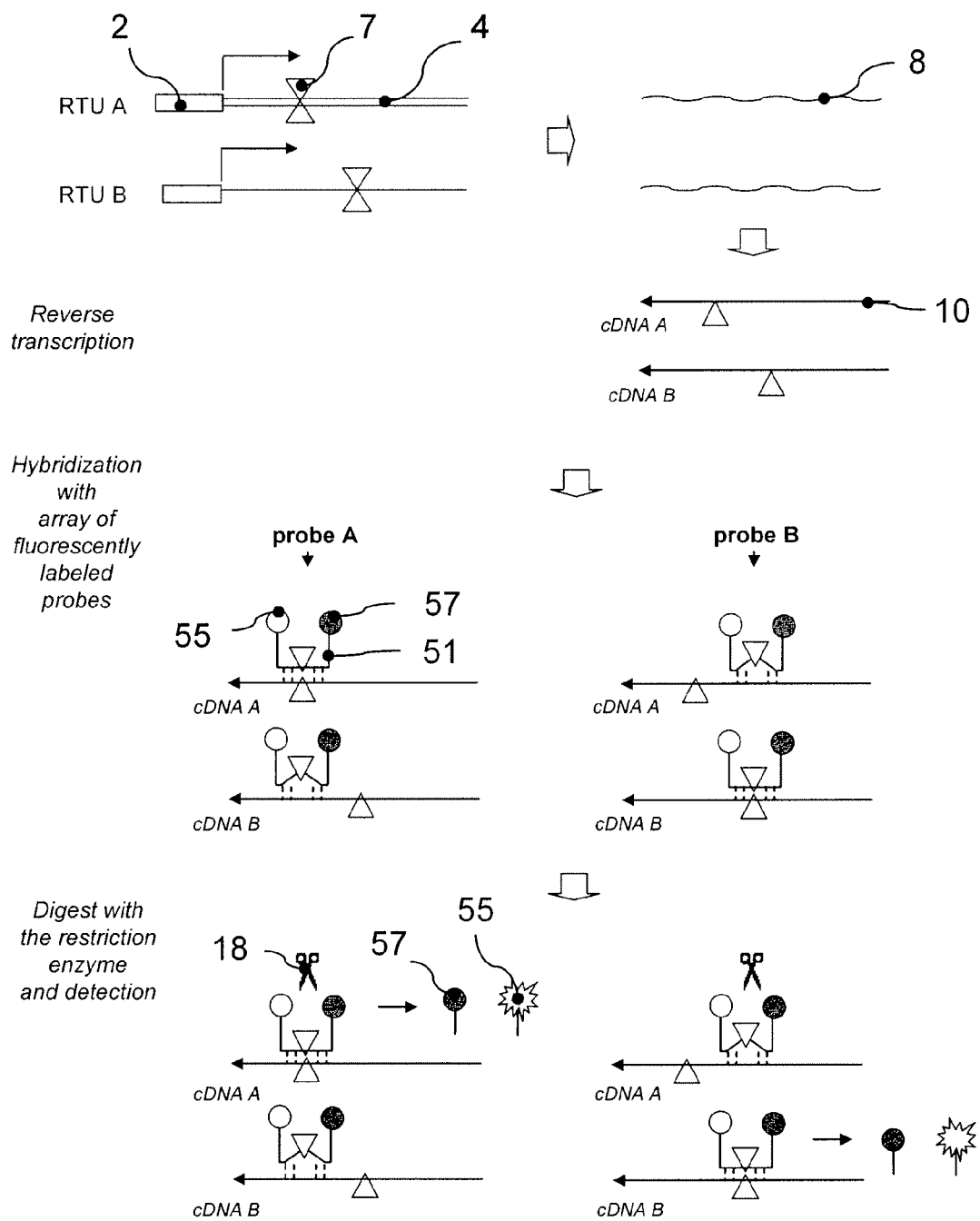

FIG. 8 represents a non-limiting embodiment of the present invention that utilizes hybridization to oligonucleotide detection probes, wherein the processing tag comprises an endonuclease restriction site by which reporter species can be distinguished. The elements are as follows: (2) cis-regulatory sequence; (4) reporter sequence; (7) processing tag comprising a endonuclease restriction site; (8) reporter RNA transcript; (10) reporter cDNA; (51) detection probe; (55) fluorescent label; (57) quencher; and (18) restriction enzyme.

Figure 9:
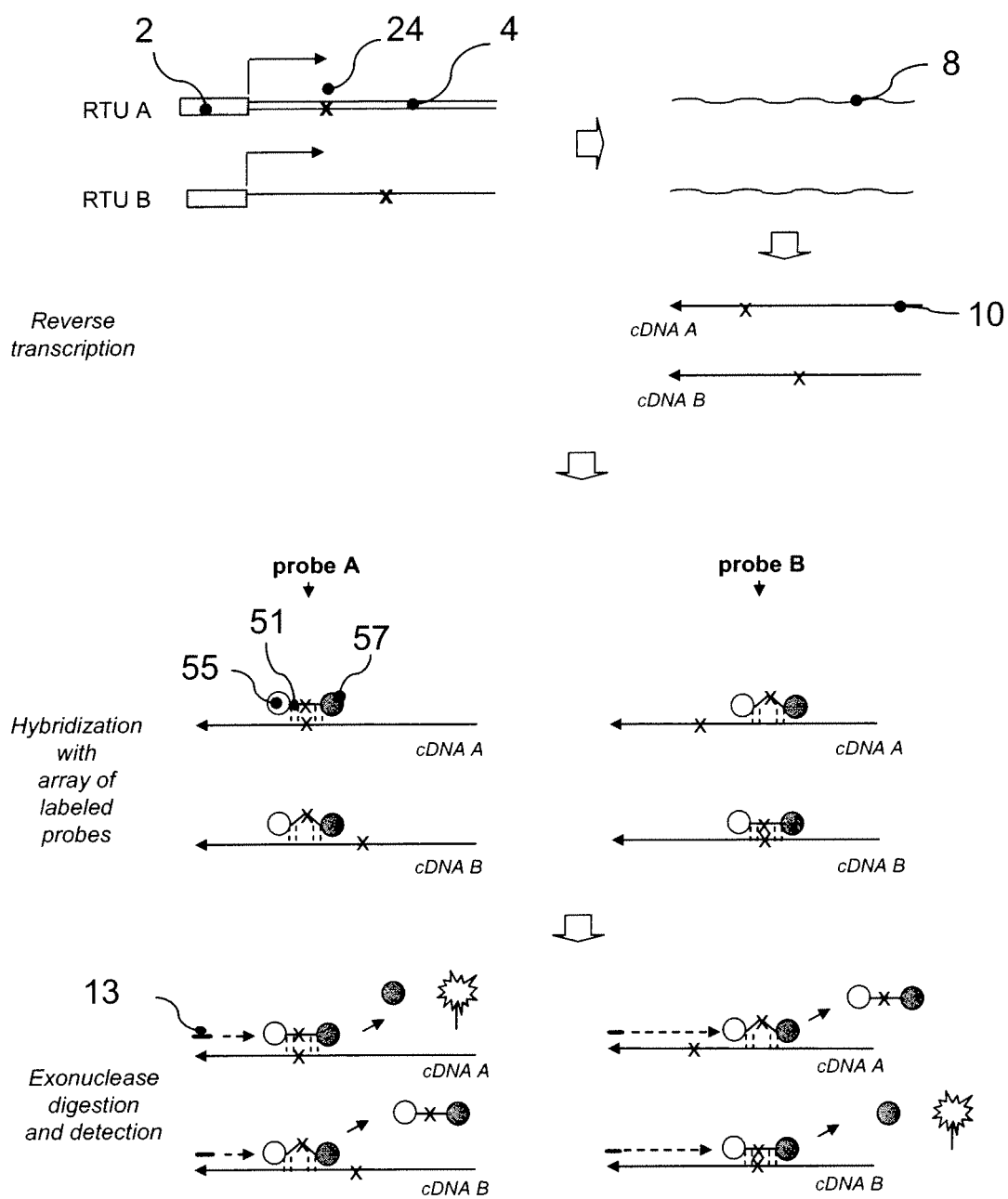

FIG. 9 represents a non-limiting embodiment of the present invention that utilizes hybridization to oligonucleotide detection probes, wherein the processing tag comprises a mutation of the common reporter sequence. The elements are as follows: (2) cis-regulatory sequence; (4) reporter sequence; (24) processing tag comprising a mutation; (8) reporter RNA transcript; (10) reporter cDNA; (51) detection probe; (55) fluorescent label; (57) quencher (57); and (13) forward primer for primer extension of the reporter cDNA by DNA polymerase possessing 5' to 3' exonuclease activity.

Figure 10:
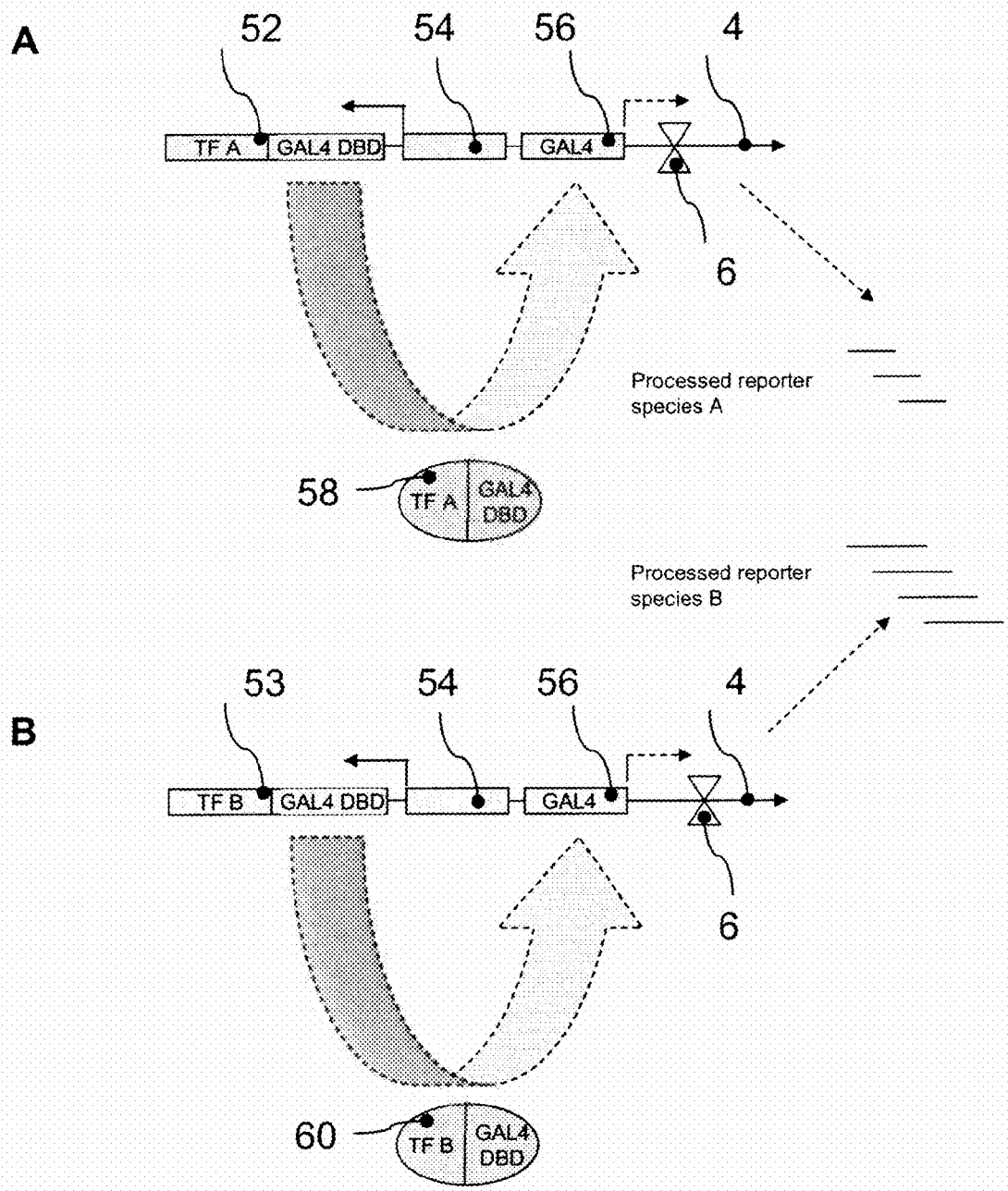

FIG. 10 provides a non-limiting embodiment of the present invention for detecting activities of multiple transcription factors possessing unknown or redundant DNA binding sequences, as discussed in the Detailed Description.

FIGS. 11A-K provide the sequences of the common, wild-type reporter sequence (SEQ ID NO:13) comprising a sequence of secreted alkaline phosphatase (SEAP) lacking a processing tag, and thirty two exemplary reporter sequences with variably positioned processing tags (SEQ ID NOS:14-45) comprising a HpaI restriction site, where the nucleotides in bold identify the processing tag.

Figure 12:
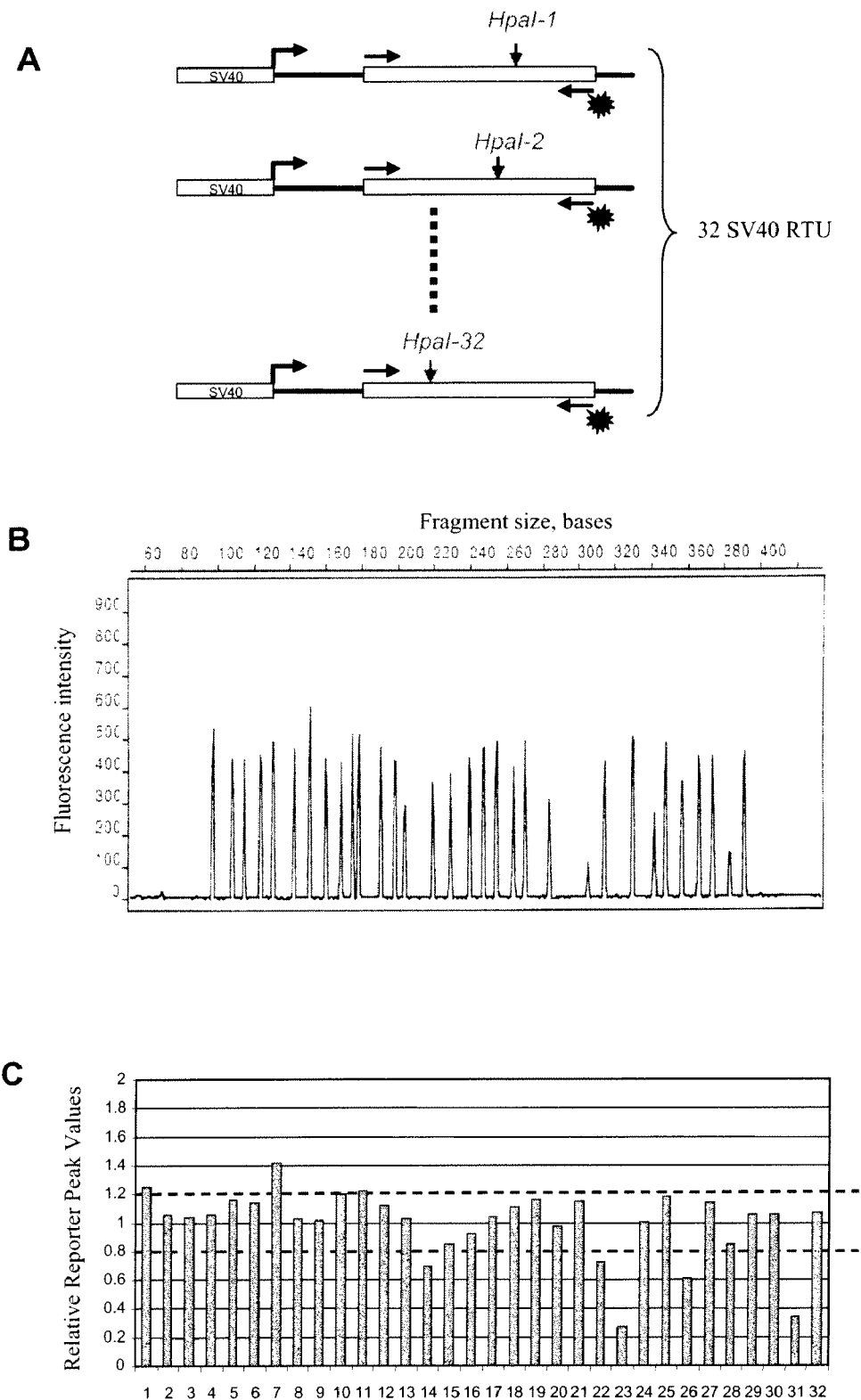

FIG. 12 provides a non-limiting schematic of the design of a population comprising thirty two RTUs, wherein individual RTUs comprise a common SV40 promoter and one of the reporter sequences (SEQ ID NOS:14-45) exemplified in FIG. 11, as discussed in the Examples (A); representative data of the expression of individual RTUs as assessed by detecting processed reporter species using capillary electrophoresis (B); and normalized peak values of each of the thirty two reporter species (C).

FIG. 13 provides a non-limiting example of using a population of RTUs for assessing effects of treatments on cells. HEK293 were transfected with eleven RTUs comprising inducible promoters and three calibrating RTUs comprising a SV40 promoter, wherein the reporter sequences of the RTUs contained a HpaI processing tag. Cells were untreated (A) or treated with 100 U/ml IL-1β (B), 1 µg/ml forskolin (C), or 100 µM $Zn^{++}$ (D). The activities of individual RTUs were detected by assessing processed (HpaI-digested) reporter species using capillary electrophoresis (A to D, left panels); normalized values of the electrophretic peaks of individual RTU reporter species were calculated (A to D, middle panels); and the relative values of calibrating SV40 RTUs in each of the treatment conditions were assessed (A to D, right panels). Fold induction of each RTU reporter species was calculated by dividing the normalized value for the RTU reporter species in a given treatment group by the normalized value for the RTU reporter species in unstimulated cells (E).

Figure 14A:
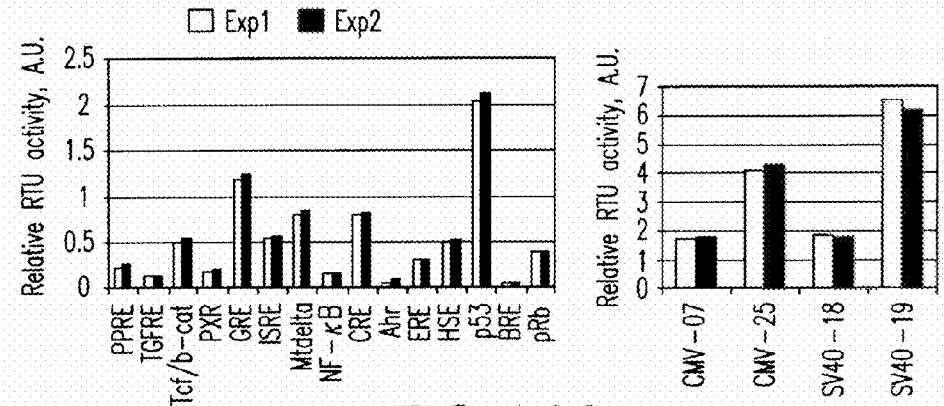
Figure 14B:
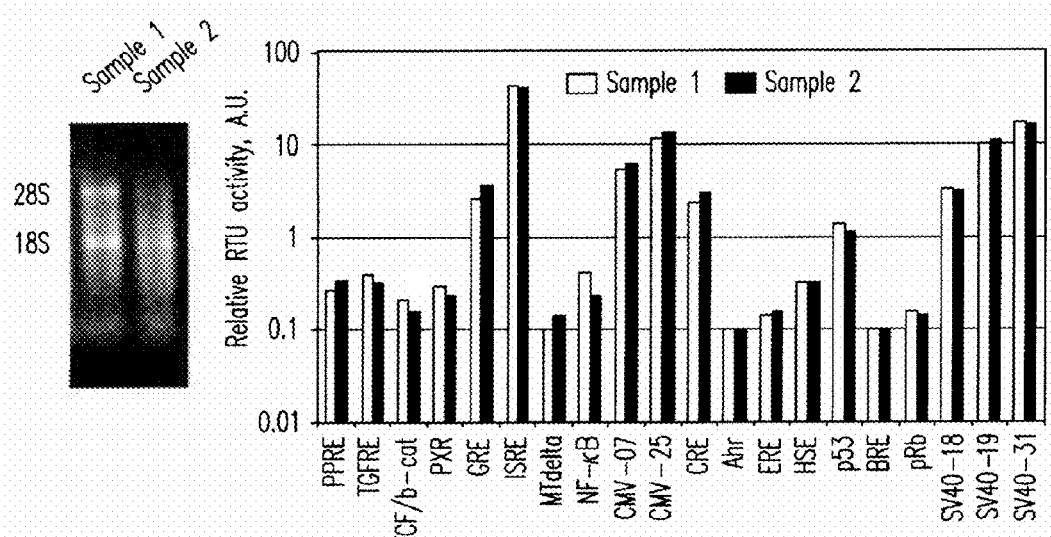
Figure 14C:
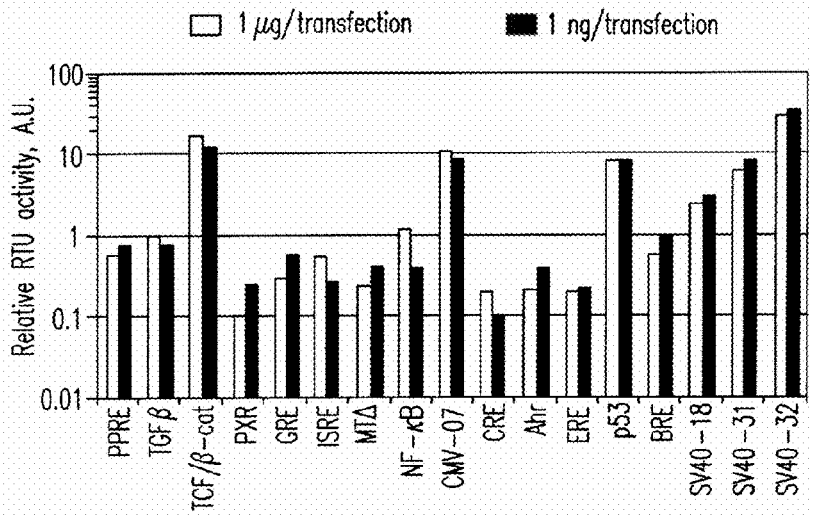

FIG. 14 provides representative results, as discussed in the examples, demonstrating that the present invention provides highly reproducible profiles of multiple transcription factor and/or multiple cis-regulatory elements activities. Basal activities of multiple transcription factors and cis-regulatory elements were assessed in HCT116 cells in two independent individual experiments (A). Basal transcription factor and cis-regulatory element activity profiles in basal 239 cells were assessed in samples having a broad variation in the quality of isolated reporter RNA (B). Basal transcription factor and cis-regulatory element activity profiles were determined in HepG2 cells transfected with one microgram or with one nanogram of a reporter RTUs (C).

Figure 15:
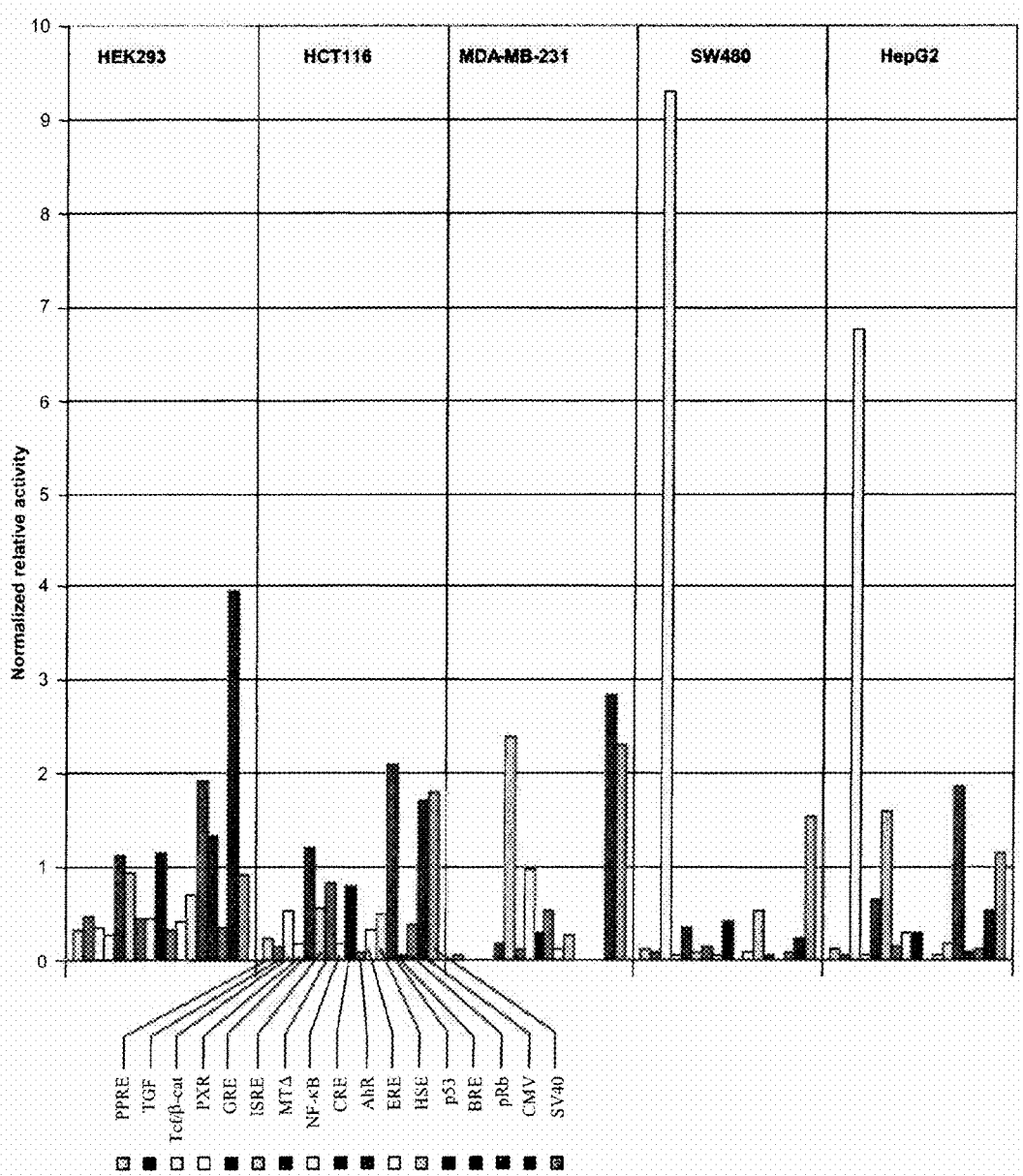

FIG. 15 provides basal profiles of activities of multiple transcription factors using fifteen RTUs in five human cancer cell lines (HEK293, HCT116, MDA-MB-231, SW480, and HepG2).

Figure 16:
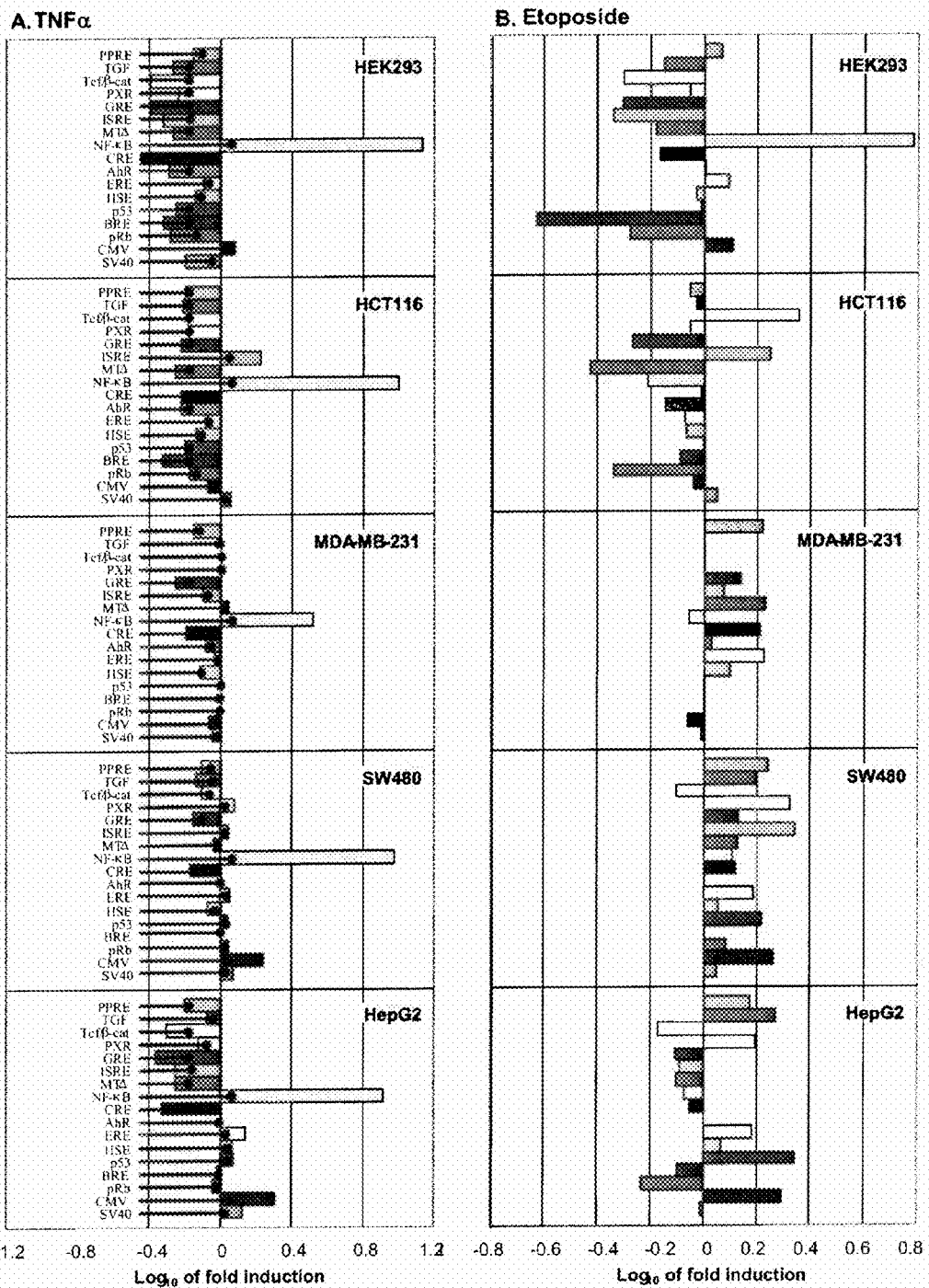

FIG. 16 provides transcription factor activity profiles occurring upon treatment of cancer cell lines with anti-cancer drugs TNFα (A) or etoposide (B).

Figure 17:
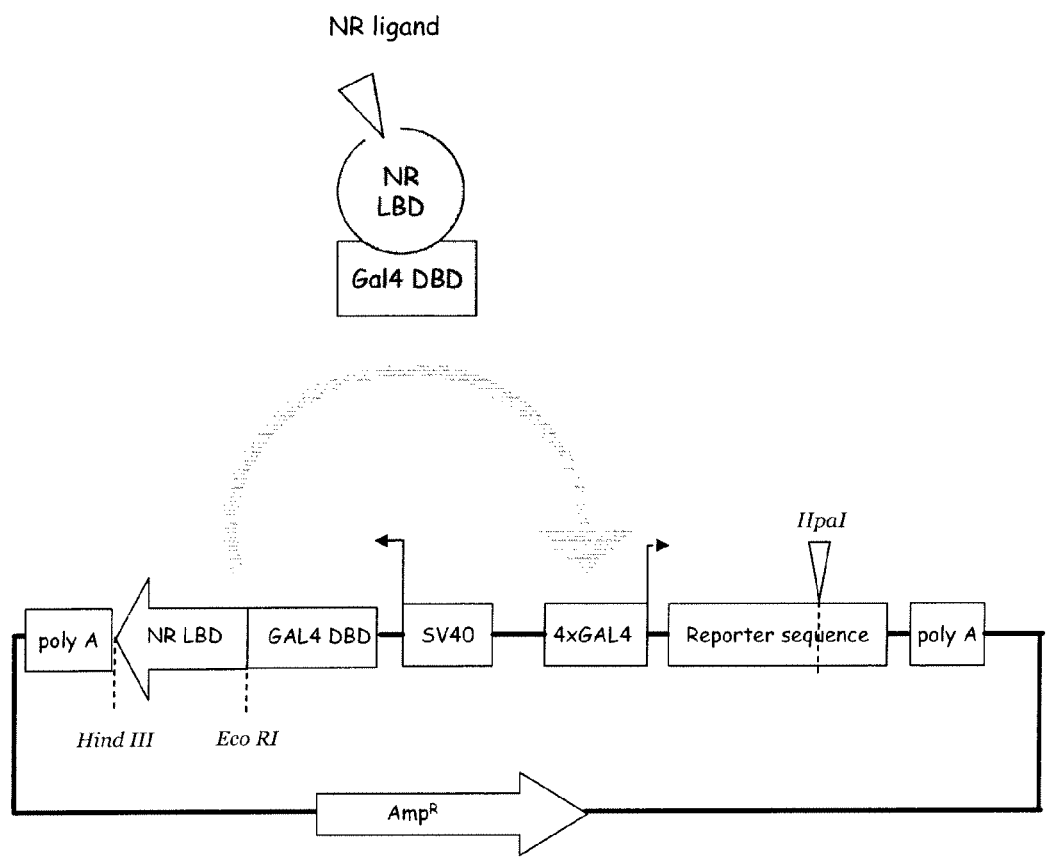

FIG. 17 provides a non-limiting schematic of an RTU for assessing nuclear receptor (NR) ligands.

Figure 18:
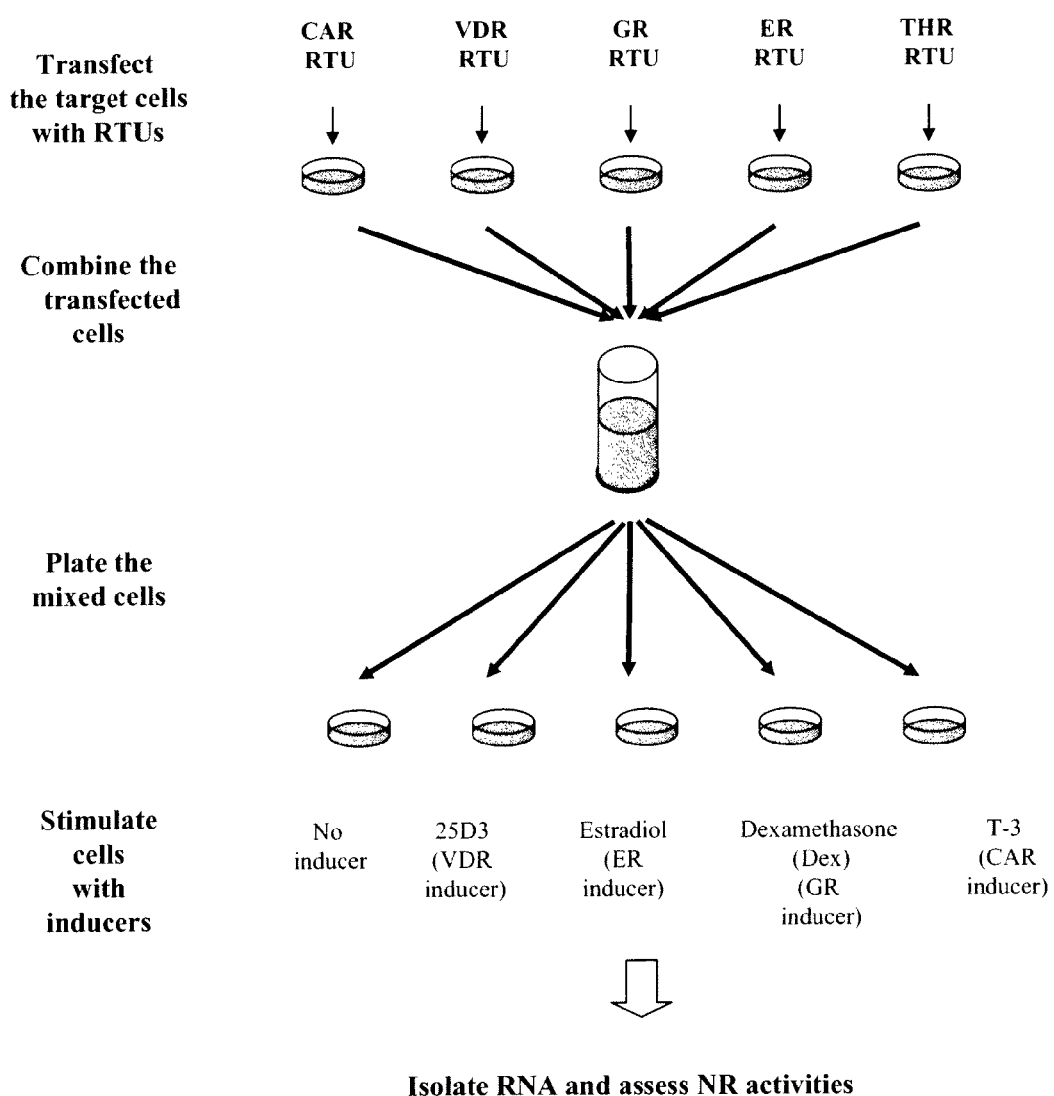

FIG. 18 provides a non-limiting schematic of a method of profiling NR RTU activities in a cell line.

Figure 19A:
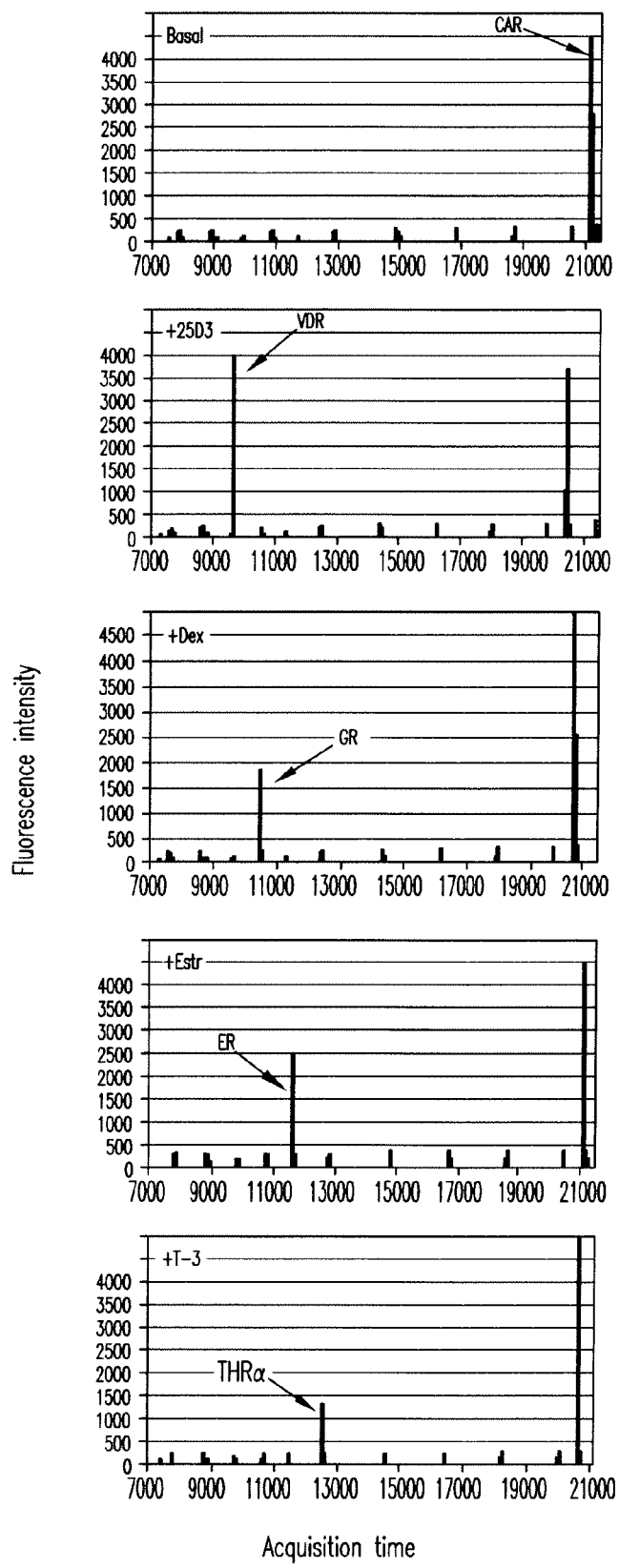

FIG. 19 provides results of an exemplary assessment of NR ligands in HEK293 cells. Cells comprising an NR RTU library were treated with an THR ligand (3,3',5-Triiodo-L-thyronine (T3)), an VDR ligand (25-dihydroxyvitamin D3 (25D3)), an ER ligand (estradiol (Estr)), an GR ligand (dexamethasone (Dex)) or left untreated (Basal).

Figure 20:
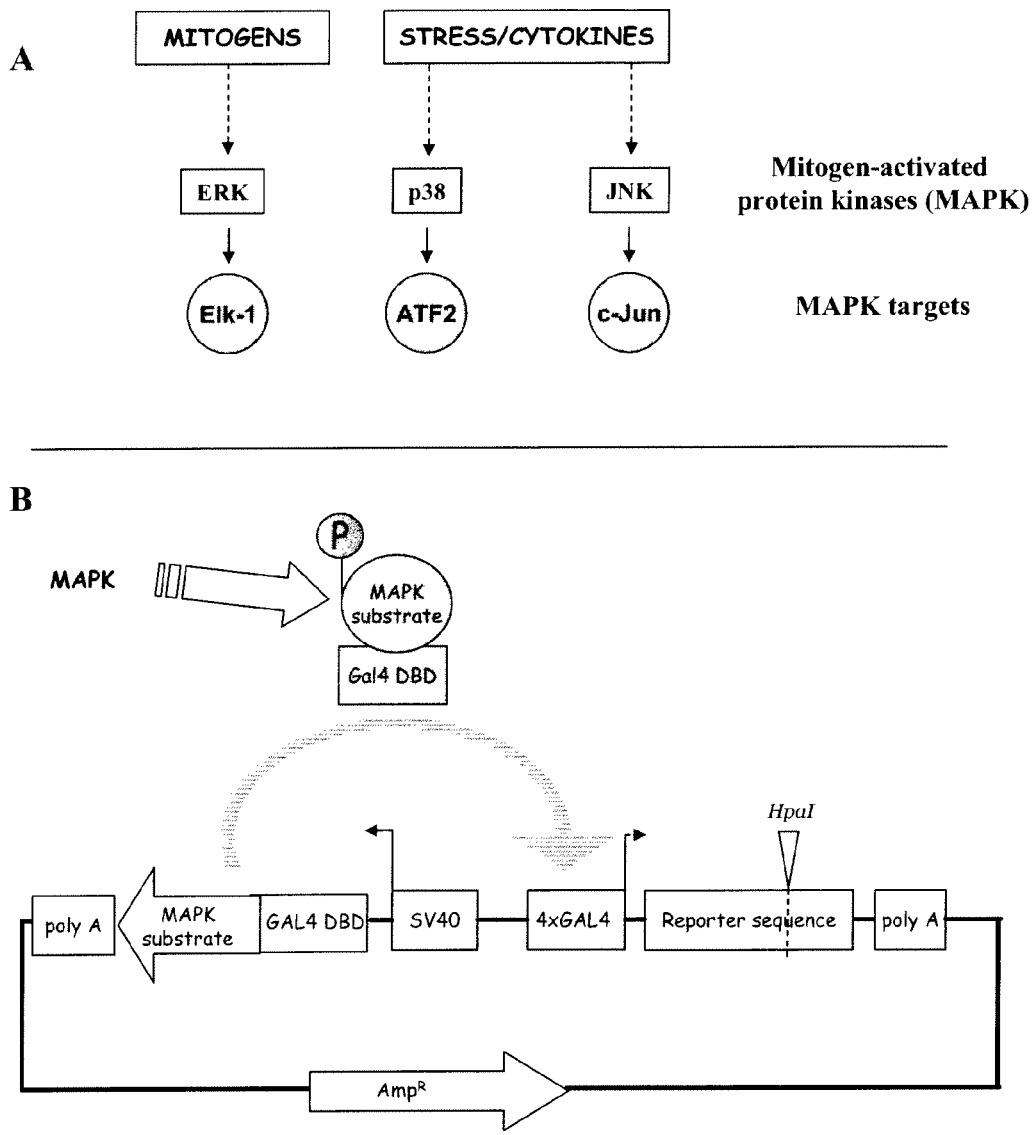

FIG. 20 provides diagrams of three major MAPK signaling pathways (A) and an exemplary RTU useful in determining activities of the MAPK signaling pathways (B).

Figure 21:
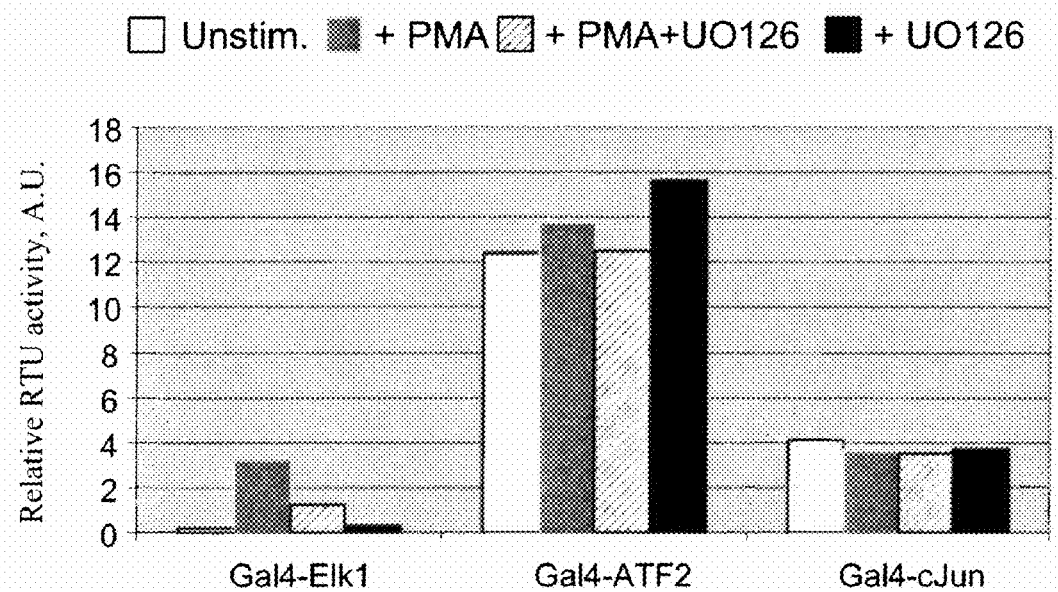

FIG. 21 provides results of an exemplary assessment of a chemical inhibitor of ERK MAPK signaling pathway (UO126) in HEK293 cells comprising RTUs useful for examining activities of MAPK pathways.

Figure 22:
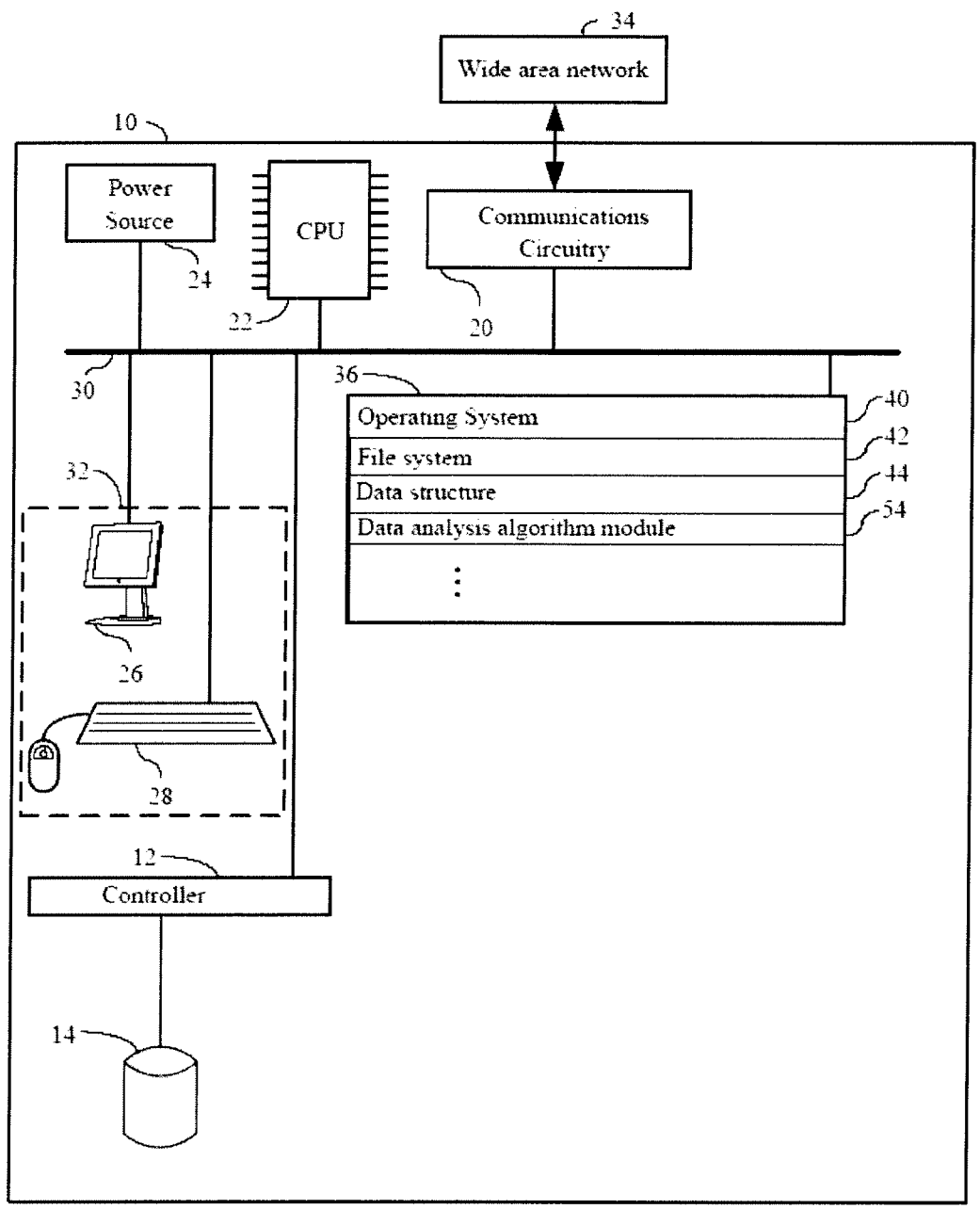

FIG. 22 illustrate a computer system in accordance with an embodiment of the present invention.

5. DETAILED DESCRIPTION

The present inventions now will be described more fully hereinafter with reference to the accompanying examples, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The article "a" and "an" are used herein to refer to one or more than one (i.e., to at least one) of the grammatical object of the article. By way of example, "an element" means one or more than one element.

5.1. Overview

The present invention provides compositions, methods and kits that enable the profiling of activities of multiple trans-acting factors and/or cis-regulatory elements in parallel. A component of this invention is a reporter transcription unit (RTU) which comprises a reporter sequence and a cis-regulatory element which modulates the level of the reporter sequence expression. RTU expression is assessed by determining the level of reporter species (i.e., RNA transcripts) of the reporter sequences. The advantage of this approach is that it permits multiple trans-acting factors or cis-regulatory elements to be assessed in parallel. To do so, individual RTUs are assembled into a population, wherein individual RTUs have distinguishable reporter sequences. When the populations of RTUs are delivered to biological systems, transcription of individual RTUs reflects, with high fidelity, the activities of the corresponding trans-acting factors.

5.2. Compositions

In one aspect, compositions are provided comprising a population of polynucleotides, each polynucleotide comprising a DNA construct comprising a reporter sequence having a processing tag whose position distinguishes various reporter sequences from one another within the population. In certain embodiments, the DNA constructs comprise a reporter transcription unit (RTU).

5.2.1. RTUs

As used herein, a "reporter transcription unit" or "RTU" comprises a cis-regulatory element operably linked to a reporter sequence, wherein the activity of the cis-regulatory element is modulated in the presence of a corresponding trans-acting factor or factors.

Cis-regulatory elements comprise polynucleotides that influence the abundance of RNA transcripts. Cis-regulatory elements can include, for example, any sequence that modulates the stability, maturation, or transcription of the reporter sequence. Such cis-regulatory sequences include, but are not limited to, promoters, enhancers, RNA stability signals, polyadenylation signals, and any other cis-elements that affect the level of RNA transcript.

The cis-regulatory element is operably linked to reporter sequences such that the abundance of the reporter transcripts is determined by the cis-regulatory sequence being evaluated. Cis-regulatory elements comprising promoters are usually placed upstream of and in the proximity of the reporter sequence. However, depending on the nature of the cis-regulatory element being evaluated, the element can be placed upstream, downstream, or inside of the reporter sequence. For example, enhancer sequences, which can act regardless of their orientation, can be located upstream, downstream, or inside of the regulated sequence, and, frequently, at far distances from the sequence being regulated. Another example of cis-regulatory elements include regulatory sequences that control RNA stability. These elements can be found inside of the transcribed sequence, within the coding region, within introns, or within the 3' or 5' untranslated regions. Cis-regulatory elements further include sequences that regulate transcript splicing and polyadenylation. Such elements can be located within the transcribed regions of the reporter sequence.

It is recognized, in embodiments where the cis-regulatory element does not comprise a transcriptional regulatory region or a promoter, the RTU will be operably linked to a transcriptionally regulatory region that is active in the biological system of interest. In specific embodiments, the transcriptional regulatory region is constitutively active or is inducible.

The cis-regulatory element employed in the RTU may be native/analogous or heterologous to the biological system or to the reporter sequence. As used herein, "heterologous" in reference to a sequence is a sequence that originates from a foreign species, or, if from the same species, is substantially modified from its native form in composition and/or genomic locus by deliberate human intervention. In still other embodiments, the cis-regulatory element can be naturally occurring, a variant of a naturally occurring sequence, or a synthetic sequence.

In one embodiment, the cis-regulatory element employed in the RTU comprises a promoter. The promoter comprises two elements: a minimal polynucleotide sequence that facilitates recruitment of basal transcriptional machinery; and, one or more copies of sequences specifically recognized by a transcription factor. Such sequences can be either native or synthetic. The number of binding sites present for a given transcription factor of interest will vary as will the distance between the binding sites. In specific embodiments, the binding sites are in tandem. One of skill will recognize the appropriate number of binding sites that are needed to assay for the desired activity. For example, 1, 2, 3, 4, 5, 6, 7, 8, 9, 10, 11, 12, 13, 14, 15, or greater binding sites may be present in the promoter. As discussed below, binding sites are known in the art. See, for example, Tables 1-3, which provide non-limiting examples of transcription factor binding sites. A given promoter may further comprise one or more binding sites from distinct transcription factors. Minimal polynucleotide sequences that facilitate recruitment of basal transcriptional machinery are also known in the art.

TABLE 1

Non-limiting list of representative transcription factors and their DNA binding sites.

| Transcription factor | DNA binding site* | SEQ ID NO: |
|---|---|---|
| C/EBP | TGCAGATTGCGCAATCTGCA | 1 |
| CREB | AGAGATTGCCTGACGTCAGAGAGCTAG | 2 |
| E2F-1 | ATTTAAGTTTCGCGCCCTTTCTCAA | 3 |
| c-Myb | TACAGGCATAACGGTTCCGTAGTGA | 4 |
| Egr | CGCCCCCGC | 5 |
| AP 1 | CGCTTGATGACTCAGCCGGAA | 6 |
| AP-2 | GATCGAACTGACCGCCCGCGGCCCGT | 7 |
| Brn-3 | A/GCTCATTAAT/C | 8 |

TABLE 1-continued

Non-limiting list of representative
transcription factors and their DNA
binding sites.

| Transcription factor | DNA binding site* | SEQ ID NO: |
|---|---|---|
| ERE | GTCCAAAGTCAGGTCACAGTGACCTGATCAAGTT | 9 |
| Ets-1/PEA3 | GATCTCGAGCAGGAAGTTCGA | 10 |

*Nucleotides believed to be contacted by a bound transcription factor are shown in bold.

It is recognized that when the cis-regulatory element comprises a promoter, one of skill will recognize that while the RTU can comprise a native promoter (i.e., the minimal promoter sequence and transcription factor binding site occur together in nature), a heterologous promoter, for example, having a minimal promoter that is heterologous to the transcription factor binding site, may also be employed.

The distance between the minimal promoter sequence and the transcription factor binding sites may vary. For example, the minimal promoter sequence and the 3' most transcription factor binding site can be immediately adjacent or within 5, 10, 20, 50, 100, 150, 200, 250, 300, 350, 400, 450, 500, 550, 600, 650, 700, 800, 900, 1000 nucleotides or greater, so long as the promoter retains transcriptional activity.

The activity of the cis-regulatory element is modulated in the presence of its corresponding trans-acting factor (i.e., one or more trans-acting factors that regulates its activity). "Cis-regulatory element activity" is defined as the ability of a cis-regulatory element to modulate the level of transcription of a nucleotide sequence operably linked to the cis-regulatory element. In general, modulation of cis-regulatory element activity comprises any statistically significant increase or decrease in level of the RNA transcripts transcribed from the reporter sequence relative to an appropriate control. For example, modulation of cis-regulatory element activity comprises an increase or a decrease in the level of reporter species of the reporter sequence of at least 0.5%, 1%, 5%, 10%, 20%, 30%, 40%, 50%, 60%, 70%, 80%, 90%, 100%, 120%, 140%, 160%, 200% or greater relative to an appropriate control. Methods for detecting the activity of the cis-regulatory element are discussed elsewhere herein.

The cis-regulatory elements of the RTU are operably linked to the reporter sequence. "Operably linked," as used herein, means a functional linkage between two or more elements. For example, an operable linkage between a promoter and a reporter sequence is a functional link that enables expression of the reporter sequence. An operably linkage between an RNA stability element and a reporter construct is a functional linkage that allows the RNA stability element to modulate the stability of the reporter RNA. Operably linked elements may be contiguous or non-contiguous.

As used herein, a "reporter sequence" comprises a polynucleotide sequence wherein the sequence comprises a processing tag. Thus, a processing tag is located in the reporter sequence, that is, the processing tag can be located within the non-processing tag portion of the reporter sequence or can be located adjacent to the non-processing tag portion of the reporter sequence. A detailed description of this tag is provided elsewhere herein. The reporter sequence may comprise any polynucleotide. The reporter sequence may be native/analogous or heterologous to the biological system or the cis-regulatory element. The reporter sequence may also be a naturally occurring sequence, a variant of the naturally occurring sequence, or a synthetic sequence. For example, the reporter sequence can comprise a gene, a coding region, an exon, or an intron, or any fragment of each of these structures. Alternatively, the reporter sequence can comprise a synthetic DNA oligonucleotide. In addition, the reporter sequence may or may not encode a polypeptide. The reporter sequence may also comprise signals for posttranscriptional modification by cellular machinery, such as acceptor and donor splice sites, polyadenylation signals, and transcription termination signals.

In specific embodiments, the reporter sequence is selected to fulfill one or more of the following criteria: (1) to minimize background, reporter sequences may not be present in the genome of the host cell; (2) to eliminate spurious transcription, the reporter sequence can lack binding sites for endogenous trans-acting factors found in the biological system of interest; (3) the reporter sequence should be efficiently transcribed into RNA by transcription machinery of the biological system of interest; and, (4) the reporter sequence should not have elements that prematurely terminate transcription. Thus, in designing a reporter sequence, one of skill will recognize that some sequence modifications known to enhance expression and/or stability in a biological system find use when designing a reporter sequence. For example, the reporter sequence can comprise a polyadenylation signal and/or a transcriptional stop signal (terminator)that terminates transcription. Additional modifications to the reporter sequences can include, for example, elimination of sequences encoding spurious polyadenylation signals, exon-intron splice site signals, transposon-like repeats, and other such well-characterized sequences that may be deleterious to gene expression. The G-C content of the sequence may be adjusted to levels average for a given biological system, as calculated by reference to known genes expressed in the biological system. In addition, the reporter sequence can be designed as to avoid predicted hairpin secondary mRNA structures.

A reporter sequence can be of any length. One of skill will recognize the appropriate length for the methods of detection desired. In specific embodiments, the reporter sequence is 15 nt, 35 nt, 55 nt, 75 nt, 95 nt, 110 nt, 125 nt, 155 nt, 175 nt, 200 nt, 250 nt, 275 nt, 300 nt, 350 nt, 400 nt, 450 nt, 500 nt, 550 nt, 600 nt, 650 nt, 700 nt, 750 nt, 800 nt, 850 nt, 900 nt, 950 nt, 1000 nt, 1050 nt, 1100 nt, 1150 nt, 1200 nt, 1300 nt, 1400 nt, 1500 nt, 1600 nt, 1700 nt, 2000 nt, 2500 nt, 3000 nt, or greater.

In preparing the RTU, the various fragments may be manipulated, so as to provide for the sequences in the proper orientation in the proper reading frame (when appropriate), and to ensure the cis-regulatory element and the reporter sequences are operably linked. Toward this end, adapters or linkers may be employed to join the fragments or other manipulations may be involved to provide for convenient restriction sites, removal of superfluous polynucleotide sequences, removal of restriction sites, or the like. For this purpose, in vitro mutagenesis, primer repair, restriction, annealing, resubstitutions, e.g., transitions and transversions, may be involved.

5.2.2. Populations of Polynucleotides

A population of isolated polynucleotides is provided which comprise DNA constructs having reporter sequences, wherein each of the reporter sequences comprise a unique processing tag, wherein the position of the processing tag is different in each of the DNA constructs in the population. As discussed in further detail below, in specific embodiments, the reporter sequences in the population are substantially identical to one another.

In other embodiments, a population of isolated polynucleotides comprising RTUs having a cis-regulatory element operably linked to a reporter sequence are provided. The RTUs vary within the population of polynucleotides such that the same cis-regulatory element is employed with the same reporter sequence in a given RTU in the population. This relationship between the reporter sequence and the cis-regulatory element allows one to correlate the activity of a given cis-regulatory element with the level of transcribed reporter species. In addition, each RTU in the population comprises a unique processing tag in the reporter sequence, wherein the processing tag can distinguish a reporter species of each of the RTUs in the population. For example, the processing tag can be inserted into the reporter sequence at a different position in each of the RTUs in the population. As another example, the processing tags can vary in nucleotide number or type of nucleotide and be positioned in different locations in the reporter sequences of the RTUs. In specific embodiments, each of the RTUs within a given population comprises substantially identical or fully identical reporter sequences outside of the processing tag.

As used herein by "processing tag" is intended any nucleotide or any combination of nucleotides that permit the reporter species, or a complementary detection probe, to be processed at a defined site, or multiple defined sites, thereby providing a means to distinguish the processed reporter species of each reporter sequence in the population. By "processing" is intended any method that allows the reporter species, or a complementary detection probe, to be processed at the position defined by the processing tag, thereby generating a distinguishable reporter species, or a distinguishable complementary detection probe. Representative processing tags include, but are not limited to, a unique thymine, adenine, cytosine, or guanine nucleotide residue; an endonuclease recognition site; and, a common primer sequence. Methods for processing these tags and thereby distinguishing the reporter sequences are discussed in detail elsewhere herein. The "unique" processing tag employed in the population may be a common tag (i.e., the tag is identical in each of the reporter sequences in the population and varies only in its position in the reporter sequence). Alternatively, a "unique" processing tag employed in the population can be non-identical to the other tags in the population. A "non-identical" processing tag encompasses different processing tags which fall within the same class of processing tags (i.e., different restriction enzyme recognition sequences, different primer sequence, etc.). A non-identical processing tag also encompasses different processing tags falling into distinct classes of processing tags. Such distinct classes of processing tags are discussed elsewhere herein. It is further recognized that multiple, unique, processing tags may be present in a single RTU. Accordingly, a single RTU can have 1, 2, 3, 4, 5, 6, 7, 10 or more unique processing tags such that each of the multiple processing tags in the given RTU are identical to one another or, alternatively, one or more of the tags of the RTU can be non-identical to one another.

In certain embodiments, upon processing, reporter species of the individual reporter sequences produce distinguishable fragments. As discussed elsewhere herein, current separation methods make it is possible to separate DNA and RNA species with very high precision. Therefore, in specific embodiments, a large number of distinguishable processing products of reporter species can be prepared from a comparatively short common reporter sequence. For example, by varying the position of the processing tag within a common, 2,000 bp-long, reporter sequence with the step of one base pair, it is possible to produce 2,000 distinguishable reporter species. Accordingly, the relative position of the common processing tag can vary in the population of reporter sequences by as little as 1, 2, 5, 10, 25, 50, 95, 100, 150, 200 nucleotides or greater. As the human genome contains an estimated 1,000 to 2,000 transcription factors, it is principally possible to produce a population of RTUs that enable the profiling all human transcription factors. Accordingly, the activities of more than 2, 10, 50, 100, 500, 1000, 1500, 2000, 2500 or greater cis-regulatory elements and/or trans-acting factors can be determined.

In certain embodiments, reporter species of the individual reporter sequences are distinguished by contacting the reporter species with one or more detection probes, and, optionally, processing the heteroduplexes of detection probes and reporter species. Typically, a given detection probe (or segment or segments therein) forms a duplex with an complementary sequence in a particular reporter species that encompasses or overlaps the processing tag. In some embodiments, a given detection probe (or segment or segments therein) forms a duplex with an complementary sequence in a particular reporter species that encompasses or overlaps both the processing tag and a portion (or portions) of the reporter sequence flanking the processing tag. In some embodiments, a detection probe is complementary to portions of the reporter sequence that flank both sides of the processing tag. A dectection probes typically comprises an oligonucleotide, and can further comprise one or more labels, quenchers, and the like.

By "population" is intended a group or collection that comprises two or more (e.g., 2, 3, 4, 5, 6, 7, 8, 9, 10, 15, 20, 25, 30, 50, 75, 100, 125, 150, 175, 200, 225, 250, or greater) distinct polynucleotides.

In specific embodiments, the reporter sequences within a population of RTUs are transcribed with comparable efficiencies. By "comparable transcriptional efficiency" is intended each reporter sequence (including one or more processing tags) is expressed with approximately equal efficiencies when the sequences are under the control of an identical transcriptional regulatory element. Comparable transcriptional efficiency includes a difference in expression levels of less than about 0.1%, 1%, 5%, 10%, 15%, 20%, 25%, 30%, 35%, 40%, 45%, or 50%.

By "substantially identical" reporter sequence is intended, polynucleotides that differ by 10, 9, 8, 7, 6, 5, 4, 3, 2, or even 1 nucleotide base substitution and/or internal nucleotide addition and/or deletion. Alternatively, "substantially identical" reporter sequences can exhibit sequence identity of about 90%, 91%, 92%, 93%, 94%, 95%, 96%, 97%, 98%, or 99%. Methods for determining percent identity are disclosed elsewhere herein. In specific methods and compositions, the substantially identical reporter sequences in the population differ by less than 5, differ by less than 2, or differ by 1 nucleotide base substitution and/or internal nucleotide addition and/or deletion.

Typically, the difference between "substantially identical" reporter sequences is due to the processing tag in the reporter sequences. For example, in certain embodiments, the reporter sequences, outside of the processing tags, are identical between any two RTUs in a population. However, in certain embodiments, "substantially identical" reporter sequences can differ by 10, 9, 8, 7, 6, 5, 4, 3, 2, or 1 nucleotide base substitution and/or internal nucleotide addition and/or deletion, or, alternatively, can exhibit sequence identity of about 90%, 91%, 92%, 93%, 94%, 95%, 96%, 97%, 98%, or 99%, wherein the difference in reporter sequences does not include a processing tag.

In some embodiments, a RTU population is provided wherein the reporter sequence for each RTU comprises a fragment of cDNA of a secreted alkaline phosphatase (SEAP) sequence and a HpaI restriction site processing tag.

In some embodiments, the RTU further comprises primer sequences that flank a portion of the reporter sequence on both the 5' end (i.e., 5' primer sequence) and on the 3' end (i.e., 3' primer sequence). In one embodiment, the primer sequences flank the reporter sequence in its entirety. However, it is recognized that the primer sequences need not flank the entire reporter sequence, but rather the 5' and 3' primers can be located such that any appropriate region of the reporter sequence can be amplified. In specific compositions and methods, in a given population, the primer sequences employed in each RTU are identical. This allows the reporter sequence transcription products from each RTU in the population to be amplified under identical PCR amplification conditions. The 5' and 3' primers can comprise any polynucleotide that is effectively employed in PCR. Such sequences are known in the art. See, for example, Saiki et al. (1986) *Science* 230:1350-54, Sambrook et al. (1989) *Molecular Cloning: A Laboratory Manual*, $2^{nd}$ edition, Cold Harbor Laboratory Press, New York and U.S. Pat. No. 6,653,079, all of which are herein incorporated by reference in their entireties.

The compositions and methods of the invention are capable of detecting the activity of trans-acting factors. By "trans-acting factor" is intended any factor that modulates the activity of the cis-regulatory element in trans, and thereby modulates the level of the reporter species in the biological system. The trans-acting factor can modulate the activity of the cis-regulatory element either directly or indirectly. It is recognized that cis-regulatory elements can be regulated by multiple trans-acting factors. Accordingly, an RTU of this class can be used for assessing the more complex activity of the pathway that modulates the activity of the cis-regulatory element. Such trans-acting factors include, but are not limited to, a transcription factor, a factor that regulates RNA stability, a nuclear receptor, an activator of transcription, a repressor of transcription, a chimeric protein comprising a DNA binding domain fused in frame to a heterologous transactivation domain, a factor regulating RNA stability, and a factor regulating RNA maturation. In addition, the activity of the trans-acting factor may be modulated by a variety of stimuli including, but not limited to, an inflammatory stimuli, a stress stimuli, a development or a cell differentiation signal, an oncogenesis signal, a toxin, a xenobiotic, or, a drug.

The activity of any trans-acting factor can be assayed, so long as the corresponding cis-regulatory element is present in the RTU. In specific embodiments, the trans-acting factor is a transcription factor. In other embodiments, the trans-acting factor is a eukaryotic transcription factor. Several classes of such transcription factors exist including, for example, homeodomain proteins, zinc-finger proteins ($C_2H_2$ zinc-fingers; $C_4$ zinc fingers; $C_6$ zinc fingers), winged helix (forkhead) proteins; leucine-zipper proteins, and helix-loop-helix proteins.

In specific methods and compositions, the activity of one or more inflammatory and/or stress-responsive trans-acting factor is monitored. By "inflammatory or stress-responsive trans-acting factor" is intended a trans-acting factor that modulates the level of reporter species under conditions of stress or an inflammatory response. In specific embodiments, such transcription factors include, but are not limited to, NF-κB, NF-AT, AP-1, C/EBPs, Ets-1, Elk, GR, PPARs, c-Rel, ATF2, c-Fos, CREB-1, or RXR.

In other methods and compositions, the activity of one or more proliferating tumor-related trans-acting factor is monitored. By "proliferating tumor-related trans-acting factor" is intended a trans-acting factor whose activity modulates the cell cycle, cell proliferation, and/or apoptosis. Dysregulated signal transduction is a hallmark of cancer. During the multistage process of tumorigenesis, cells accumulate changes that ultimately lead to an aberrant regulation of signaling pathways. The aberrant regulation of the signal transduction network leads to constitutive activation of transcription factors controlling the expression of numerous genes involved in cell proliferation, apoptosis, and differentiation. Some of the trans-acting factors critically involved in tumorigenesis have been well characterized. Such factors include, but are not limited to, the retinoblastoma (Rb) tumor suppressor protein plays a central role in suppressing tumorigenesis. The key regulatory target of Rb is the transcription factor E2F, a central regulator of transition into S-phase and initiation of DNA replication. Modulation of the Rb/E2F pathway has been found in virtually all human cancers (Nevins (2001) *Hum Mol Genet* 10(7):699-703). Another regulator of tumorigenesis is the transcription factor p53, the product of a TP53 gene. p53 serves as a tumor-suppressor that guards against genomic instability and oncogene expression by inducing both cell cycle arrest and apoptosis. p53 is potentially activated in response to many chemotherapeutic drugs and promotes cell death through the regulation of specific pro-apoptotic genes. The importance of p53 in preventing tumor development is illustrated by the fact that it is inactivated in roughly 50% of all human cancers (Hollstein et al. (1991) *Science* 253(5015): 49-53; O'Connor et al. (1997) *Cancer Res.* 57:4285-4300; reviewed in Levine (1997) *Cell* 88(3):323-31; Hickman et al. (2002) *Curr. Opin. Genet. Dev.* 12(1):60-6; Vogelstein and Kinzler (2004) *Nat. Med.* 10(8):789-99). The proto-oncogene c-Myc is a transcription factor that plays a key role in growth control and cell cycle progression by stimulating or repressing the expression of key cell cycle regulators. Deregulated expression of Myc induces cellular growth and apoptosis and inhibits differentiation (Lutz et al. (2002) *Biochim. Biophys. Acta* 1602(1):61-71). Activating mutations or amplification of the c-myc allele are frequently found in many human cancers, indicating a pivotal role of c-Myc in tumorigenesis (Nesbit et al. (1999) *Oncogene* 18(19):3004-16). The proto-oncogene β-catenin, a target of the Wnt pathway, is involved in the control of cell adhesion and cell polarity. β-catenin is a transcriptional co-activator that activates transcription upon association with DNA-binding proteins of the TCF/LEF family. The mutations that activate β-catenin (either by inactivation of the negative regulators of β-catenin stability, such as tumor suppressor APC, or by constitutive activation of β-catenin itself), result in constitutive expression of β-catenin/TCF-dependent genes associated with cancer, such as cyclin D1, c-Myc, cyclooxygenase (COX)-2, etc. The activation of β-catenin/TCF-mediated gene transcription is a common event in colorectal cancer and melanomas (Korinek et al. (1997) *Science* 275(5307):1784-7; Morin et al. (1997) *Science* 275(5307):1787-90; Rubinfeld et al. (1997) *Science* 275 (5307):1790-2; reviewed in Fodde et al. (2001) *Nature Rev Cancer* 1(1):55-67; Polakis (2000) *Genes Dev* 14(15):1837-51; Vogelstein and Kinzler (2004) *Nat Med* 10(8):789-99). The transcription factor NF-κB is a pivotal regulator of the inflammatory responses to pathogens and stress. Recent developments have revealed an important role for NF-κB in cancer. Activation of the NF-κB pathway contributes to tumorigenesis by activating the expression of proteins involved in cell-cycle control, e.g., c-Myc and cyclin D1, and in suppressing apoptosis in cancer cells (Baldwin, (2001) *J Clin Invest*

107:241-246). Constitutive activation of NF-κB is found in many human cancers, including childhood acute lymphoblastic leukemia (ALL) (Kordes et al. (2000) *Leukemia* 14(3): 399-402), Hodgkin's disease tumor cells (Bargou et al. (1997) *J Clin Invest* 100(12):2961-9), and in primary breast tumors (Nakshatri et al. (1997) *Mol Cell Biol.* 17(7):3629-39; Romieu-Mourez et al. (2001) *Cancer Res* 61(9):3810-8). The cellular progenitor of the retroviral v-jun oncogene, the c-jun protooncogene, encodes a major component of the transcription factor AP-1, which represents a collection of dimers consisting of Jun, Fos, or ATF protein family members. Gene regulation by AP-1 is important for cell proliferation and differentiation, and constitutive AP-1 activation can lead to tumor formation (Vogt (2001) *Oncogene* 20:2365-2377). Distinct AP-1-regulated keratin genes are consistently overexpressed in various carcinomas (Oshima et al. (1996) *Metastasis Rev.* 15, 445-471), and the transactivation function of AP-1 is required for tumor promotion in epidermal cells (Young et al. (1999) *Proc. Natl. Acad. Sci. USA* 96:9827-9832). The c-fos protooncogene is required for malignant progression of skin tumors (Saez et al. (1995) *Cell* 82:721-732). The transcription factor cyclic AMP response element binding protein (CREB) activates transcription of cAMP response element (CRE)-containing promoters following an elevation of intracellular cAMP. The expression and the transcription activity of CREB and the highly related transcription factors ATF-1 are upregulated in metastatic melanoma cells, while a dominant-negative form of CREB inhibits their tumorigenicity and metastatic potential (Jean and Bar-Eli (2001) *Crit. Rev. Immunol.* 21(1-3):275-86). These few examples serve to illustrate that aberrant regulation of trans-acting factor activities lies at the heart of cancer initiation and progression. A long list of trans-acting factors implicated in tumorigenesis also includes other transcription factors such as Gli (Ruiz i Altaba et al. (2002) *Nat. Rev. Cancer* 2(5):361-72), Forkhead/HNF-3 (Hromas and Costa (1995) *Crit. Rev. Oncol. Hematol.* 20(1-2):129-40; Accili and Arden (2004) *Cell* 117(4):421-6), and certain SMADs (Piek and Roberts (2001) *Adv. Cancer Res.* 83:1-54). Additionally, several transcription factors (including p53) are activated in response to chemotherapy and radiation. For example, NF-κB is potently activated in cancer cells following exposure to cancer therapies and this response controls the mechanisms known as "inducible chemoresistance" (Baldwin (2001) *J. Clin. Invest.* 107:241-246). Tables 1-3 provide a non-limiting list of representative transcription factors and representative DNA binding sites.

As discussed above, variants of the cis-regulatory elements can also be employed in the invention. By "variants" is intended substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. Variant polynucleotides (i.e., variant cis-regulatory elements) encompassed by the present invention are biologically active, that is they continue to possess the desired biological activity of the native polynucleotide, that is, they retain the ability to modulate the level of the transcripts from the reporter sequence. For example, a biologically active promoter sequences will retain the ability to modulate transcriptional activity, bind transcription factors, or recruit basal transcriptional machinery. Biologically active RNA stability elements will retain the ability to influence the stability of the RNA transcript.

As suggested in Tables 1 and 3, for instance, certain transcription factors can bind to variant cis-regulatory elements. Thus, in certain embodiments, different RTUs in a population can have non-identical cis-regulatory sequences operably linked to an identical reporter sequence/processing tag combination. This is useful, for example, where activity of a given transcription factor, known to bind to two different cis-regulatory sequences, is to be assessed. Generally, such redundancy can be introduced into a RTU population to the extent that the ability to distinguish between activities of different transcription factors is maintained.

As used herein, a "native" polynucleotide or polypeptide comprises a naturally occurring nucleotide sequence or amino acid sequence, respectively. For polynucleotides, naturally occurring variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein. A biologically active variant of a polynucleotide employed in the methods of the invention may differ from that protein by as few as 1-15 nucleotide bases, as few as 1-10, such as 6-10, as few as 5, as few as 4, 3, 2, or even 1 nucleotide bases.

Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein.

Variant polynucleotides also encompass sequences derived from a mutagenic and recombinogenic procedure such as DNA shuffling. With such a procedure, one or more different polynucleotide sequence can be manipulated to create a new minimal polynucleotide sequence that facilitate recruitment of basal transcriptional machinery or is a binding site for a transcription factor. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272: 336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence. As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Sequence relationships can be analyzed and described using computer-implemented algorithms. The sequence relationship between two or more polynucleotides, or two or more polypeptides can be determined by determining the best alignment of the sequences, and scoring the matches and the gaps in the alignment, which yields the percent sequence identity, and the percent sequence similarity. Polynucleotide relationships can also be described based on a comparison of the polypeptides each encodes. Many programs and algorithms for the comparison and analysis of sequences are well known in the art.

Unless otherwise stated, sequence identity/similarity values provided herein refer to the value obtained using GAP Version 10 (GCG, Accelrys, San Diego, Calif.) using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix (Henikoff and Henikoff (1989) *Proc. Natl. Acad. Sci USA* 89:10915); or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

As used herein, "sequence identity" or "identity" in the context of two polynucleotides or polypeptide sequences makes reference to the residues in the two sequences that are the same when aligned for maximum correspondence over a specified comparison window. As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The population of polynucleotides comprising the RTUs can further comprise at least one calibrating RTU. As discussed in more detail elsewhere herein, in specific embodiments, the calibrating RTUs in the population can be used when determining a trans-acting factor activity profile. As used herein, a "calibrating RTU" comprises a polynucleotide having a transcriptional regulatory region operably linked to a reporter sequence. A transcriptional regulatory region comprises a polynucleotide sequence that is capable of directing transcription in cell types and at the developmental stages in which the RTU population is being evaluated. Because the calibrating RTU and the population of RTUs are detected under the same experimental conditions and amplified with the same primer pair, the assessment of the transcription products from the calibrating RTUs provides an internal control for the integrity of the RNA, the possible presence of PCR inhibitors, and the efficacy of PCR amplification. The calibrating RTU can also be used to provide the reference signal for quantitative assessment.

Examples of constitutive transcriptional regulatory regions include the regulatory regions of viral genes and/or housekeeping genes. Such regulatory regions include the beta actin promoter (Miyamoto et al. (1987) *Nucleic Acid Research* 15:9095 and GENBANK™ Acc. No. Y00474); beta-2-microglobulin promoter (GENBANK™ Acc. No. AF092744, *Homo sapiens* and GENBANK™ Acc. No. AY04812, *Mus musculus*); the glyceraldehydes-3-phosphate dehydrogenase promoter; the viral CMV promoter; the bactin promoter; and the viral SV40 promoter.

A given population can comprise multiple calibrating RTUs. When multiple calibrating RTUs are employed, the same constitutive transcriptional regulatory region is employed with the same reporter sequence in the population. A given population of RTUs can comprise 1, 2, 3, 4, 5, 6, 7, 8, 9, 10, or greater calibrating RTUs.

5.2.3. Vectors and Biological Systems

In one aspect, vectors and biological systems are provided comprising a population of polynucleotides described in the preceding subsections.

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms and double-stranded forms.

The polynucleotide comprising the RTU or the DNA construct comprising the reporter sequence can be provided in vectors for the introduction of the sequence into a biological system of interest. "Vector" refers to a nucleic acid molecule capable of transporting another nucleic acid to which it has been linked. Such vectors include, for example, a plasmid, a phagemid, a circular double-stranded DNA loop into which additional DNA segments can be ligated, or a viral vector, where additional DNA segments can be ligated into the viral genome. The vectors are useful for autonomous replication in a host cell or may be integrated into the genome of a host cell upon introduction into the host cell, and thereby are replicated along with the host genome (e.g., nonepisomal mammalian vectors). In general, expression vectors of utility in recombinant DNA techniques are often in the form of plasmids (vectors). However, the invention is intended to include such other forms of expression vectors, such as viral vectors (e.g., replication-defective retroviruses, lentiviral vectors, adenoviruses, and adeno-associated viruses), that serve equivalent functions. The vectors may additionally contain at least one additional gene, such as a selectable marker, to be cotransformed into the organism. Alternatively, the additional gene(s) can be provided on separate vectors.

In some embodiments, a population of vectors is provided, wherein each vector comprises a site, such as, for example, a multiple cloning site, where a cis-regulatory sequence and/or a reporter sequence having a processing tag can be introduced into the vector.

For example, in certain embodiments, a population of vectors is provided, wherein each vector comprises i) a member of a population of substantially identical reporter sequences wherein each reporter sequence of the reporter sequence population has a uniquely positioned processing tag and ii) a multiple cloning site such that a cis-regulatory sequence can be introduced into the site to be operably linked to the reporter sequence. As another example, a population of vectors is provided, wherein each vector comprises a cis-regulatory sequence and a multiple cloning site wherein a reporter sequence can be introduced into the multiple cloning site to operably linked to the cis-regulatory sequence.

In some embodiments, the present invention provides a population of vectors wherein each of the vectors in the vector population comprises a member of a RTU population such as are described in the previous subsections.

The methods of the invention provide the polynucleotides to biological systems. By "biological system" is intended any system that allows the relative activity of the cis-regulatory element or the trans-acting factor to be determined. Such systems include, but are not limited to, a cell-free extract, a mix of proteins, a cell, an organ culture, or a multicellular organism.

"Introducing" is intended to mean presenting to the host cell the polynucleotide in such a manner that the sequence gains access to the interior of the host cell. The methods of the invention do not depend on a particular method for introducing the polynucleotide into the host cell. Methods for introducing a polynucleotide into various organism are known in the art including, but not limited to, stable transfection methods, transient transfection methods, and virus-mediated methods. "Stable transfection" is intended to mean that the polynucleotide introduced into a host cell integrates into the genome of the host cell and is capable of being inherited by the progeny thereof. "Transient transfection" is intended to mean that a polynucleotide is introduced into the host cell and expression of the sequence occurs without integration into the host's genome.

Transfection protocols as well as protocols for introducing polynucleotide sequences into host cells may vary depending on the type of cell targeted. For example, naked DNA constructs can be delivered into cells by using electroporation, injection, biolistic delivery, or spontaneous uptake. Transfection efficacy can be also facilitated by using various transfection reagents, including liposomes (lipofection), dendrimers, proteins, peptides, precipitates, etc. Alternatively, reporter constructs can be inserted into recombinant viral delivery systems, such as retroviral, lentiviral, adeno-associated, adenoviral, or any other vector suitable for delivery of exogenous DNA within cells, followed by infection of cells with resulting reporter viral constructs. Exemplary transformation protocols include calcium phosphate transfection (Chen et al. (1987) *Mol. Cell Biol.* 7:2745-2752; Chen et al. (1988) *BioTechniques* 6:632-638; Ishiura et al. (1982) *Mol. Cell. Biol.* 2:607-616), DEAE-dextran transfection (Yang et al. (1997) *Biotechnol. Appl. Biochem* 25:47-51; Puchalski et al. (1992) *Cytometry* 13:23-30; Fregeau et al. (1991) *Somatic Cell Mol. Genet.* 17:239-257), electroporation (Chang et al. (1989) *Biophys. J.* 56:641-65; Neumann et al. (1982) *EMBO J.* 1:841-845; Potter et al. (1988) *Anal. Biochem* 174:361-373 and Potter (1984) *Proc. Natl. Acad. Sci.* 81:7161-7165), liposome-mediated transfection (Kriegler et al. (1990) *Gene Transfer and Expression A Laboratory Manual,* Stockton Press, New York; Life Technologies (1999) *Guide to Eukaryotic Transfections with Cationic Lipid Reagents,* $2^{nd}$ ed. Life Technologies, Inc., Rockville, Md.; Tilkins et al. *Cell Biology; A Laboratory Handbook,* vol. 4, $2^{nd}$ ed. (J. E. Celis, ed.) pp. 145-154, Academic Press, New York; Felgner et al. (1987) *Proc. Natl. Acad. Sci.* 84:7413-7417), and viral vectors (Walther et al. (2000) *Drugs* 60:249-70; Peng et al. (1999) *Curr Opin Biotechnol* 10:454-7; U.S. Pat. No. 6,613,892; U.S. Pat. No. 6,627,442; U.S. Pat. No. 6,573,092; U.S. Pat. No. 6,498,033; and U.S. Pat. No. 6,468,771). See, also, Sambrook et al. (1989) *Molecular Cloning: A Laboratory Manual* ($2^{nd}$ ed., Cold Spring Harbor Laboratory Press, Plainview, N.Y.) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the polynucleotide of interest. Preferred selectable markers include those that confer resistance to drugs, such as G418, hygromycin, and methotrexate. Nucleic acid encoding a selectable marker can be introduced into a host cell on the same vector as that comprising the RTU or can be introduced on a separate vector. Cells stably transfected with the introduced nucleic acid can be identified by drug selection (e.g., cells that have incorporated the selectable marker gene will survive, while the other cells die).

A host cell can be derived from any cell culture, tissue, or any organ of interest. In one embodiment, the cell is a primary cell. One of skill will recognize the appropriate host cell to employ for a given RTU population. It is understood that the term cell refers not only to the particular subject cell but also to the progeny or potential progeny of such a cell. Because certain modifications may occur in succeeding generations due to either mutation or environmental influences, such progeny may not, in fact, be identical to the parent cell but are still included within the scope of the term as used herein. Non-limiting examples of host cells include any eukaryote cell including, but not limited to, cells from vertebrates, plants (monocots and dicots) and mammals (humans and non-human cells, including cells from mice, dogs, sheep, cows, goats), aves (chicken), yeast, amphibians, etc. Additional host cells of interest include bacterium and fungus. In specific embodiments, cell types of interest include, but are not limited to, embryonic stem cells, and cells or cell lines derived from the spleen, lung, colon, liver, uterus, endometrium, brain, skin, bone marrow, heart, blood vessels, thymus, kidney, breast, testis, prostate, thyroid, skeletal muscle, pancreas, small intestine, or ovary. Other cells of interest include T-cells, B-cells, and bone-forming cells (osteoprogenitor cells, osteoblasts, and osteocytes). In addition, biopsy samples from any organ or tissue (i.e., biopsy sample, autopsy sample, or a slice tissue culture) can be used. Additional cells of interest also include naturally or artificially transformed cell lines including the mammalian 3T3 cell lines, 293 cell lines, Hela cell lines, CHO cell lines, and COS cell lines.

Thus, cells and tissues having a population of polynucleotides comprising the RTUs are provided. As discussed elsewhere herein, these cells are suitable for a variety of screening procedures. In one embodiment, a cell line employed for profiling the activity of at least one trans-acting factor or cis-regulatory element whose activity is modulated by an inflammatory stimuli, a stress stimuli, a cell or developmental stimuli, a toxin, a xenobiotic, or a drug is provided. Exemplary, but non-limiting, trans-acting factors that are modulated by inflammation and/or stress stimuli include NF-κB, NF-AT, AP-1, C/EBPs, Ets-1, Elks, c-Rel, ATF2, c-Fos, CREB-1, and a variety of nuclear receptors, such as, GR, PPARs, RXR, etc. A cell line employed for profiling trans-acting factors and/or cis-regulatory elements whose activities are modulated in a cancerous cell or which influence the regulation of the cell cycle, cell proliferation, and apoptosis is provided. Exemplary, but non-limiting, trans-acting factors having a modulated activity in a cancerous cell or which influence the cell cycle, cell proliferation, and apoptosis, include c-Myc, p53, E2F, Forkhead, TCF/b-catenin, NF-κB, SRE, CRE, DP-1, E2F-1, Rb, p107, Sp-1, c-Myb, Max, USF-1, Egr-1, Oct 1, Oct 11, or estrogen receptors, etc. Cells can also be produced to contain RTUs having cis-regulatory elements that are modulated by factors involved in embryonic development, pain response, neural development and function, etc. These cell lines will be suitable for high-throughput profiling of the activity of a variety of trans-acting factors and cis-regulatory elements.

The cells of the invention can also be used to produce animals having the population of reporter sequences of the invention. In specific embodiments, the population of sequences is stably integrated into the genome of the animal. According, non-human transgenic animals are provided. For example, in one embodiment, a host cell of the invention is a fertilized oocyte or an embryonic stem cell into which the population of RTUs has been introduced. Such host cells can then be used to create non-human transgenic animals in which the population of polynucleotides having the RTUs have been introduced into their genome. Such animals are useful for studying the activity of trans-acting factors of interest, cis-regulatory elements of interest and thereby can be used to obtain molecular signatures of different cell types, developmental periods, treatment regimes, etc. As used herein, a "transgenic animal" is a nonhuman animal in which one or more of the cells of the animal includes a transgene. Examples of transgenic animals include nonhuman primates, sheep, dogs, cows, goats, chickens, amphibians, rodents, etc. A transgene is exogenous DNA that is integrated into the genome of a cell from which a transgenic animal develops and which remains in the genome of the mature animal, under conditions in which the promoter is active, the sequence is expressed in one or more cell types or tissues of the transgenic animal.

Methods for generating transgenic animals via embryo manipulation and microinjection, particularly animals such as mice, have become conventional in the art and are described, for example, in U.S. Pat. Nos. 4,736,866, 4,870,009, and 4,873,191 and in Hogan (1986) *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the population of RTUs in its genome. A transgenic founder animal can then be used to breed additional animals carrying the polynucleotides. Moreover, transgenic animals carrying a transgene having the RTU of interest can further be bred to other transgenic animals carrying other transgenes.

In addition, the population of polynucleotides comprising the RTU can be introduced into cells of certain tissues and organs of experimental animals. Many techniques for doing so are available to those skilled in the art. For example, the RTUs can be transfected in vivo by using direct application of naked DNA, by electroporation, biolistic delivery, virus-mediated in vivo gene transfer, etc. Such hosts will enable investigating the transcription factor activity profile in tissues/organs of interest and also in various disease states. The exposure of such animals to various biologicals allows for assessment of drugs in vivo.

The population of polynucleotides comprising the RTU can be introduced into certain tissues of humans, such as skin, cancer, etc. for diagnostic or screening purposes. For example, reporter species of the RTUs introduced into human skin can be extracted from biopsy samples and used for assessing the state of disease, the efficacy of treatment, the safety of evaluated compounds in humans, etc.

As the compositions disclosed herein can be used to profile the activities of trans-acting factors or cis-regulatory elements, in one embodiment, methods are provided for generating a system that is capable of detecting the relative activity of at least one trans-acting factor or at least one cis-regulatory element. Generating such a system comprises providing a population of isolated polynucleotides, wherein each of the polynucleotides comprises an RTU. Such populations are described in detail elsewhere herein. This population of isolated polynucleotides is provided to a biological system using various techniques that are described elsewhere herein. This system is capable of profiling the activity of a practically unlimited numbers of trans-acting factors and/or cis-regulatory elements, a feature unattainable with existent technologies.

5.2.4. Kits and Systems

Compositions of the invention further include a variety of kits. For example, a kit is provided comprising a population of polynucleotides comprising a reporter sequence having a processing tag, wherein the processing tag can distinguish various reporter sequences from one another. In other embodiments, a kit comprising a population of RTUs is provided. The kits can further comprise a host cell of interest and/or an appropriate vector. Alternatively, the kit can comprise vectors having the population of polynucleotides, or the kit can comprise cells having the population of polynucleotides. Any kit can further include a reference profile, a key correlating the promoter with the reporter sequences in the population of RTUs, and/or directions of use.

In addition, kits can be designed to contain a population of polynucleotides having RTUs that are capable of profiling any desired group of trans-acting factors and/or cis-regulatory elements. For example, the kit can profile any desired group of transcription factors. A kit profiling at least one trans-acting factor or at least one cis-regulatory element that is modulated in response to an inflammatory stimuli, a stress stimuli, a development or a cell differentiation signal, an oncogenesis signal, a toxin, a xenobiotic, or, a drug is also provided. In other embodiments, the kit can profile at least one trans-acting factor and/or at least one cis-regulatory element that are involved in the regulation of or modulated by the cell cycle, cell proliferation, and apoptosis. Kits can also be produced to contain RTUs that are modulated by trans-acting factors or cis-regulatory elements involved in embryonic development, pain response, neural development and function, etc.

Further provided is a database having reference profiles for multiple cis-regulatory elements and/or trans-acting factors. As discussed in detail elsewhere herein, methods and compositions are provided for the identification of molecular signatures of various cell types, treatment regimes, diseases states, drug development, etc. In one embodiment, a database of trans-acting factor profiles or cis-regulatory element activity profiles in various human cancer lines and their normal cell line counterparts is provided. Such a database will allow for the identification of the trans-acting factors and pathways associated with different types of cancer and thus may represent potential targets for drug development.

Further provided is a database having reference profiles for various compounds, including but not limited to, biological agents, chemical compounds, prescription drugs, environmental toxins, etc. In one embodiment, a database of trans-acting factor profiles or cis-regulatory element activity profiles in response to incubation of various cell types in response to treatment with reference compounds is provided. Cell types can, for example, include cancer lines and primary cancer cells. Such a database can be used, for example, to classify an unknown evaluated compound by relating alterations in cis-regulatory elements and trans-acting factors elicited by the evaluated compound to that elicited by known compounds from the reference database and thus predict the toxicological and therapeutic properties and mode of action of the evaluated compound.

Trans-acting factor profiles or cis-regulatory element activity profiles can be cast in a transmittable form that can be communicated between people. Such a transmittable form can vary and can be tangible or intangible. For example, profiles can be embodied in texts, tables, diagrams, photographs, graphs, charts, emails, images or any other visual form. The profiles can be recorded on a tangible media such as paper, plastic transparency sheets, film, and the like, or embodied in computer readable forms (e.g., electronic, electromagnetic, optical or other signals). The data in a computer-readable form can be stored in a computer usable storage medium (e.g., CDs, optical disks, magnetic tapes, digital video discs and the like) and can be in computers storing the information whether temporarily or permanently. In addition, the profiles can be transmitted or stored as "raw" data (i.e., collected but unanalyzed), partially analyzed, or completed analyzed. Data analysis may be by way of computer or some other automated device or may be done manually.

FIG. 22 details an exemplary system that supports the functionality described above. The system is preferably a computer system (10) having:

a central processing unit (22);

a main non-volatile storage unit (14), for example, a hard disk drive, for storing software and data, the storage unit (14) controlled by storage controller (12);

a system memory (36), preferably high speed random-access memory (RAM), for storing system control programs, data, and application programs, comprising programs and data loaded from non-volatile storage unit (14); system memory (36) may also include read-only memory (ROM);

a user interface (32), comprising one or more input devices (e.g., keyboard (28)) and a display (26) or other output device;

a network interface card (20) for connecting to any wired or wireless communication network (34) (e.g., a wide area network such as the Internet);

an internal bus (30) for interconnecting the aforementioned elements of the system; and a power source (24) to power the aforementioned elements.

Operation of computer (10) is controlled primarily by operating system (40), which is executed by central processing unit (22). Operating system (40) can be stored in system memory (36). In addition to operating system (40), in a typical implementation system memory (36) includes:

file system (42) for controlling access to the various files and data structures used by the present invention;

a data structure (44) for storing profiles in accorandance with the present invention; and a data analysis algorithm module (54) for comparing proviles in accordance with the present invention.

As illustrated in FIG. 22, computer (10) comprises software program modules and data structures. Each of the data structures can comprise any form of data storage system including, but not limited to, a flat ASCII or binary file, an Excel spreadsheet, a relational database (SQL), or an on-line analytical processing (OLAP) database (MDX and/or variants thereof). In some specific embodiments, such data structures are each in the form of one or more databases that include hierarchical structure (e.g., a star schema). In some embodiments, such data structures are each in the form of databases that do not have explicit hierarchy (e.g., dimension tables that are not hierarchically arranged).

In some embodiments, each of the data structures stored or accessible to system (10) are single data structures. In other embodiments, such data structures in fact comprise a plurality of data structures (e.g., databases, files, archives) that may or may not all be hosted by the same computer (10). For example, in some embodiments, data structure (44) comprises a plurality of Excel spreadsheets that are stored either on computer (10) and/or on computers that are addressable by computer (10) across wide area network (34). In another example, data structure (44) comprises a database that is either stored on computer (10) or is distributed across one or more computers that are addressable by computer (10) across wide area network (34).

It will be appreciated that many of the modules and data structures illustrated in FIG. 22 can be located on one or more remote computers. For example, some embodiments of the present application are web service-type implementations. In such embodiments, a data analysis algorithm module (54) and/or other modules can reside on a client computer that is in communication with computer (10) via network (34). In some embodiments, for example, a data analysis algorithm module (54) can be an interactive web page.

The present invention can be implemented as a computer system or computer program product. Computer program product embodiments include a computer program mechanism embedded in a computer readable storage medium. For instance, any of the methods disclosed herein can be embodied as a computer program product. The computer program product can be a CD-ROM, a magnetic disk storage product, or any other computer readable data or program storage product. The software in the computer program product may also be distributed electronically, via the Internet or otherwise, by transmission of a computer data signal (in which the software modules are embedded) on a carrier wave.

5.3. Methods

5.3.1. Methods for Profiling the Activity of a Trans-Acting Factor or a Cis-Regulatory Element Methods are provided for assessing activities of at least one cis-regulatory element and/or assessing the activities of at least one trans-acting factor. In specific embodiments, the activity of multiple cis-regulatory elements and/or trans-acting factors are determined in parallel to provide a molecular signature of the biological system of interest. In the present invention, individual reporter sequences within the population of RTUs are distinguished based on the variable positions of the unique processing tag within their reporter sequence. Upon processing, reporter species of the individual reporter sequences produce distinguishable fragments. Thus, methods are provided for detecting the activity of at least one trans-acting factor or at least one cis-regulatory element in a biological system.

In embodiments of the methods provided, activities to be detected are in a biological system comprising a population of polynucleotides, for example, an RTU population, as described in Section 5.2. In certain embodiments, the reporter species of the reporter sequences are processed and at least two of the processed reporter species are detected. The relative activity of at least one trans-acting factor and/or cis-regulatory element is thereby determined.

In some embodiments, the reporter species of the reporter sequences are processed and an amount of processed reporter species quantitated, then compared to a reference to determine the activity of a trans-acting factor and/or cis-regulatory element.

Reference RTUs, can include, for example, an RTU containing a non-inducible promoter of a housekeeping gene, a viral promoter, etc., or any RTU by which a comparision can be made to determine the activity of a trans-acting factor and/or cis-regulatory element.

As used herein, the term "reporter species" of the reporter sequences encompasses not only the actual RNA product produced in the biological system, but also any derived nucleic acid (e.g., cDNA or any amplified product, etc.) that is generated during an amplification step, a processing step, a detection step and/or a quantitating step.

As outlined above, various processing tags can be employed in the reporter sequences which when processed using the appropriate method, will permit the detection of the reporter species and subsequently allow the detection and/or quantitation of the activity of the trans-acting factor or the activity of the cis-regulatory element. For example, a processing tag can comprise a unique mutation in the reporter sequence, an endonuclease recognition site, a termination signal, a common primer sequence, or any other sequence that can mark reporter species for processing at a predetermined site. Depending on the nature of the processing tag, the processing can be accomplished by an enzymatic reaction, a chemical reaction, a thermal reaction, or a combination thereof. The processing can also be accomplished by amplification, by termination of amplification, or by any other process that generates or identifies distinguishable products of individual reporter species. Non-limiting examples of the use of these processing tags are discussed in detail below.

In specific methods, following expression of the reporter sequence in the biological system, the processing can be carried out with reporter RNA transcripts that are isolated and purified from the biological system. Methods of isolation and purification are known and include, for example, Trizol extraction, column chromatography, polyA affinity columns, cesium gradient, or any other available means. Alternatively, the processing of reporter transcripts can be carried out without prior purification, e.g., in cell lysates, tissue homogenates, etc.

In specific embodiments of the invention, it may be desirable to convert reporter RNA transcripts into complementary DNAs prior to processing. This can be done by reverse transcription, for which many enzymes are available, including viral reverse transcriptases, such as MoMLV, SuperScript, PowerScript etc. Various primers for the reverse transcription can be employed, including a primer that binds to the 3' polyadenylated sequences, primers complementary to the reporter sequence, a combination of random primers, or any other primers suitable for reverse transcription.

In specific embodiments, prior to the processing step or during the processing step, the transcription products of the reporter sequences can be amplified to increase the sensitivity of the detection process. The term "amplification" or "amplified" as applied to nucleic acids refers to any method that results in the formation of one or more copies of a nucleic acid, where optimally the amplification is exponential.

One method for enzymatic amplification of specific sequences of DNA is known as the polymerase chain reaction (PCR), as described by Saiki et al. (1986) *Science* 230:1350-54. For example, reporter sequence can be provided with 5' and 3' primer sequences that can be used for PCR amplification. Primers used in PCR can vary in length from about 10 to 50 or more nucleotides, but will correspond to the primer sequences present in the RTUs that are to be amplified. The double stranded fragment that is produced from PCR amplification is called an "amplicon" and may vary in length from as few as about 30 nucleotides to 20,000 or more.

In one method, reverse transcription followed by PCR amplification is performed on the reporter species. Enzymatic conversion of RNA into double stranded DNA can be accomplished by a number of different procedures. In general, the protocols employ reverse transcriptase and oligonucleotide primed synthesis of cDNA. See, for example, Gubler et al. (1983) *Gene* 25:263-269; Huse et al. (1988) *Strategies (Stratagene)* 1:1-3; and Okayama et al. (1982) *Mol. Cell. Biol.* 2:161-170. See, also, Freeman et al. (1999) *Biotechniques* 26:112-22; Ambion's Armored RNA® Technology; and Ullmann et al. (2001) *Quiagen News* 2:13-16, all of which are herein incorporated by reference in their entireties. RT-PCR can be performed in either purified total RNA samples or in whole cell lysates.

To facilitate detection of processed reporter species (i.e., reporter RNA transcripts, cDNA, their amplified products, etc.) the reporter species can be labeled by any appropriate means. For example, the label can be incorporated into primers that are used for amplification of reporter species. Many different labels are available, including radioactive nucleotides, fluorescent labels, or color labels. The primers can be also conjugated with different colorigenic or fluorogenic enzymes, such as horseradish peroxidase or alkaline phosphatase, or can be conjugated with ligands, such as biotin, that can be used for the subsequent detection by immunodetection. The reporter cDNA or products of amplification can be labeled by adding labeled nucleotides into the amplification mixture. The processed reporter species can also be labeled in the process of detection, e.g., by DNA or RNA stains.

A number of detection methods may be used in the present invention to detect and discriminate between the processed reporter species. The detection step may be either qualitative (i.e., for purposes of detection only) or quantitative (i.e., measuring the amount of each processed reporter species). The processed reporter species of individual reporters can be assessed by many available means, depending on the nature of processing. The processed reporter species produced by the various processing techniques can be separated by a variety of characteristics including, but not limited to, size, molecular weight, electric charge, mobility, or any combination thereof. In other embodiments, the processed reporter species are separated by gel electrophoresis, capillary electrophoresis, chromatography, or any other method that is capable of separating the processed reporter species sufficiently so they can be detected and/or quantitated. Such methods are described elsewhere herein. See, also, Ronai et al. (2000) *American Laboratory* 7:28-31; 6,127,124; and 5,167,783, all of which are herein incorporated by reference. The amount of processed reporter species in separated bands can be quantitatively evaluated by using the labels incorporated into reporter species. The processed species can be visualized by staining them before, during, or after the separation procedure, with many available DNA stains, such as ethidium bromide, PicoGreen, etc.

FIGS. 1-9 provide non-limiting examples of various processing techniques and methods for detecting the processed reporter species.

The example presented in FIG. 1 provides a non-limiting example to assess activities of multiple trans-acting factors or cis-regulatory elements. As depicted, RTU A and RTU B are introduced into a biological system, each comprising a cis-regulatory sequence (2) which is operably linked to a reporter sequence (4) comprising processing tag (6) such that the cis-regulatory sequence (2) modulates the abundance of RNA transcripts of the reporter sequence (4) in response to activity of a corresponding trans-acting factor. The substantial identity between reporter sequences confers substantially identical transcription efficacies for each reporter sequence such that the relative abundances of reporter RNA messages (8) reflect the activities of their respective cis-regulatory sequences in the RTUs. Reporter RNA messages (8) or their derivatives (e.g., cDNA) are isolated and subjected to processing guided by the processing tag (6) that produces distinguishable processed reporter species (9) that can be separately assessed.

To assess N different cis-regulatory sequences or trans-acting factors, a library of N individual reporters is introduced into a biological system and the reporter species can be processed in parallel.

FIG. 2 provides a non-limiting embodiment of the invention where the processing tag comprises a sequence (7) that marks the reporter species for cleavage at a predetermined site by a double-strand (ds) DNA-cleaving endonuclease (18). Each of the RTU in the population comprises a unique processing tag (7) in the reporter sequence (4), wherein the position of the processing tag is different in each of the RTUs in the population. A variety of DNA endonucleases are available for this purpose, including EcoRI, BamHI, SmaI, Hind III, or any other endonuclease that specifically recognizes and cleaves the processing tag (7). In one embodiment, the endonuclease recognition site is unique in the reporter sequence, so that the endonuclease cleaves the reporter sequence only once. In still other embodiments, the endonuclease may cleave the reporter sequence at multiple sites, provided that distinguishable processed reporter species of the individual reporter species are generated.

Upon introduction into a biological system, the RTUs produce reporter RNA transcripts (8) commensurable with the activity of the cis-regulatory sequence (2). The reporter transcripts (8) are reversely transcribed into single-strand (ss) cDNAs (10) that serve as templates for generating ds DNAs (16) containing endonuclease recognition site (7) that can be cleaved by the ds DNA-cleaving endonuclease (18). The ss cDNA can be converted into the dsDNA by various means. For example, the single-stranded reporter DNA can be conversed into the double-stranded reporter DNA by using exponential amplification with polymerase chain reaction (PCR); the forward primer (13), or the reverse primer (14), or both primers can be provided with a label (12). Alternatively, dsDNA can be generated by linear amplification, e.g., by DNA polymerase-catalyzed primer extension. The produced double-stranded reporter DNAs are processed by incubation with the restriction endonuclease (18), thereby producing a unique set of DNA digestion products for each reporter. These digestion products can be separated according to their molecular weights, e.g., by using gel electrophoresis, capillary or column chromatography, or by any other available means. The relative amounts of DNA products in the bands can be quantitatively assessed by using DNA labels (12) or by staining DNA fragments with DNA stains.

In still other embodiments, the processing tag comprises a mutation in the reporter sequence at a site that is unique for each individual reporter sequence in the population. The mutation can comprise a substitution, or insertion, or deletion of a single or multiple nucleotides. In specific embodiments, the reporter sequences in the population are substantially identical to one another. A non-limiting schematic of this method is depicted in FIG. 3. Specifically, the RTU in the population comprises a unique processing tag (24) comprising a mutation in the reporter sequence (4) wherein the position of the processing tag (24) is different in each RTU and where the processing tag (24) can distinguish reporter species of each RTU in the population. The reporter transcripts (8) are hybridized with an excessive amount of the wild type (wt), non-mutated DNA (26), producing double stranded heteroduplexes of RNA/cDNA that contain a mismatch at the position of the processing tag (24). Alternatively, the reporter transcripts can be hybridized to a complementary strand of wild type, non-mutated, reporter RNA, thereby producing double stranded RNA heteroduplexes containing mismatches at the position of the processing tag (24). Due to the label (12), upon cleaving and separation of duplexes, labeled fragments (20) and unlabeled fragments (22) can be separated and individually assessed for each RTU in the population.

The RNA/RNA, RNA/cDNA or cDNA/cDNA heteroduplexes can be selectively cleaved at the mismatch sites by different means, e.g., by using enzymes that specifically recognize and cleave the mismatch sites in heteroduplexes. Several such enzymes are available (Oleykowski et al. (1998) *Nucl. Acid Res.* 26:4597-4602, and Taylor and Deeble (1999) *Genet. Anal.* 14:181-6). For example, S1 nuclease, RNase, T4 endonuclease VII, T7 endonuclease I, CEL 1, or in vitro reconstructed mismatch repair complexes, such as MutY-thymine glycosylase system, can be used. Chemical reactions that can be employed include mismatched thymines and cytosines which are susceptible to modifications by osmium tetroxide and by hydroxylamine, respectively. The modified bases can be then specifically cleaved by piperidine (Taylor (1999) *Electrophoresis* 20:1125-30). The cleaved reporter species (e.g, dsRNAs, dsDNAs, or RNA/DNA heteroduplexes) are separated and individually assessed, as described above. For the purpose of detection, the processed reporter species can be labeled by various means, e.g., by using labeled annealing wt RNA or cDNA, or by introducing a label into the reporter RNA at the level of transcription, e.g., by supplying the biological system with labeled nucleotides, or by any other means.

To increase the sensitivity, the reporter species can be amplified prior to processing, for example, by RT-PCR, or by linear amplification with DNA polymerase. The complementary strands of the amplified DNA are separated by denaturation, hybridized with an excessive amount of complementary wtRNA or wt DNA, processed and detected as described above.

In certain embodiments of an RTU population of the invention, each RTU comprises a common reporter sequence containing a processing tag, wherein the processing tag comprises a mutation of the common reporter sequence where the mutation is unique to a given RTU. The mutation can comprise a substitution, or insertion, or deletion of a single or multiple nucleotides.

In another embodiment, the processing tag comprises a unique thymidine residue that is introduced into one strand of the reporter sequence. A non-limiting schematic of this embodiment is illustrated in FIG. 4. In this embodiment, the processing tag (32) comprises a unique thymidine (T) residue that is introduced into one strand of the reporter sequence (4), specifically within the transcribed strand (5), comprising multiple residues of adenine (A), guanine (G), and cytosine (C). Reporter transcripts (8) are reversely transcribed and amplified by linear or PCR amplification in a reaction containing a mix of dATP, dGTP, and dCTP, and deoxyuracyl (dUTP) nucleotides, resulting in dsDNA products (34) in which T moieties are substituted by uracyl (U).

The U moieties are treated with uracyl-deglycosydase (UDG) (36) that produces thermolabile deglycosylated-uracyl moieties (37). The resulting DNA can be cleaved at the deglycosylated uracyl moieties (37), e.g., by thermolysis, such as by incubation at 75° C. This processing introduces a single break into the transcribed strand of DNA and multiple breaks into the complementary strand. To facilitate detection, label (12) can be introduced into the transcribed strand of DNA. The labeled processed reporter species (38) are separated according to their molecular weights, e.g., by electrophoresis, and quantitatively assessed.

Figure 5:
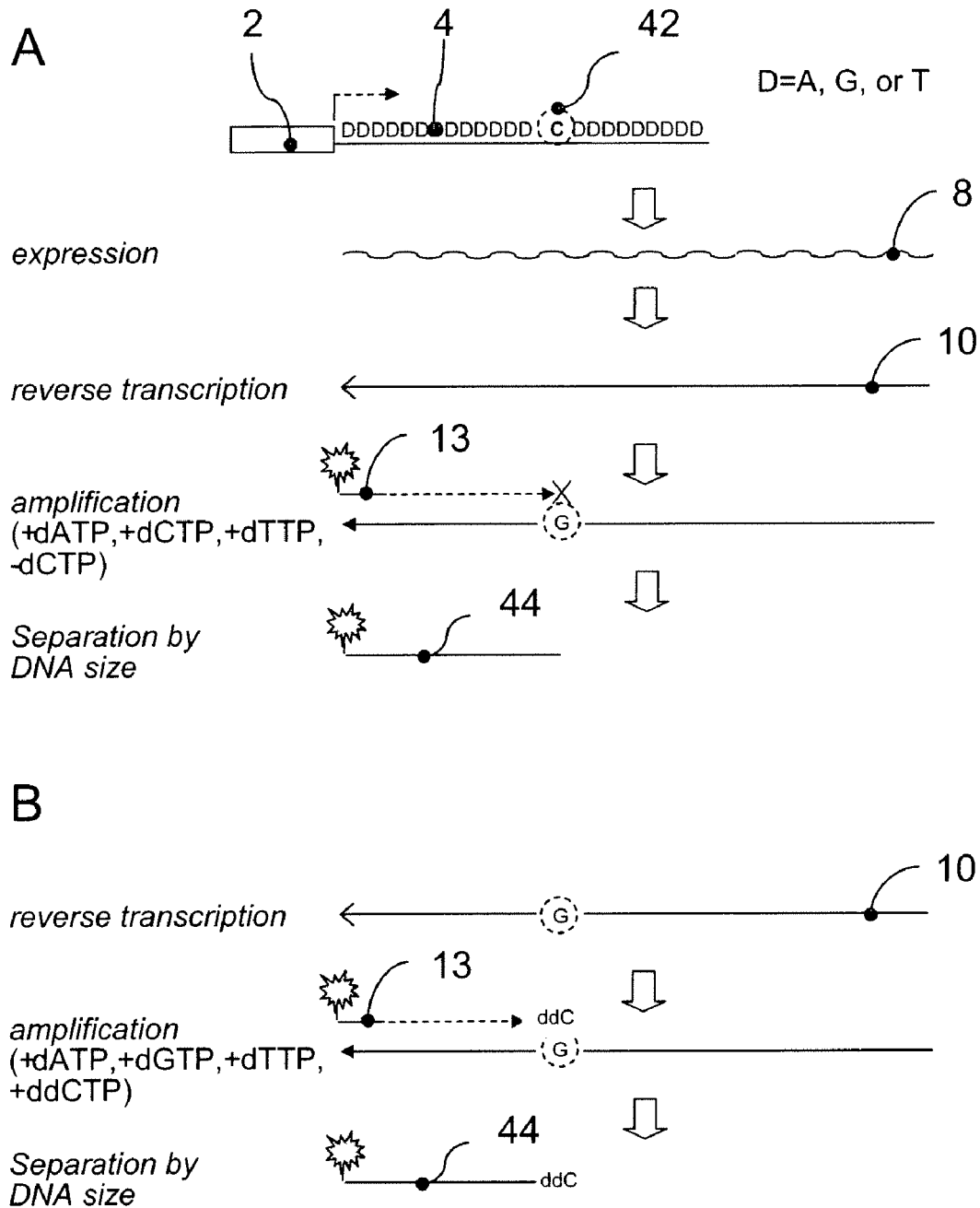

In other embodiments, the processing tag comprises an extension termination signal and processing of the reporter species comprises incubating the reporter species under conditions that allow termination of an extension reaction at the termination signal. FIG. 5 provides a non-limiting example of this processing tag. In this embodiment, the processing tag (42) represents a termination amplification signal. The reporter sequence (4) is designed in such a way that the transcribed strand (depicted as "D" nucleotides) does not contain one of the four nucleotides. For example, in the embodiment depicted by FIG. 5A, the transcribed strand contains adenine (A), guanine (G), and thymidine (T), but no cytosine (C) residues, other than at the processing tag that is introduced at a position that is unique for each individual reporter. Reporter transcripts (8) are reversely transcribed in a reaction mix that contains all four nucleotides, dATP, dGTP, dCTP, and dTTP, enabling the generation of full-length complementary DNA (10) that comprises a unique G residue at the position corresponding to the position of the unique C residue (42) in the transcribed strand of the reporter sequence (4). The cDNA serves as a template for subsequent processing that is carried out by DNA polymerase-catalyzed linear amplification reaction employing labeled forward primer (13) and a mix containing three nucleotides, in this example, dATP, dGTP, and dTTP nucleotides, while dCTP nucleotides are omitted. The synthesis of the complementary strand of reporter cDNA terminates when DNA polymerase encounters the unique G residue in the cDNA template, due to unavailability of the required complementary nucleotide (dCTP). Thus, the processing produces labeled single stranded DNA (44) whose length is predetermined by the position of the processing tag (42).

Alternatively, the termination of amplification can be achieved by including into the amplification mix a terminating nucleotide, as depicted by FIG. 5B. In this example, the terminating nucleotide represents a dideoxy (ddCTP) derivative of dCTP, which is routinely used for terminating sequencing reaction (Sanger et al. (1977) *Proc. Natl. Acad. Sci.* 74:5463-5467 and Sanger et al. (1980) *J. Mol. Biol.* 143:161-178). Alternatively, any modified nucleotide analogue that halts the polymerase reaction can be used. It is recognized that in the described embodiment, either of A, G, C, and T nucleotides can be used as the processing tag. To increase sensitivity, the reversely transcribed cDNA (10) can be amplified prior to processing by PCR amplification.

In yet another embodiment, the processing tag comprises a primer sequence which is positioned relative to the reporter sequence and varies for each RTU in the population. The processing of such reporter species comprises amplifying the reporter species under conditions that produce amplification products whose lengths are determined by the variable position of the processing tag. A non-limiting example of this embodiment is depicted in FIG. 6. In this embodiment, the processing tag comprises a primer sequence (46), whose relative position to the reporter sequence (4) varies for each RTU in the population. The reversely transcribed reporter cDNA (10) serves as a template for processing, which is carried out by a DNA polymerase-catalyzed linear amplification in the presence of reverse primer (48) that is complementary to the sequence of the processing tag (46). The processing produces single stranded DNA (50) whose length is determined by the position of the processing tag (46). Alternatively, the processing can be carried out by exponential amplification of the cDNA template by PCR, using a pair of primers, one of which is complementary to the sequence of the position tag (46), and another primer is complementary to a common region of the reporter cDNA. The processed reporter species are separated according to their distinct molecular weights and quantitatively assessed.

In certain embodiments, oligonucleotide probes complementary to regions of a reporter species comprising the processing tag sequence and one, or both, flanking sequences of the reporter sequence flanking the processing tag sequence can be utilized in the methods provided. FIG. 7 provides an illustration for the use of oligonucleotide probes in distinguishing reporter species in the methods provided herein. An RTU comprising a cis-regulatory sequence (2) operably linked to a reporter sequence (4) in such a way that the cis-regulatory sequence (2) determines the abundance of RNA transcripts of the reporter sequence (4). To assess multiple transcription factor activities, a population of N RTUs is assembled wherein the positions of the processing tags (6) within substantially identical reporter sequences (4) distinguish between any two RTUs having reporter sequences transcriptionally modulated by non-identical trans-acting factors. To detect reporter transcripts (8), a detection array can be used that comprises a population of oligonucleotide probes (51) comprising a fluorescent label (55) whose fluorescent properties can be modulated by processing of the probe. Each individual probe within the array selectively detects the reporter species of one particular RTU. To do so, the sequence of the probe is complementary to a part of the reporter sequence of a particular RTU that includes the processing tag.

The array is contacted with reporter species under annealing conditions to form heteroduplexes of reporter species with detection probes. Owing to substantially identical reporter sequences, reporter species of different RTUs may form heteroduplexes with each detection probe. However, only the heteroduplexes wherein the position of the processing tag in the probe matches the position of the processing tag in the reporter species can be processed, and thus alterations of fluorescence of an individual probe within the detection array are commensurable to the amount of reporter species of one particular RTU.

FIG. 8 illustrates a non-limiting embodiment of a detection method depicted by FIG. 7 wherein the processing tag comprises an endonuclease recognition site (7). In this example, a population of RTUs comprises RTU A and RTU B that possess an identical reporter sequence (4) and the processing tag (7) whose position is different for the RTU A and RTU B. The reporter transcripts (8) produced by the population of RTUs are reversely transcribed into complementary DNAs (10) and hybridized to detection array comprising two detection probes (51), probe A and probe B. The probe A comprises a part of the reporter sequence that includes the processing tag (7) in RTU A, while the sequence of the probe B comprises a part of the reporter sequence that includes the processing tag (7) in RTU B. Both detection probes are provided with a fluorescent donor-acceptor pair comprising a fluorescent label (55) and a quencher of fluorescence (57). In an intact probe, the quencher (57) renders the fluorescent label (55) non-fluorescent, because it absorbs the excitation energy through the mechanism known as the fluorescence resonance energy transfer (FRET).

When hybridized to probe A, reporter cDNA A forms a heteroduplex that can be processed by digest with the restriction enzyme (18), which releases the fluorescent label (55) from the vicinity of the quencher (57) and thus this increase of fluorescence yield can be observed. In contrast, the mismatched heteroduplexes formed by the reporter cDNA B and the probe A are resistant to the enzymatic digest. However, the hybridization followed by the enzymatic digest releases the fluorescently detectable probe (55) from the heteroduplexes formed by the probe B and cDNA B, but not from the heteroduplexes formed by the probe B and cDNA A.

FIG. 9 illustrates another non-limiting embodiment of the detection method depicted by FIG. 7 wherein the processing of the probe is accomplished by a 5'-nuclease digest. In this example, arrayed detection probes (51) comprising a fluorescent donor (55)-acceptor (57) pair are hybridized with reporter cDNAs in the presence of a common primer (13) that is complementary to a non-variable region of the reporter sequence (4). The resulting heteroduplexes are subjected to primer extension reaction that is catalyzed by a DNA polymerase possessing a 5'-exonuclease activity, e.g., Taq polymerase. The DNA polymerase extends the primer (13) toward the hybridized probe (51). If the probe forms the perfect match with the reporter cDNA, the 5'-exonuclease activity of the DNA polymerase degrades the probe and thus releases the fluorescent probe (55) from the vicinity of the quencher (57) and thus increases fluorescent yield of the label (55). If there is a mismatch between the reporter cDNA and the probe, the DNA polymerase-synthesized strand replaces the probe (51) from the template without degradation, thus not increasing the fluorescence signal. 5'-nuclease digestions are known to those skilled in the art, such as the TAQMAN assay described in Holland et al. (1991) *Proc. Natl. Acad. Sci. USA.* 88:7276-7280.

There are many ways whereby detection probes can be arranged into detection array. For example, the detection probes can be in a liquid phase, e.g., in wells of a 96-well plate, 384-well plate, 1,536-well plate, etc., for performing the hybridization with reporter species and processing. Alternatively, the probes can be immobilized on a surface, e.g., on a glass, on a nitrocellulose filter, on the surface of beads, on a column, etc., and the hybridization of the probes to reporter species can be performed on the surface, while fluorescent detection can be performed by analyzing the probe that is released into solution or on the probe remaining on the surface.

Any donor-acceptor pairs can be used to label the detection probes discussed above. For example, the fluorescent label can comprise any fluorophore, such as fluorescein, 6-FAM, rhodamine, a quantum dot, etc. Furthermore, the quencher can be substituted with a fluorescent molecule whose excitation spectrum overlaps with the emission spectrum of the first fluorescent molecule. For example, as depicted in FIGS. 8 or 9, the excitation can be transmitted from the first fluorescent molecule (55) to the second fluorescent molecule (57) through FRET, so that the emission spectrum of the probe is determined by the properties of the second fluorescent molecule (57). Following the processing, the fluorescent probes become separated, which eliminates FRET, and thus the emission spectrum of the fluorescence shifts into the spectral range that is determined by the properties of the first fluorescent molecule (55), while the fluorescent signal emitted by the second fluorescent molecule (57) diminishes. Therefore, the processing can be evaluated by assessing the ratio of the intensities of fluorescence signals at distinct wavelengths.

Those skilled in the art appreciate that many other methods of processing of the detection probe can be used that can alter the fluorescence of the probe. For example, one can substitute the 5'-exonuclease degradation/strand displacement assay with an invader assay. As another example, arrays of other labeled detection probes can be employed that can recognize the processing tag that is located at a particular position of the reporter sequence, e.g., MOLECULAR BEACON probes comprising the sequence including the processing tag.

Methods are also provided to assess the activity of multiple transcription factors for which DNA binding sequences are not known. Exemplary RTUs for use in such methods are depicted in FIG. 10. For example, in FIG. 10A, a chimeric coding sequence (52) can be constructed to encode an in-frame fusion protein (58) of a transcription factor "A" with a DNA binding domain ("DBD") from a protein with a known DNA binding specificity. To avoid interference with endogenous gene expression in the biological system, the DBD is preferentially derived from a remote biological species. For example, yeast transcription factor Gal4, which does not bind regulatory elements in the mammalian genome, can be used for examining transcription factors in mammalian cells. The Gal4 DNA binding domain provides specificity of DNA binding, whereas the evaluated transcription factor A determines the transcriptional activity of the fusion protein. The chimeric coding sequence (52) is constitutively expressed from a promoter (54), which can be a promoter from viruses, e.g., CMV, or SV40, or a promoter of a housekeeping gene, or any other suitable promoter. The chimeric coding sequence (52) is inserted with the promoter (54) into an RTU containing a cis-regulatory sequence (56) that is specifically recognized by the Gal4 DBD of the fusion protein. It is important that the inserted constitutive promoter (54) does not affect the transcription of the reporter sequence (4), for example, by orienting promoter (54) in a direction opposite to the direction of transcription of the reporter sequence (4), or, as another example, by inserting an insulator (e.g., terminator of transcription) upstream of the cis-regulatory element (56). The regulatory sequence (56) is operably linked to a reporter sequence (4) that is supplied with a processing tag (6). When the reporter construct is transfected into cells, fusion protein (58), expressed from the chimeric coding sequence (52), binds the regulatory sequence (56), thereby activating the transcription of the reporter sequence (4) commensurable with the transcriptional activity of evaluated transcription factor A.

To assess the activities of two transcription factors (A and B) in parallel, two RTUs are used: one RTU, depicted by FIG. 10A, and another RTU, depicted by FIG. 10B, that expresses chimeric coding sequence (53), encoding fusion protein TF B-Gal4 (60). In FIG. 10B, the chimeric coding sequence (53) is inserted into a construct containing the regulatory sequence (56) that is operably linked to a reporter sequence (4), which is supplied with a processing tag (6) at a position distinguishable from that in the reporter construct depicted by FIG. 10A. To simultaneously assess the transcription factors A and B, a mixture of the two RTUs is transfected into a biological system. To avoid cross-talk of fusion proteins (58) and (60) on the common regulatory sequence (56), reporter constructs are transfected at a low multiplicity of transfection, so that transfected cells, on average, receive less than one copy of reporter constructs. Alternatively, individual reporter constructs are separately transfected in cells that can be followed by pooling of the transfected cells. The reporter species are processed and analyzed as described above. In some embodiments, the reporter species from different RTUs separately transfected into cells can be separately assessed. This approach can be expanded for assessing any number of transcription factors, by including corresponding RTUs into the population.

The approach depicted by FIG. 10 can be used for examining transactivation function of transcription factors. The transcriptional activity of most transcription factors is regulated at many levels, including modulation of DNA binding affinity, and modulation of the ability of transcription factors to recruit co-activators, co-repressors, and basal transcriptional machinery, frequently referred to as transactivation function. The transactivation function, which is often regulated independently of DNA binding activity, carries important biological information. For example, regulation of the transcription factor NF-kB is mediated by nuclear translocation of NF-kB and is controlled by degradation of inhibitory molecule known as IkB. However, other IkB-independent pathways exist that modulate transactivation function of NF-kB subunits. The present invention provides examining the transactivation function of multiple transcription factors using reporter constructs that are similar to those depicted by FIG. 10. In these constructs, transactivation domains of evaluated transcription factors are fused in frame with DNA binding domains from a heterologous protein with known DNA binding specificity, e.g., Gal4. For example, to determine transactivation function of RelA, one constructs a chimeric DNA encoding a fusion protein of the transactivation domain of RelA with DBD Gal4. The transcription of such reporters is independent of DNA-binding activity of NF-kB and is determined by the transactivation function of RelA.

The present invention can be also used for assessing activities of different transcription factors that have essentially similar DNA binding sequences. For example, distinct families of nuclear receptors often can bind the same DNA sequences. To distinguish transactivation functions of multiple nuclear receptors, RTUs can be designed similar to that depicted by FIG. 10. In these reporter constructs, the transactivation domains of nuclear receptors are fused in frame with DBD from a heterologous protein with known DNA binding specificity, e.g., Gal4, and assess the reporter library as described above. Exemplary methods of detecting the activities of nuclear hormone receptors with overlapping DNA binding specificities are described in the working examples.

The methods and compositions can be used for the assessment of activities of cis-regulatory sequences and trans-acting factors in various biological systems, including mixes of proteins, cell-free extracts, cell cultures, tissues, organs, whole animals, biopsy and autopsy samples, as well as kits and assays derived from the compositions and methods.

The populations of RTUs can be also used for assessing the activities of multiple cis-regulatory elements and/or of trans-acting factors ex vivo. For example, a population of RTUs can be introduced in explants of primary cells obtained from animals or humans. The populations of RTUs can be also introduced in explanted cells and tissues, e.g., blood samples, biopsies and autopsies of various organs and tissues. The explants are incubated in culture for a period of time sufficient for reporter transcription to occur. Because gene transfer itself and the reporter transcription occur rapidly (during one to two hours), it should be possible to investigate the activity of the trans-acting factor or the cis-regulatory element while the explanted tissue retains its integrity. Also, owing to the high sensitivity of PCR detection, it should be possible to determine the profiles of trans-acting factors or cis-regulatory elements in small samples of biological specimens.

Alternatively, following transfection with an RTU population, the transfected primary samples can be reintroduced into the host, enabling monitoring of profiles of trans-acting factors and cis-regulatory elements in vivo. At a desirable time, the reporter species can be isolated from the reintroduced samples, processed and detected as described above.

The explants can be stimulated in vitro with treatments of interest to assess the effect of these treatments on the cis-regulatory element and/or the trans-acting factors. The populations of RTUs can be used for assessing activities of multiple cis-regulatory elements and/or of trans-acting factors in particular anatomical sites of explanted tissues. To this end, explanted tissues are dissected and reporter species are isolated from anatomical sites of interest.

The populations of RTUs can be used for assessing activities of multiple cis-regulatory elements and/or of trans-acting factors in vivo. To this end, the population of RTUs is introduced in analyzed tissues or organs of live animals or humans by using appropriate delivery vehicles. The biopsy samples are recovered from transfected animals or humans and reporter species are isolated and processed.

The methods and compositions can be used to assess the activities of multiple cis-regulatory elements and/or trans-acting factors during embryonic development. In this embodiment, a population of RTUs is integrated into the genome of an embryonic stem (ES) cell followed by implantation of the resulting reporter ES cells in utero. At different stages of development, the reporter embryo/fetus is microdissected and subjected to the analysis of the trans-acting factor or the cis-regulatory element. Alternatively, the population of RTUs can be delivered into the fetus by using in utero gene delivery.

The reporter ES cells can also be used for generating reporter transgenic animals that comprise the population of RTUs in each cell of the animal. These reporter animals can be used for profiling the activities of multiple cis-regulatory elements and/or trans-acting factors in various tissues, cells, and organs in postnatal development, embryonic development, in various models of disease, for in vivo drug evaluation and to investigate the effects of different treatments (such as administering various compounds, stress, pathogens, pain stimuli, various diseases, tumor transformation, etc.) in vivo in whole animals.

5.3.2. Methods for Characterizing Cell Types and/or Disease States Based on the Profile of Trans-Acting Factor Activity or Cis-Regulatory Element Activity in a Sample By detecting and/or quantifying the activity of trans-acting factors and/or cis-regulatory elements in a biological system, the present invention allows one to rapidly characterize a biological system based on which activated trans-acting factors are present and at what levels. In addition, certain disease states may be caused and/or characterizable by certain genes being expressed or not expressed as compared to normal cells. Other disease states may result from and/or be characterizable by certain genes being transcribed at different levels as compared to normal cells. By being able to rapidly monitor the activity of multiple trans-acting factors and/or cis-regulatory elements, the present invention provides an accurate method for diagnosing certain disease states known to be associated with no activity, reduced activity, and/or elevated activity of one or more trans-acting factor and/or cis-regulatory element. Conversely, by comparing the lack of activity, reduced activity, and/or elevated activity of one or more trans-acting factor or cis-regulatory elements in normal and abnormal cells, the present invention facilitates the association of a trans-acting factor activity profile or cis-regulatory element profile activity with certain disease states. In addition, by understanding that a particular disease state is caused by a different activity (higher or lower) of one or more trans-acting factors and/or cis-regulatory elements, it should be possible to remedy the disease state by increasing or decreasing the expression of one or more trans-acting factors, by administering an appropriate treatment.

A "trans-acting factor activity profile" is a collection of values representing the absolute or the relative activity of one or more trans-acting factors that are present at different levels in the biological system of interest. A "cis-regulatory element activity profile" is a collection of values representing the absolute or the relative activity of one or more cis-regulatory elements that are present at different levels in the biological system interest. Preferably, a trans-acting factor activity profile or a cis-regulatory element activity profile will contain a sufficient number of values such that the profile can be used to distinguish one sample from another, or to distinguish subjects in one risk group from those in another risk group. In some embodiments, a single value may be sufficient to distinguish one sample from another.

In certain embodiments, a trans-acting factor activity profile is a collection of N values representing activities of the N RTUs. In some embodiments, N is 10 or more, 20 or more, 50 or more, 100 or more, 1000 or more, between 10 and 1000, or less than 4,000. The profile can be characterized as a vector in an N-dimensional space, where the activities of individual transcription factors are coordinates of the vector. The trans-acting factor activity profiles of two different biological systems can be quantitatively compared. The similarity between two profiles can be quantitatively evaluated using a broad array of distance metrics including, but not limited to Euclidean distance, Manhattan distance, Chebychev distance, an angle between vectors (or a function of the angle, e.g., cosine), correlation distance (e.g., Pearson correlation distance), squared Euclidean distance, standardized Euclidean distance, Mahalanobis distance, and Minkowski distance. See, for example, Draghici, 2003, *Data Analysis Tools for DNA Microanalysis*, Chapman & Hall/CRC, New York, pp.264-276, hereby incorporated by reference in its entirety, for a discussion of such distance metrics for vectors. In some embodiments, the distance between the ends of the corresponding N-dimentional vectors (so-called Euclidean distance) is measured. In some embodiments the angle between the vectors, also known as a Pearson correlation co-efficient Cor (A,B) (see formula I below), is measured. The Pearson correlation analysis has been used to compare profiles of gene expression in transcriptomics, where two or more profiles of gene expression obtained by array hybridization are compared (see, e.g., Scherf et al. (2000) *Nature Genetics* 24:236-244, which is hereby incorporated by reference in its entirety).

The formula for a Pearson correlation is the following:

$$Cor_{(A,B)} \equiv \frac{\sum_n (A_n - <A>) \times (B_n - <B>)}{\sqrt{\sum_n (A_n - <A>) \times (A_n - <A>)} \times \sqrt{\sum_n (B_n - <B>) \times (B_n - <B>)}} \qquad \text{Formula 1}$$

The value of the Pearson correlation coefficient Cor varies from +1.0 (perfectly matching profiles) to −1.0 (completely dissimilar profiles). For example, when A and B represent two different trans-acting factor activity profiles comprising values of N individual trans-acting factors, their coordinates are respectively $(A_1, A_2, A_3 \ldots A_N)$; and $(B_1, B_2, B_3 \ldots B_N)$, where $A_1, A_2, A_3$, etc. are values of activities of trans-acting factors TF1, TF2, TF3, etc. of the profile A, $B_1, B_2, B_3$, etc. are values of trans-acting factors TF1, TF2, TF3, etc. of the profile B., and $<A>$ and $<B>$ represent the mean of values of all individual trans-acting factor activities of profiles A and B. In some embodiments, profiles A and B are considered matching when the Pearson correlation coefficient between A and B is 0.5 or greater, 0.6 or greater, 0.7 or greater, 0.8 or greater, 0.9 or greater, 0.95 or greater, or 0.99 or greater. As noted above, other metrics for comparing the trans-acting factor activity profiles are also available, including non-parametric rank-order correlation, Chebyshev distance, etc.

In one method, cell types and/or disease states are characterized by generating a reference profile to a known sample and comparing that reference profile to the trans-acting factor activity profile or the cis-regulatory element activity profile of an unknown or uncharacterized sample. As used herein, a "reference profile" is a trans-acting factor activity profile or a cis-regulatory element profile that is characteristic of a particular biological system (i.e., cell type and/or disease state). Methods for generating this reference profile comprises introducing into a known or characterized biological system (i.e., a known or characterized cell type) a population of polynucleotides comprising the RTUs disclosed elsewhere herein. The activity of the trans-acting factors and/or the activity of the cis-regulatory elements are detected. As described elsewhere herein, a trans-acting factor activity profile or a cis-regulatory element activity profile for the biological system is generated, wherein the trans-acting factor activity profile or the cis-regulatory element activity profile comprises values representing the level of activity of one or more trans-acting factor and/or one or more cis-regulatory element that is present in the biological system. This profile of trans-acting factor activity and/or cis-regulatory element activity can be used as a reference profile to characterize various biological systems. Once the reference profile for a particular reference biological system is established, it may be used to determine whether an uncharacterized biological system is of the same biological system (i.e., cell type and/or in the same disease state) as the reference biological system. A trans-acting factor activity profile or a cis-regulatory element activity profile from the biological system of interest is compared to the reference profile to determine whether the trans-acting factor activity profile and/or the cis-regulatory element activity profile of the biological system of interest is sufficiently similar to the reference profile. Alternatively, the trans-acting factor activity profile and/or the cis-regulatory element activity profile of the test biological system is compared to a plurality of reference profiles to select the reference profile that is most similar to the trans-acting factor activity profile or the cis-regulatory element profile of the biological system of interest.

In specific embodiments, the population of RTUs used to generate the reference profile comprises at least one or more calibrating RTUs. The level of trans-acting factor activity or cis-regulatory element activity is thereby normalized against the level of reporter species from the calibrating RTUs. It is recognized that a calibrating RTU need not be included, and the relative activity of the various trans-acting factors or cis-regulatory elements can be determined and subsequently compared to the relative activity of the same trans-acting factors or cis-regulatory element in the sample.

In other methods, when the population of polynucleotides is stably incorporated into the genome of embryonic stem cells, reporter transgenic animals are generated that enable monitoring the activity of a trans-acting factor and/or a cis-regulatory element of interest in different tissues during embryonic and postnatal development, and in various experimental models of diseases (Gilthorpe et al. (1999) Methods Mol Biol. 97:159-182 and Trainor et al. (1999) *Methods Mol Biol.* 97:183-200).

A method is provided for identifying a cell type. The method comprises providing one or more reference profiles, wherein each reference profile is characteristic of a particular type of cell and/or disease state and comprises values representing the levels of at least two trans-acting factors or at least two cis-regulatory elements in the cell type and/or disease state. A trans-acting factor activity profile or a cis-regulatory element activity profile for the cell of interest and/or the disease state of interest is also provided. The profile comprises values representing the activity of two or more trans-acting factors and/or cis-regulatory elements for which values are also comprised within the reference profiles. It is then determined if the trans-acting factor activity profile or the cis-regulatory element activity profile from the cell of interest and/or the disease state of interest is similar to one or more reference profiles to thereby identify the cell type and/or the disease state.

The strength of the correlation between the reference profile and the trans-acting factor activity profile or the cis-regulatory element activity profile may be determined by a statistical test of significance. Such statistical tests provide a score indicating the strength of the correlation between the two profiles. Such scores may be used to select one or more trans-acting factors or cis-regulatory elements whose activity has the greatest correlation with a particular cell type in order to increase the diagnostic or prognostic accuracy of the trans-acting factor activity profile or the cis-regulatory element activity profile, or in order to reduce the number of values contained in the trans-acting factor activity profile or the cis-regulatory element activity profile while maintaining the diagnostic or prognostic accuracy of the trans-acting factor activity profile or cis-regulatory element activity profile.

Reference profiles may be used to identify a wide variety of samples. For example, reference profiles may be used to identify a variety of cell types including embryonic stem cells, and cells or cell lines derived from the spleen, lung, colon, liver, uterus, endometrium, brain, skin, bone marrow, heart, blood vessels, thymus, kidney, breast, testis, prostate, thyroid, skeletal muscle, pancreas, small intestine, or ovary. Other cells of interest include T-cells, B-cells, and bone-forming cells (osteoprogenitor cells, osteoblasts, and osteocytes). In addition, biopsy samples, autopsy samples, or slice tissue culture from any organ or tissue can be used. Additional cell lines of interest also include the mammalian 293, Hela cell lines, CHO cell lines, and COS cell lines.

Reference profiles may also be used to identify normal versus pathologic cells; cells at different stages of development or differentiation; or cells in different parts of the cell cycle. Pathologic cells or disease states that can be identified in the methods of the invention include, but are not limited to, aging, headaches, cardiac hypertrophy, muscular dystrophy, catabolic disorders, Diabetes Type 1, Diabetes Type 2, hypercholesterolemia, atherosclerosis, heart disease, ischemia/reperfusion, angina pectoris, pulmonary disease, acid-included lung injury, chronic obstructive pulmonary disease (COPD), renal disease, leptospiriosis renal disease, gut diseases, skin diseases, incontinentia pigmenti, asthma, arthritis, Crohns disease, ocular allergy, appendicitis, pancreatitis, periodonitis, inflammatory bowel disease, sepsis, silica-induced, sleep apnoea, AIDS (HIV-1), autoimmunity, Lupus, neuropathological diseases, or Alzheimer's disease.

Cancerous cells can also be identified in the methods of the invention. As used herein, the terms "cancer," "hyperproliferative," and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair. Various cancerous cells can be identified or characterized in the methods of invention, including, but not limited to, breast, cervix, ovary, vulva, prostate, kidney, liver, pancreas, esophygeal/gastric, stomach, colon, thyroid, melanoma, head and neck, cylindromatosis, oral carcinoma, astrocytoma/glioblastoma, neuroblastoma, Hodgkin's lymphoma, acute lymphoblastic leukemia, acute myelogenous leukemia, acute T-ell leukemia (HTLV-1), chronic lymphocytic leukemia, Burkitts lymphoma (EBV), Mantle cell lymphoma, multiple myeloma, diffuse large B-cell lymphoma.

By examining the profiles of transcription factor activities in biological systems with pathologies, the methods of the invention can, for example, be used for identifying and diagnosing the molecular signatures of those pathologies. For example, as demonstrated in the working examples present herein, cancer cells have distinct patterns of transcription factor activities, allowing the differential analysis of cancer cell lines, even those derived from the same type of tissue.

Thus, methods provided herein can be used to identify signal transduction/transcription factor pathways that play a pivotal role in particular types and stages of pathology. By comparing the profiles of multiple transcription factors in pathologic and normal cells, it is possible to discover alterations in signal transduction underlying particular pathologies. Moreover, such profiles are useful for diagnosing a pathology present in an organism, including a person.

The methods are also useful for identifying diagnostic markers of disease. Trans-acting factor activity and/or cis-regulatory element activity that varies in a cell sample or a diseased cultured cell compared to normal samples or cells may be used as a diagnostic markers. In general, it is best to compare samples from a statistically significant sample population with normal samples. In this way, information can be pooled to identify diagnostic markers common to all or a significant number of cells exhibiting the pathology. A trans-acting factor activity profile or a cis-regulatory element activity profile may also indicate the presence of a particular pathogen or pathogen strain in the cell, or may be correlated with and used to predict susceptibility to a particular disease or susceptibility to undesirable side effects in response to a given therapy.

In specific methods, transgenic animals having the population of polynucleotides comprising the RTUs can be used for profiling trans-acting factor activities and/or cis-regulatory element activities in various tissues, cells, and organs in postnatal development and to investigate the effects of different treatments (such as administering various compounds, stress, pathogens, pain stimuli, various diseases, tumor transformation, etc.) in vivo in whole animals.

In still other methods, the population of polynucleotides comprising the RTUs can be used to identify the trans-acting factors and/or cis-regulatory elements that are the primary targets of various inducers of cell activation. In this method, the population of polynucleotides comprising the RTUs is transiently or stably transfected into the cells. The transfected cells are pre-treated with an inhibitor of protein synthesis and are stimulated with the inducer of interest.

In other methods, the population of polynucleotides comprising the RTUs can be inserted into a gene delivery vehicle (for example, an adenoviral, a retroviral, or an adeno-associated vector) and introduced into cells for profiling the activities of trans-acting factors and/or cis-regulatory elements during the process of cell activation, transformation, differentiation, apoptosis, senescence, etc.

The compositions of the invention can also be used to determine the profile of trans-acting factor activity and/or the cis-regulatory element activity in a subject. In this method, the population of polynucleotides comprising the RTUs is inserted into an appropriate vector and transfected into a biopsy sample. Because gene transfer itself and reporter transcription occur quite rapidly (during one to two hours), it will be possible to determine the trans-acting factor activity profile and/or the cis-regulatory element activity profile while the explanted tissue retains its integrity. Also, owing to the high sensitivity of PCR detection, it is also possible to determine the profiles of trans-acting factors or the cis-regulatory element in small amounts of biological specimens.

In yet another method, the population of RTUs can be used to investigate the profiles of trans-acting factor activity and/or cis-regulatory element activity in embryonic development. In this method, the population of polynucleotides comprises the RTUs are introduced into the embryonic stem cell and implanted in utero. At different stages of development, the reporter embryo/fetus is microdissected and subjected to the analysis of trans-acting factor activity or cis-regulatory element activity.

The Human Genome Project has identified thousands of genes; for most of them, their biological functions are unknown. The present invention provides methods that allow newly discovered genes to be placed within a signal transduction/transcription factor network. Accordingly, a method for assessing the biological function of a polynucleotide or a polypeptide of interest in a biological system is provided. In this method, a biological system having a population of polynucleotides comprising the RTUs can be used to assess the effects of modulating the level/activity of a polynucleotide or a polypeptide of interest. By analyzing the profile of trans-acting factor activities and/or cis-regulatory element activities, it will be possible to determine the trans-acting factor pathways (i.e., signal transduction pathways) that are affected by modulation (increase or decrease) of the level and/or activity of a polynucleotide or polypeptide of interest.

In other embodiments, the methods and compositions of the invention can be used for analyzing phenotypical changes in animals having alteration in the polynucleotide or polypeptide of interest at the level of signal transduction. For example, a population of RTUs can be introduced in vitro into cells derived from animals having the alteration in the polynucleotide or polypeptide of interest in order to compare the profile of activities of cis-regulatory sequences and/or the trans-acting factors in the altered cells with that of the wild-type cells. This method thereby allows the identification of the biological function of the polynucleotide or polypeptide in a given trans-acting factor pathway (i.e., signal transduction) to be determined.

In other embodiments, the reporter animals (as described above) can be used for assessing effects of inactivation or overexpression of a gene of interest in different tissues of whole animals. In this embodiment, the reporter animals having the population of RTUs stably incorporated into their genome are crossed with animals, in which the level and/or activity of the polypeptide or polynucleotide is decreased or increased. By analyzing the expression of the RTUs in the resulting animals, one can establish the biological function of the polypeptide or the polynucleotide of interest in a trans-acting factor pathway (i.e., a signal transduction pathway) in different organs and tissues.

It is recognized that a variety of alterations can be made in the polynucleotide or polypeptide of interest for the assessment of its function. For example, the alteration can result in a decrease in the activity of the polypeptide or polynucleotide. Such alterations include, but are not limited to, genetic knock-out, treatment with an antisense sequence, an interfering RNA, expression of a dominate negative mutation, or any other means that can inhibit the activity/level of the polynucleotide or polypeptide of interest. In other embodiments, the alteration results in an increase in activity or level of the polypeptide or polynucleotide of interest. Such alterations include, but are not limited to, over expression of the polynucleotide, expression of a dominate-positive mutant, or any other means that increase the level and/or activity of the polynucleotide or polypeptide of interest.

Monitoring the influence of various treatments, including, for example, agents (e.g., drugs, compounds) on the activity of trans-acting factors and/or cis-regulatory elements can be applied not only in basic drug screening but also in clinical trials. For example, reference profiles can be generated for both the normal state and the diseased state. The effectiveness of a treatment can be monitored in clinical trials of subjects by monitoring the trans-acting factor activity profile and/or the cis-regulatory element profile of the subject and comparing that profile to the reference profile of the normal and the diseased state.

Any treatment of interest can be employed in the various methods of the invention. In specific embodiments, the treatment comprises exposing the biological system to a physical stimulus, a mechanical stimulus, a chemical stimulus, or a biological stimulus. In still other methods, the treatment comprises exposing the biological system to an organic molecule, an inorganic molecule, a polypeptide, a polynucleotide, a polysaccharide, ionizing radiation, an electromagnetic field, gravity, or pressure. In one embodiment, the treatment is a chemotherapeutic agent.

In one method, a method for monitoring the effectiveness of treatment of a subject comprising the steps of (1) obtaining a preadministration cell sample from a subject prior to administration of the treatment; (2) detecting the activity of the trans-acting factors or cis-regulatory elements in that sample and thereby generating a trans-acting factor activity profile and/or a cis-regulatory element activity profile; (3) obtaining one or more post treatment samples from the subject; (4) detecting the activity of the trans-acting factors and/or cis-regulatory element in that sample and thereby generating a trans-acting factor activity profile and/or a cis-regulatory element activity profile; (5) comparing the trans-acting factor activity profile or the cis-regulatory element activity profile of the post-treatment cell sample with the pre-treatment sample cell or samples and/or comparing the post-treatment cell sample with a reference profile previously generated from either a healthy or diseased state; and (6) altering the treatment to the subject accordingly to bring about the desired effect, i.e., for example, an appropriate modulation of the trans-acting factor activity or cis-regulatory element activity. Thus the methods of the invention find use in evaluating drug toxicity and effective drug dosages.

A method to monitor the function of a cell type of interest in a biological system is provided comprising the steps of (1) providing cells having a population of polynucleotides comprising the RTUs of the invention, wherein the activity of the cis-regulatory element in the population of polynucleotides is modulated in the presence of the corresponding trans-acting factor; (2) introducing the cells into the biological system of interest; (3) detecting the activity of the trans-acting factors and/or cis-regulatory elements in that biological system and thereby generating a first trans-acting factor activity profile and/or a first cis-regulatory element activity profile for the biological system; (4) at a later developmental time point or following a treatment of interest detecting the activity of the trans-acting factors and/or cis-regulatory elements in the biological system and thereby generating a second trans-acting factor activity profile or a second cis-regulatory element activity profile for the biological system (5) determining whether the first cis-regulatory element activity profile is similar to the second cis-regulatory element activity profile and/or determining whether the first trans-acting factor activity profile is similar to the second trans-acting factor activity profile to thereby assess temporal and causal alterations in the profiles of the cis-regulatory element activities and assess the function of said cell type within the biological system.

5.3.3. Assaying for Treatments that Modulate Trans-Acting Factor Activity and/or Cis-Regulatory Element Activity Methods and compositions to screen for various treatments that modulate the activity of a trans-acting factor or a cis-regulatory element are provided. The methods and compositions can be used to identify the effects of various treatments, including both desirable and undesirable biological effects. The methods and compositions of the invention can be used to assess the effect of a treatment on the activity of at least one trans-acting factor and/or at least one cis-regulatory element. In this method, a biological system having a population of RTUs of the present invention is provided. The biological system is subject to a treatment of interest, and subsequently, the reporter species of the reporter sequences are processed. In certain embodiments, at least two of the processed reporter species are detected. This method allows the identification of a treatment that modulates the activity of at least one trans-acting factor and/or at least one cis-regulatory element. Treatments identified by this method can either increase or decrease the level of the reporter species. In some embodiments, detected amounts of a processed reporter species are compared to a standard or reference profile to identify a treatment that modulates the activity of a trans-acting factor and/or cis-regulatory element.

Any treatment of interest can be employed in the methods of the invention. In specific embodiments, the treatment comprises exposing the biological system to a physical stimulus, a mechanical stimulus, a chemical stimulus, or a biological stimulus. In still other methods the treatment comprises exposing the biological system to an organic molecule, an inorganic molecule, a polypeptide, a polynucleotide, a polysaccharide, ionizing radiation, an electromagnetic field, gravity, or pressure. In some embodiments, the treatment is a chemotherapeutic agent. In certain embodiments, the biological system is exposed to a known drug.

In certain embodiments, the methods of the invention have applications as screening methods for cancer treatments. To this end, a set of standard chemotherapy drugs can be screened, for which large arrays of data are available. For example, for a number of cell lines derived from carcinomas, 20 to 30 or more drugs that kill the particular cell line, and an equal number of reference drugs that do not affect the cell viability can be selected. The alterations in the profiles of transcription factors that occur upon drug treatment are assessed and used to generate a novel database of molecular signatures of these drugs. The database system is then utilized as a reference profile to compare to profiled of screened chemical libraries with the purpose of identification of potential anti-cancer drug candidates.

When the biological system of interest comprises a cell and the treatment comprise a candidate compound, various methods can be employed to contact the candidate compound to the cell, including, for example, incubating the candidate compound in the cell culture medium, administering the candidate compound to an animal having the cell, or introducing the candidate compound (or a nucleotide sequence encoding the candidate compound) into the cell or a subject having the cell. Such methods are known in the art and discussed elsewhere herein.

The methods and compositions of the invention are also useful in examining two identical biological systems exposed to different treatments. For example, the method is useful in toxicology screening and/or testing compounds for the ability to modulate gene expression in a cell. In such a method, one sample is exposed to the candidate compound, and the other cell is not. Then, the trans-acting factor activity profile and/or the cis-regulatory element profiles of the samples are generated and compared.

Candidate compounds that may be screened to identify modulators of cis-regulatory element activity include any molecule, for example, small inorganic molecules and small organic molecules (e.g., molecules obtained from combinatorial and natural product libraries). Such molecules include, for example, polypeptides (including antibodies and peptides), as well as, nucleic acid molecules, or polysaccharides. It is recognized that the candidate compounds encompass numerous chemical classes.

In specific methods, the candidate compound is a polypeptide such as a signaling molecule (i.e., a kinase). By analyzing the profile of the trans-acting factor activities, it is possible to determine the trans-acting factors preferentially activated by the signaling molecule. Similarly, the compositions of the invention can be used to assess how the selective inhibition of certain signaling pathways (e.g., by expressing DNA mutant cDNAs or by treating cells with selective chemical inhibitors) influences different trans-acting factors.

As will be appreciated by those in the art, candidate compounds can be obtained from a wide variety of sources, including libraries of synthetic and natural compounds. Thus, the methods disclosed herein provide a rapid and easy method for screening any library of candidate compounds. Examples of methods for the synthesis of molecular libraries can be found in the art, for example in DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carell et al. (1994) *Angew. Chem. Int. Ed. Engl.* 33:2059; Carell et al. (1994) *Angew. Chem. Int. Ed. Engl.* 33:2061; Gallop et al. (1994) *J. Med. Chem.* 37:1233; and Ghose and Vishwanadhan, eds. (2001) *Combinatorial Library Design and Evaluation: Principles, Software Tools, and Applications in Drug Discovery* (Marcel Dekker, New York), WO94/24314, and WO94/24314, each of which is herein incorporated by reference in its entirety.

As discussed above, compositions include transgenic animals having the population of polypeptides comprising the RTUs corresponding to the trans-acting factor or cis-regulatory element. Thus, candidate compounds can be administered to the transgenic animal and the activity of the trans-acting factors of interest detected. Thus, methods are provided that enable high throughput in vivo drug screening.

In some embodiments, methods of determining whether an individual in a pathologic state is likely to be responsive to a therapy are provided. For example, a RTU population can be introduced into a cell contributing to the pathology of the individual (such as, for example, a cell removed from the individual in a biopsy, or, as another example, a cultured cell line typically used as a model for the pathology afflicting the individual), and, after contacting the cell with a potential therapy, the reporter species can be processed and detected to generate a profile that can be compared to a reference profile, thereby determining whether the individual in a pathologic state is likely to be repsonive to a therapy where similarities or differences in the profiles are observed.

5.3.4. Method for Determining the Size of a Cell Population

Method for determining the size of a cell population of interest in a mixture of cell populations is provided. These methods employ polynucleotides comprising DNA constructs comprising a reporter sequence having a processing tag that can distinguish various reporter sequences from one another are provided. Populations of such DNA constructs are also discussed above.

The method for determining the size of a cell population comprises (1) providing two or more cell populations, wherein the cells in each cell population comprises a unique reporter sequence, each of the reporter sequences comprise a common processing tag in the reporter sequence, the position of the processing tag is different in each of the reporter sequence, and the processing tag can distinguish each of the reporter sequence in the cell populations; (2) combining the cell populations; (3) subjecting the combined cell population to a treatment of interest; (4) processing the reporter sequences; and, (5) detecting the processed reporter sequences and thereby determining relative abundances of the cell populations. Treatments of interest, processing tags, cell populations and other compositions and methods for the practice of this embodiment are discussed in detail elsewhere herein.

6. EXAMPLES

The following examples are provided to illustrate aspects of the invention, and are not intended to limit the scope of the invention in any way.

6.1. Example 1

Materials and general procedures used in the examples that follow are described below.

Nucleic acid manipulations. Manipulations with nucleic acids were performed using standard molecular biology techniques known in the art, as described, for example, in Sambrook and Russell, *Molecular Cloning: A Laboratory Manual*, 3$^{rd}$ Ed. (Cold Spring Harbor Laboratory Press, Cold Spring Harbor, N.Y., 2001) and *Current Protocols in Molecular Biology* (Ausubel et al., eds., John Wiley & Sons, 1994-1998, Current Protocols, 1987-1994, as supplemented through July 2005 (Supplement 71)). Oligonucleotides were ordered from Integrated DNA Technologies (Coralville, Iowa, USA).

Cells. HEK293, 239, HCT116, SW480, HepG2 and MDA-MBA-231 cells were maintained on DME media (Invitrogen, Carlsbad, Calif., USA) supplemented with 10% FBS (HyClone, Logan, Utah, USA) and antibiotics. Human recombinant TNFα and IL-1β were purchased from Roche (Roche Diagnostics, Mannheim, Germany). Etoposide, Forskolin, 3,3',5-Triiodo-L-thyronine (T3), 25-dihydroxyvitamin D3, estradiol, dexamethasone and 4α-Phorbol 12-myristate 13-acetate (PMA) were purchased from Sigma (Sigma-Aldrich, St. Louis, Mo., USA). 1,4-Diamino-1,4-bis (2-aminophenylthio)-butadiene (U0126) was obtained from A.G. Scientific (San Diego, Calif., USA). A2

Transfections. Cells to be transfected were plated at a subconfluent density (1×10$^6$/well) in wells of a 6 well plate. Eighteen hours later, cells were transfected with FUGENE® 6 reagent (Roche Diagnostics, Mannheim, Germany) that was mixed with plasmid DNA at a ratio of 3.0 μl/1.0 ∞g of total plasmid DNA for each transfection, according to the manufacturer's protocol. The day after transfection, the medium was replaced with one ml of fresh growth medium.

Isolation of cellular RNA. Total cellular RNA was isolated by using TRIZOL® reagent (Invitrogen, Carlsbad, Calif., USA) according to the manufacturer's protocol and re-dissolved in water. Routinely, 1 ml of the TRIZOL® reagent was used to extract RNA from the confluent monolayer of cells in a well of a 6-well plate.

Reverse transcriptase-polymerase chain reaction (RT-PCR). Samples of total RNA were treated with DNAse I (Ambion, Austin, Tex. USA) according to manufacturer's instructions. Residual DNAse was heat inactivated at 70 C. for 15 mm. The DNAse-treated RNA was reversely transcribed by using oligo-dT polynucleotides and Mo-MLV reverse transcriptase (Invitrogen, Carlsbad, Calif., USA)

according to the manufacturer's instructions. One tenth of the reversely transcribed RNA was amplified in a PCR reaction, by using Taq DNA polymerase (Invitrogen Carlsbad, Calif., USA) and the following reporter sequence-specific primers: (forward primer: 1: 5'-AAATACGAGATCCAC-CGAGACTCC-3'(SEQ ID NO: 11) and reverse primer 2: 5'-GCAGGAACAGCGCCGATACAAT-3'(SEQ ID NO:12)). PCR reactions were performed on a ABI 9700 GENEAMP®thermo-cycler. The cycling parameters were: 20 s at 95° C., 20 s at 65° C., and 2 min at 72° C.

Labeling of PCR products. One tenth of each completed PCR reaction was diluted with a fresh PCR reaction mixture containing 6-carboxyfluorescein (6-FAM) 5'-labeled reporter polynucleotide-specific primer (primer 2: 5'-GCAGGAA-CAGCGCCGATACAAT-3' (SEQ ID NO: 12)) and then incubated at 95° C. for 2 min, at 68° C. for 20 sec and at 72° C. for 10 min.

Endonuclease restrictions. Hpa I restriction endonuclease (New England Biolabs, Ipswich, Mass., USA) was directly added to the labeled PCR products at concentration of 5 U/reaction. The samples were digested for 2 hrs and purified using QIAQUICK® PCR purification columns (Qiagen, Hilden, Germany) according to the manufacturer's protocol.

Capillary electrophoresis. Serial dilutions of each Hpa I digested sample were analyzed by capillary electrophoresis using ABI PRISM® 3100 genetic analyzer (Applied Biosystems, Foster City, Calif., USA). A set of X-rhodamine-labeled MAPMARKER® 1000 molecular weight standards (Bio-Ventures, Murfreesboro, Tenn., USA) was run in parallel to the analyzed samples as a molecular weight reference.

Capillary electrophoresis data analysis was performed using either GENSCAN® software (Applied Biosystems, Foster City, Calif., USA), or ATTAGRAPH™ software (Attagene, N.C., USA).

6.2. Example 2

This example demonstrates the construction of several individual RTUs for assessing multiple transcription factor activities. In particular, this example demonstrates the use of a secreted alkali phosphatase (SEAP) gene sequence to prepare 32 reporter sequences each having a HpaI endonuclease cleavage site processing tag located at a position that is different from the processing tag positions in the other reporter sequences. A8 pSEAP2-control plasmid vector that comprises SEAP gene was purchased from Clontech (Palo Alto, Calif., USA). The HpaI endonuclease cleavage sites were created at various positions of the transcribed region of the SEAP gene using PCR based in vitro site directed mutagenesis. Briefly, a set of 32 pairs of self-complementary oligonucleotide primers was synthesized, wherein each individual pair of primers comprises sequence homologous to distinct region of the SEAP gene interrupted by the HpaI cleavage site. To produce each individual HpaI-tagged reporter polynucleotide, 100 ng of the pSEAP2-control DNA was used as a template in a PCR reaction containing 1 x Pfu buffer (Stratagene, La Jolla, Calif., USA), 200 µM of each four dNTP, 20 pM of each of the two self-complementary SEAP specific primers containing HpaI cleavage site, and 2 u of Pfu polymerase (Stratagene, La Jolla, Calif., USA). The PCR was performed in total volume of 50 µl for 12 cycles. The cycling parameters were: 20 s at 95° C., 20 s at 55° C., and 10 min at 68° C. To remove the original pSEAP2-control plasmid DNA template, the completed PCR reactions were treated for 2 hrs with 10 units of DpnI restriction enzyme (New England Biolabs, Ipswich, Mass., USA) in the same 1 x Pfu buffer. Aliquots of the DpnI-treated reactions were used to directly transform ULTRAMAX™ efficiency DH5alpha E. coli competent cells (Invitrogen, Carlsbad, Calif., USA). Mini preparations of plasmid DNA were isolated from bacterial clones and analyzed by HpaI restriction digest to confirm emergence of the HpaI sites. All 32 reporter polynucleotides generated in this example were sequence verified. Sequences of the parental SEAP reporter sequence (SEQ ID NO:13) and the 32 reporter sequences with processing tags (SEQ ID NOS:14-45) are provided in FIG. 11A-K.

6.3. Example 3

This example demonstrates the preparation of a population of distinguishable RTUs having comparable transcription efficiencies.

The 32 reporter sequences described in the previous example were sub-cloned into a plasmid with a constitutive, simian virus 40 derived, 5V40 promoter. The resulting RTU library (termed SV40-RTU) comprised 32 individual reporter constructs, wherein each construct comprises an identical SV40 promoter operatively linked to a reporter sequence with differentially positioned HpaI processing tag (FIG. 12A). An equimolar mixture of the individual SV40-RTUs was transiently transfected into human kidney epithelial HEK293 cells as described in Section 6.1 above. The following day, total cellular RNA was isolated, as described in Section 6.1 above, and samples containing 5 µg of total RNA were treated with DNAse I for one hour at 37 ° C. followed by incubation at 70 ° C. for 15 min, to inactivate residual DNAse activity. One µg of the DNAse-treated RNA was used as a template in reverse transcription (RT) reaction containing 1 ×RT buffer (Invitrogen, Carlsbad, CA, USA), 1 µg of oligo-dT primer (comprises 16 thymidine residues), 500 µM of each four dNTP and Mo-MLV reverse transcriptase (Invitrogen, Carlsbad, CA, USA) in a total volume of 20 µl. RT reactions were performed at 42° C. for 1 hour following additional incubation at 75 ° C. for 20 min, to inactivate residual activity of the reverse transcriptase. Two µl aliquots of the reversely transcribed RNA were used as a template in a PCR reaction containing 1 ×PCR buffer (Invitrogen Carlsbad, CA, USA), 200 µM of each four dNTP, 20 pM each of the forward primer 1 (SEQ ID NO:11) and reverse primer 2 (SEQ ID NO:12) described above, and 0.2 units of Taq DNA polymerase (Invitrogen Carlsbad, CA, USA) in total volume of 50 µl. The PCR reactions were performed for 30 cycles on the ABI 9700 GENEAMP® thermo-cycler with cycling parameters as described in Section 6.1 above. The amplified reporter sequences were fluorescently labeled by diluting 5 µl aliquots of each completed PCR reaction with 45 µl of fresh PCR reaction mixture supplemented with 20 pM of 6-Carboxy-fluorescein (6-FAM) 5'-labeled reporter polynucleotide-specific primer 2 (SEQ ID NO: 12) as described in Section 6.1 above. Hpa I restriction endonuclease reactions and capillary electrophoresis were performed on the labeled PCR reaction products as described above. Electrophoregrams were acquired and analyzed using GENSCAN® fragment analysis software. On the electrophoregram, each individual reporter polynucleotide is detected as a peak of 6-FAM fluorescence intensity position of which is determined by the position of the HpaI processing tag within the reporter nucleotide (FIG. 12B).

The relative activities of individual RTUs were calculated as the fluorescence values of corresponding individual peaks on the electrophoregram and normalized on the mean value of all reporter peaks. (FIG. 12C). Twenty-six reporter sequences of the 32 reporter constructs were expressed with approximately equal efficacy deviating less than 20% from average expression levels, while 6 constructs (labeled nos. 7, 14, 22, 23, 26, and 31 in FIG. 12C) had substantially different levels of expression. The 26 selected reporter sequences were used for constructing libraries of multiple transcription factor RTUs used in examples provided below.

6.4. Example 4

This example demonstrates that a population of RTUs as provided herein exhibits fidelity to the particular trans-factor activities present in a cell, that profiles of reporter species of the RTU population are reproducible, and that variations in the preparation of reporter species for detection can be accommodated using the RTU population of the present invention.

6.4.1. Constructing a Library of 15 RTUs

Fifteen of the HpaI-tagged reporter sequences, described in the previous example, that exhibited equal transcription efficiencies were used to prepare a population of RTUs by inserting each reporter sequence into a construct with one of 15 different cis-regulatory elements, in this case, promoters. The promoters of the RTUs (with terms for the individual RTUs in parentheses) contained (1) concatamers of binding sites for transcription factors NF-κB (Zabel et al (1991) *J. Biol. Chem.* 266:252-260; Baldwin et al. (1991) *Mol Cell Biol.* 11:4943-4951) (NF-κB RTU), p53 (Funk et al. (1992) *Mol Cell Biol.* 12(6):2866-71) (p53 RTU), or cAMP response element (CRE) (Benbrook and Jones (1994) *Nucleic Acids Res.* 22:1463-1469) (CRE RTU); (2) multiple binding sites for nuclear receptors PPARα (Evans et al. (2004) *Nat Med.* 10(4):355-361) (PPRE RTU), estrogen receptor (ER) (Naar et al. (1991) *Cell* 65(7):1267-1279) (ERE RTU), glucocorticoid receptor (GR) (McEwan (1997) *Bioessays* 19(2):153-160) (GRE RTU), aryl hydrocarbon receptor (AhR) (McLane and Whitlock (1994) *Receptor* 4(4):209-222) (AHR RTU), or pregnane X receptor (PXR) (Lehmann et al. (1998) *J Clin Invest.* 102(5):1016-1023) (PXR RTU); (3) synthetic promoters inducible by INFγ (ISRE) (Kessler et al. (1990) *Genes Dev* 4:1753-1765) (ISRE RTU), TCf/β-catenin signaling (van der Wetering et al. (1997) *Cell* 88(6):789-799) (Tcf/β-cat RTU), TGFβ signaling (Dennler et al. (1998) *EMBO J.* 17(11):3091-3100) (TGFβ RTU), heat shock proteins (Kroeger and Morimoto (1994) *Mol. Cell. Biol.* 14:7592-7603) (HSE RTU), or by bone morphogenic protein (BMP) signaling (Korchynskyi and Dijke (2002) *J Biol Chem* 277(7):4883-91) (BRE RTU); or (4) a modified metal-inducible metallothionein (MT) promoter (Makarov et al. (1994) *Nucleic Acids Res* 22(8): 1504-1505; Koizumi et al. (1999) *Eur J Biochem.* 259(3):635-642) (MTΔ RTU); or a retinoblastoma-specific repressor element (Robbins et al. (1990) *Nature* 346(6285): 668-671) (pRb RTU). Additional details regarding these promoters is provided in Table 2. In addition, two constitutive CMV RTUs were constructed containing the cytomegalovirus promoter. The CMV RTUs, along with three viral SV40 RTUs, were used for calibration and normalization purposes. The inducibility of each individual RTU by corresponding inducers (e.g., TNFα and IL-1β for NF-κB RTU, forskolin for CRE RTU, IFNγ for ISRE, etc.) was tested in a transient reporter assay using RT-PCR.

TABLE 2

| Transcription factor/ co-activator | cis-element or promoter region | SEQ ID NO: | Specific inducers | References |
|---|---|---|---|---|
| NF-κB | GGGAMTTYCC | 46 | IL-1β, TNFα | Zabel et al. (1991) J. Biol. Chem. 266: 252-260. |
| HSF1, 2 | AGAATGTTCT | 47 | heat shock | Kroeger and Morimoto (1994) Mol. Cell. Biol. 14: 7592-7603. |
| IRF1 | TAGTTTCACTTTCCC | 48 | INFα, γ | Kessler et al. (1990) Genes Dev. 4: 1753-1765. |
| p53 | GGACATGCCCGGGCATGTCC | 49 | DNA damage | Funk et al. (1992) Mol. Cell. Biol. 12(6): 2866-71. |
| pRb | region of human c-fos promoter | | growth signals | Robbins et al. (1990) Nature 346(6285): 668-71. |
| Tcf/b-cat | AAGATGAAAGGGGT | 50 | Wnt | Van de Wetering et al. (1997) Cell 88(6): 789-99. |
| SMAD3, 4 | AGCCAGACA | 51 | TGFβ | Dennler et al. (1998) EMBO J. 17(11): 3091-100. |
| SMAD4, 5 | GGCGCC/GAGC | 52 | BMP | Korchynskyi and Dijke (2002) J Biol Chem. 277(7): 4883-91. |
| CREB | TGACGTMA | 53 | cAMP, forskolin | Benbrook and Jones (1994) Nucleic Acids Res. 22: 1463-1469. |
| AhR | region of mouse CYP1A1 promoter | | Dioxin | McLane and Whitlock (1994) Receptor 4(4): 209-22. |

TABLE 2-continued

| Transcription factor/ co-activator | cis-element or promoter region | SEQ ID NO: | Specific inducers | References |
|---|---|---|---|---|
| PXR | region of human CYP3A4 promoter | | Rifampicin | Lehmann et al. (1998) J. Clin. Invest. 102(5): 1016-23. |
| PPARα | AGGACAAGGTCA | 54 | WY14643 | Evans et al. (2004) Nat. Med. 10(4): 355-61. |
| PPARδ | AGGACAAGGTCA | | GW742 | Evans et al. (2004) Nat. Med. 10(4): 355-61. |
| PPARγ | AGGACAAGGTCA | | Rosiglitasone | Evans et al. (2004) Nat. Med. 10(4): 355-61. |
| ER | GGTCACAGTGACCTAG GTCACAGTGACCTA | 55 | Estradiol | Naar et al. (1991) Cell 65(7): 1267-79. |
| GR | GCGGTACATTTTGTTC TAG | 56 | Dexamethazone | McEwan et al. (1997) Bioessays 19(2): 153-60. |
| MTF-1 | region of MTIIa promoter | | Zinc | Makarov et al. (1994) Nucleic Acids Res. 22(8): 1504-5. |

6.4.2. Fidelity of a RTU Population to Transcription Factor Activities

Eleven RTUs as described above (PPRE RTU, GRE RTU, ISRE RTU, MTΔ RTU, NF-kB RTU, CRE RTU, AhrE RTU, ERE RTU, HSE RTU, p53 RTU and BRE RTU) were mixed at an equimolar ratio. For calibration purposes, the population also contained three SV40 RTUs with distinct HpaI-tagged reporter sequences mixed at a ratio of 1:3:9. The library of RTUs was transiently transfected into HEK293 cells. Two days after transfection, the cells were stimulated for 6 hrs with either an NF-κB inducer, IL-1β (100 u per ml), CREB inducer, forskolin (1 μg per ml), or by $ZnCl_2$ (100 μM), a specific inducer of metal-sensitive MTΔ RTU. Total RNA was isolated from the cells and reporter transcripts were amplified by RT-PCR, fluorescently labeled, digested with HpaI, and resolved by capillary electrophoresis as described in Section 6.1 above.

Figure 13A:
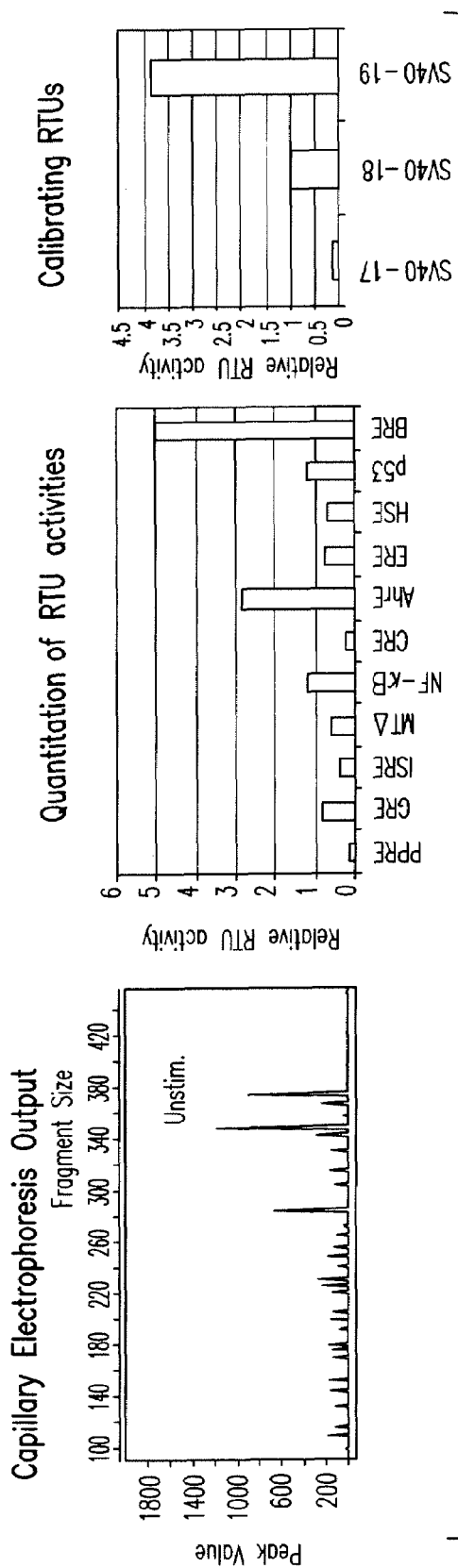
Figure 13B:
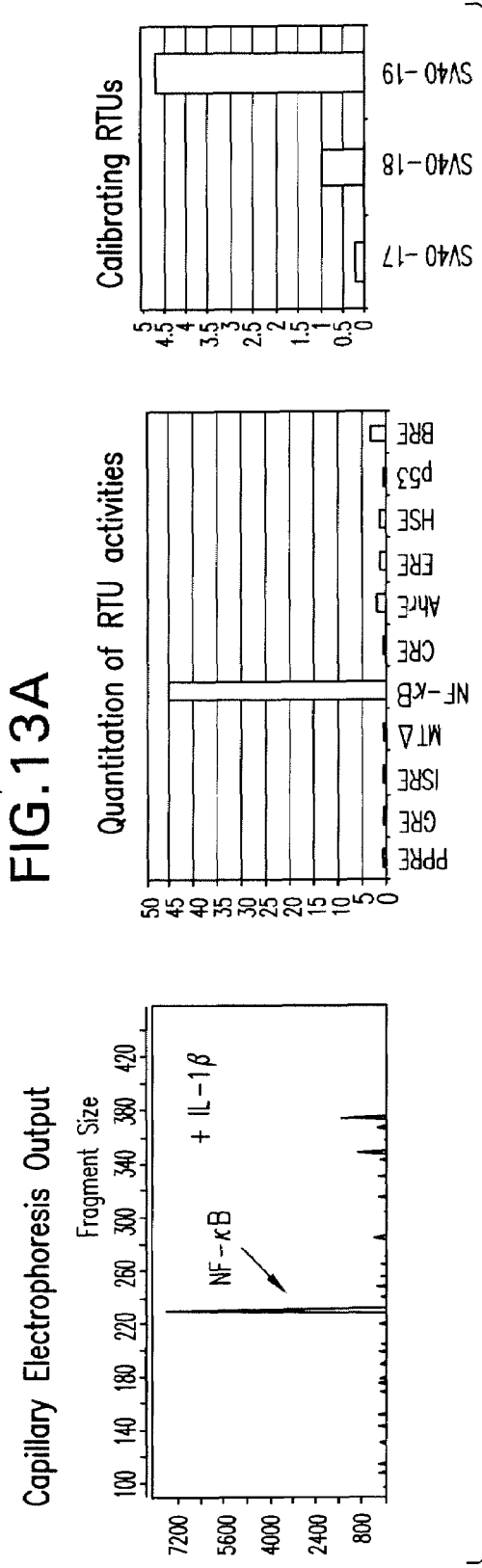
Figure 13C:
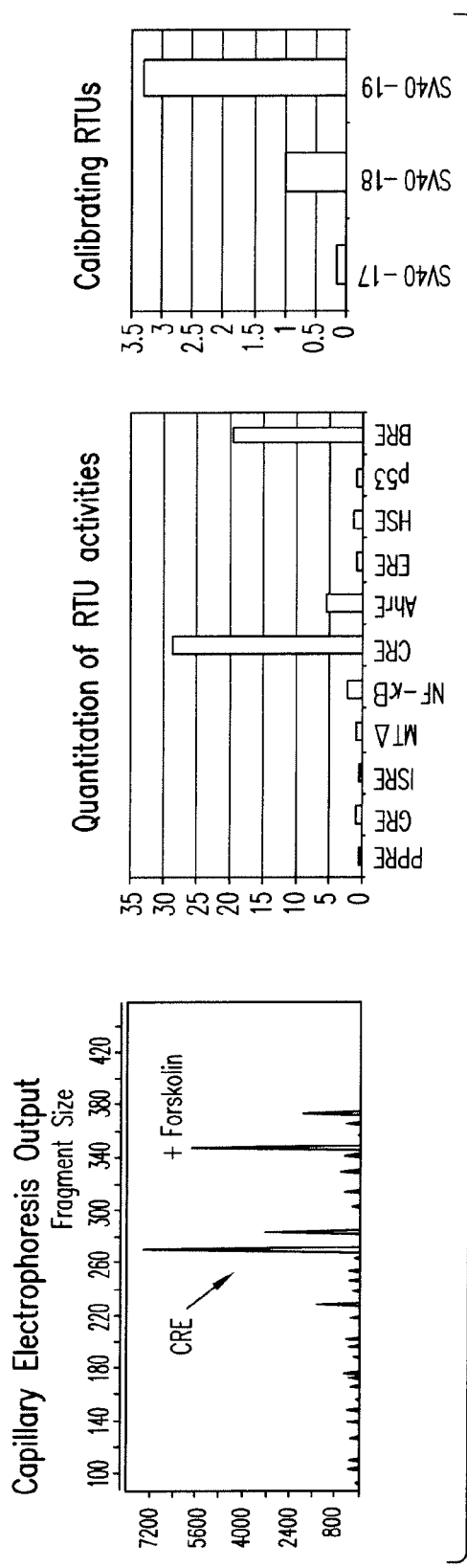
Figure 13D:
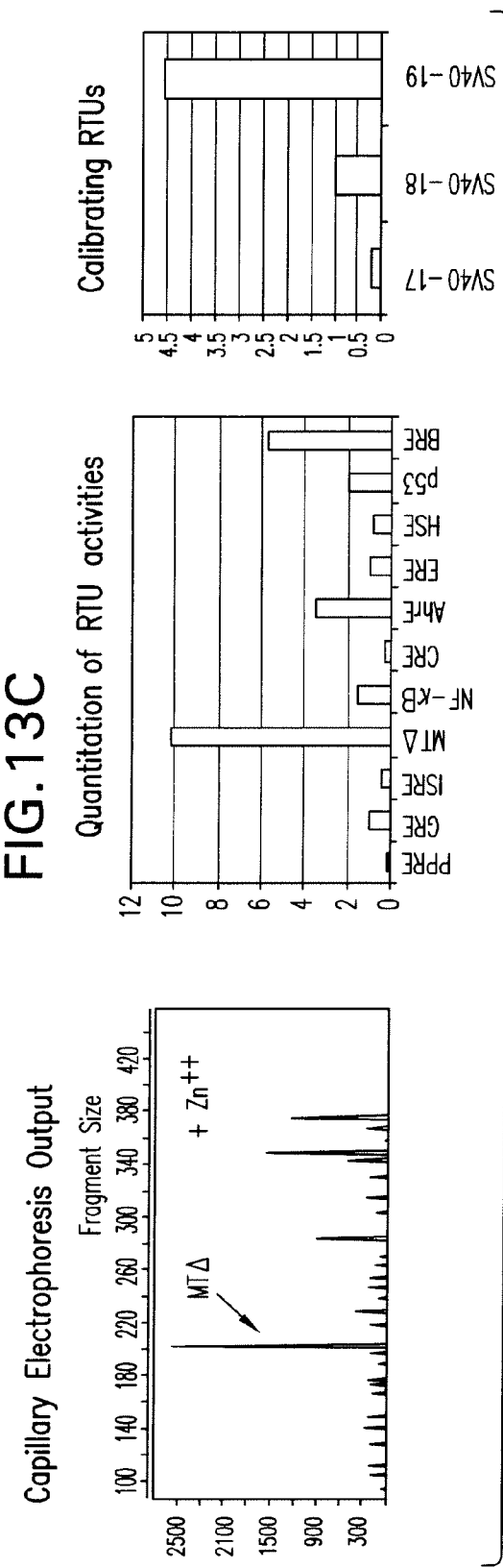
Figure 13E:
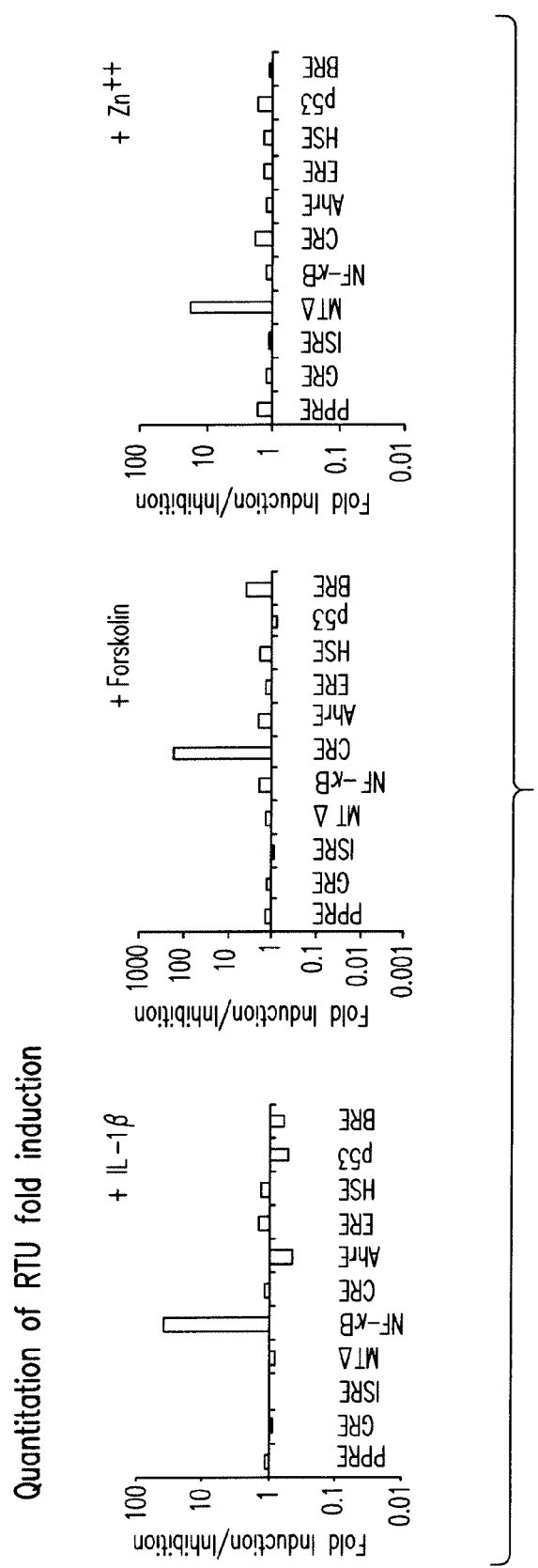

The electrophoretic profile of the HpaI-digested PCR products is shown in FIG. 13A-D (upper left panels). Relative values of transcriptional activities of individual RTUs were evaluated based on the corresponding peak values. To control for the linearity of PCR amplification, individual peak values were calculated by using the calibration curve that was derived from the three calibrating SV40 RTUs (upper right panels in FIG. 13A-D). To provide a quantitative assessment of changes in activities of the individual RTUs, an internal normalization was introduced, where the activity of each RTU is divided on the sum of activities of all RTUs within the system (similar to the normalization procedure in cDNA array hybridization). The normalized activities of individual RTUs in stimulated cells (FIG. 13B-D, middle panels) were compared to that in unstimulated cells (FIG. 13A, middle panel). FIG. 13E represents the values of fold induction of individual RTUs in stimulated cells versus nonstimulated cells. For convenience, the fold-induction values are shown in a logarithmic scale. The negative log values indicate an inhibition (fold-induction<1), the positive log values indicate an activation (fold-induction>1).

These results demonstrate that NF-κB RTU was specifically activated in IL-1β stimulated cells, CRE RTU was specifically activated in forskolin-stimulated cells, and MTΔ RTU was induced in $ZnCl_2$ treated cells (FIG. 13E), which is consistent with activities of IL-1β, forskolin, and $ZnCl_2$. Thus, the RTU population exhibits significant fidelity with respect to transcription factor activities.

6.4.3. Demonstration of the Reproducibility of a RTU Population for Detecting Transcription Factor Activities To evaluate reproducibility of the production of reporter species by the methods of the present invention, results of several independent experiments were analyzed in which the basal activity profile of the 15 RTUs described in Section 6.4.1, above, was assessed in HCT 116 human colorectal carcinoma cells. The population of 15 RTUs was transiently transfected into HCT116 cells in separate tissue culture plates. Two days after transfection, total RNA was isolated and profiles of relative basal RTU activities were determined as described above.

Results shown in FIG. 14A demonstrate that the profiles obtained in two independent experiments are virtually identical. Standard deviations were less than 3%. This comparison has been repeated several times with other cells, with the same results. Considering that variations of conventional luciferase-based transcription assays are rarely less than 15 to 20%, those skilled in the art will recognize that this is remarkable reproducibility.

6.4.4. Demonstration that Uniform Results are Achieved Using a RTU Population as Provided Herein Despite Variations Such as Differing RNA Degradation, in Preparations of Reporter RNAs Performed in parallel, two cultures of 239 human kidney epithelial cells were each transfected by the population of 15 RTUs described in Section 6.4.1 above. Total RNA was isolated two days after transfection from each culture. Basal profile of the relative transcription factor activities was determined, following the procedures described above. Prior to performing reverse transcription, the total RNA integrity was assessed by agarose gel electrophoresis in the presence of Ethidium Bromide in samples of the total RNA obtained from each of the two cultures. (FIG. 14B, left panel). A significantly reduced intensity of staining of 28S ribosomal RNA fraction was observed in a sample from one of the cell cultures (sample #2 in FIG. 14B) as compared to the sample from the other cell culture (sample #1 in FIG. 14B), an indication of greater levels of RNA degradation in sample #2. Yet, profiles of the relative activities of individual RTUs obtained from both samples were essentially identical (FIG. 14B, right panel). This demonstrates the a RTU population of the present invention can achieve uniform results across different samples, despite variations in the preparations of reporter species.

6.4.5. Demonstration that Uniform Results Are Achieved Using a RTU Population as Provided Herein Despite Broad Variations in the Amount of Transfected RTUs This example demonstrates that highly reproducible profiles of trans-acting factor and cis-regulatory element activities can be obtained using a RTU population under extremely broad variations in experimental conditions. The example also demonstrates the very high sensitivity of the methods provided. In addition, the example demonstrates that the introduced RTUs do not interfere with the cellular machinery and thus a RTU population can provide adequate assessment of endogenous trans-acting factor and cis-regulatory element activity profiles.

A population of seventeen RTUs was assembled comprising an equimolar mix of fourteen inducible RTUs (PPRE RTU, TGFβ RTU, TCF/β-cat RTU, PXR RTU, GRE RTU, ISRE RTU, MTΔ RTU, NF-κB RTU, CMV RTU, CRE RTU, Ahr RTU, ERE RTU, p53 RTU and BRE RTU) as described above. In addition, three calibrating SV40 RTUs containing distinct HpaI-tagged reporter sequences were also included at the molar ratios of 1:3:9. The RTU population was transfected into HEPG2 cells in wells of a six-well tissue culture plate by using conditions similar to those described above. In one experimental condition, cells were transfected with 1 microgram of RTU plasmid DNA. In another condition, the plasmid RTU was diluted by 1,000 fold with an irrelevant plasmid DNA, and cells were transfected with 1 microgram of total plasmid DNA that contained 1 nanogram of the RTU plasmid DNA. Two days after transfection, total RNA was isolated and the profiles of relative basal RTU activities were determined as described above.

Upon processing and detecting reporter species, the relative amounts of reporter species were assessed. As shown in FIG. 14 C, despite the extreme variations in the amounts of transfected RTUs, the obtained profiles practically coincided, thus demonstrating the reproducibility and the sensitivity of the methods provided herein.

6.5. Example 5

This example demonstrates that a RTU population, as provided in this application, can be used to rapidly and accurately assess multiple transcription factor activities present in different cell types. Moreover, these results demonstrate that an activity profile generated from a RTU population in a given cell type can be used to identify the particular cell based upon particular activities observed to be absent and present in the profile.

The population of 15 RTUs, described in Section 6.4.1, was transfected into five different human cancer cell lines: HEK 293 epithelial kidney cells; HCT116 and SW480 colorectal cancer cells; MDA-MB-231 breast carcinoma cells; and HepG2 liver carcinoma cells. In each cell line, the activities of individual RTUs were assessed as described above and normalized by internal normalization on the sum of activities of all RTUs. The profiles of the relative activities of the 15 RTUs, including a calibrating CMV RTU and a SV40 RTU are shown in FIG. 15.

The profiles obtained correlate with literature reports. SW480 cells expected to have elevated levels of β-catenin protein and a high basal activity of a TCF/β-catenin reporter due to mutations in the APC tumor suppressor gene (Korinek et al. (1997) *Science* 275(5307):1784-7), showed the highest TCF/β-catenin RTU activity (FIG. 15). It is known that mutations resulting in a dominant-positive β-catenin protein occur in HepG2 cells (de la Coste et al. (1998) *Proc Natl Acad Sci USA* 95(15):8847-51) and in HCT116 cells (Morin et al. (1997) *Science* 275(5307): 1787-90), and results provided in FIG. 15 indicate elevated activity in these cell types.

The greatest highest basal NF-kB activity was found in MDA-MB-231 cells, which correlates with literature data (Nakshatri et al. (1997) *Mol Cell Biol.* 17(7):3629-39).

The p53 RTU profile also correlates with literature data. HepG2, HCT116, and 293 cells all have wt p53 protein and showed detectable p53 RTU activities, while p53-mutant SW480 and MDA-MB-231 cells showed very low or undetectable activities.

Accordingly, these results indicate that cancer cell can be identified according to the profiles of their basal transcription factor activities.

6.6. Example 6

This example demonstrates that the methods and compositions of the present invention can be used to detect and track alterations in the profiles of transcription factor activities in cancer cells contacted with anti-cancer drugs in regard of the drug and the cancer cell type. Moreover, this example demonstrates that activity profiles of an RTU population in a cell can be used to elucidate the signaling pathways operating in a particular cell.

To assess changes in the profiles of activities of transcription factors in cells treated with anti-cancer agents tumor necrosis factor alpha (TNFα) and etoposide (VP-16), HEK293, HCT116, SW480, HepG2 and MDA-MB231 cells were transfected with the population of 15 RTUs as described above. Two days after transfection, the cells were stimulated for six hours with either TNFα (20 ng/ml) or with etoposide (100 μg/ml). Following the stimulation, the reporter polynucleotides were detected and normalized values of transcription factor activities were calculated as described above. The values of fold-induction by the treatments were calculated by using the basal level activities as a reference. The values of fold-induction (FIG. 16) are presented in a logarithmic scale to distinguish the activation (positive log values) from inhibition (negative log values) relative to the basal activities. The patterns of the alterations in the profiles of transcription factor activities appear highly specific for the agent and for the cell line.

The above examples show that HpaI-tagged library of reporter constructs affords both highly reproducible and quantitative assessments of 15 cancer-related transcription factors. By using this system, these examples demonstrate that cancer cells can be clearly distinguished according to profiles of their transcription factor activities. In addition, having tested certain anti-cancer agents, alterations in the profiles of transcription factor activities were found to be highly specific for the agent and for the cell.

6.7. Example 7

This example demonstrates the preparation of a five-member RTU population able to detect modulation of transcriptional activities by multiple nuclear hormone receptors. Further, this example demonstrates that, despite the high similarity of DNA-binding domains (DBDs) of nuclear hormone receptors, a RTU population as provided in the present application can be used to distinguish transciptional modulation by specific nuclear hormone receptors.

Nuclear hormone receptors (termed nuclear receptors or "NRs" below) constitute a large group of ligand-activated transcription factors that participate in diverse processes such as regulation of development and cellular differentiation, cancer, endocrine functions, metabolism and transport of cholesterol, fatty acids and glucose, and biotransformation of drugs. Nuclear hormone receptors typically have a central, highly conserved DNA-binding domain (DBD) that targets the receptor to specific DNA sequences and a C-terminal portion that includes a ligand-binding domain (LBD), which interacts directly with a hormone or ligand and which further contains a hormone-or ligand-dependent transcriptional activation domain.

6.7.1. Construction of Nuclear Receptor RTUs

In the approach taken for preparing a nuclear receptor RTU population, the LBD of a nuclear receptor is fused in frame with a DBD of Gal4, a yeast transcription factor which possesses well characterized and highly specific DNA binding properties, to obtain a Gal4-DBD-NR-LBD chimera expression construct. Next, the Gal4-DBD-NR-LBD chimera expression construct is co-introduced into cells of interest along with a reporter construct that comprises Gal4 DNA binding elements operationally linked to a reporter gene to obtain a NR RTU. Thus, expression of the reporter sequence from the NR RTU is indicative of the ligand-activated transcriptional activity of the chimeric nuclear receptor. Five different NR RTUs were prepared, including α type estrogen receptor (ERα), vitamin D receptor (VDR), α type thyroid hormone receptor (THRα), glucocorticoid receptor (GR), and constitutive androstane receptor (CAR).

Plasmid cDNA clones encoding for CAR (GENBANK™ Acc. No. BC069626), VDR (GENBANK™ Acc. No. BC060832), GR (GENBANK™ Acc. No. BC015610), and THRα(GENBANK™ Acc. No. BC006560) were obtained from Open Biosystems (Huntsville, AL, USA). cDNA for ERα was amplified by RT-PCR using total RNA isolated from MCF-7 cells. The cDNA was sequence verified to correspond to ERα cDNA (GENBANK™ Acc. No. NM_000125). Gal4 DNA binding domain (Gal4DBD) expression vector, PM DNA-BD, was purchased from BD Biosciences (Palo Alto, CA, USA), and 4×Gal4-luciferase reporter construct was from Promega (Madison, WI, USA).

To produce an in-frame Gal4DBD-GR fusion expression vector, the hormone binding domain of GR (amino-acids 486-777) was amplified by PCR using hGR-Bam (ctc cGG ATC Cag gct gga atg aac ctg gaa (SEQ ID NO:57)) and hGR-Hind (ctc AAG CTT tca ctt ttg atg aaa cag aag (SEQ ID NO:58)) primers and cloned into the multiple cloning site (MCS) of the PM DNA-BD vector in between BamH I and Hind III restriction endonuclease recognition sites.

To produce an in-frame Gal4DBD-ER fusion expression vector, the hormone binding domain of ERα (amino acids 264-595) was amplified by PCR using hERα-Eco (ctc GAA TTC atg ttg aaa cac aag cgc cag (SEQ ID NO:59)) and hERα-Bam (ctc GGA TCC tca gac tgt ggc agg gaa acc (SEQ ID NO:60)) primers and cloned into the MCS of the PM DNA-BD vector in between Eco RI and Bam HI restriction endonuclease recognition sites.

To produce an in-frame Gal4DBD-VDR fusion expression vector, the hormone binding domain of VDR (amino-acids 87-427) was amplified by PCR using hVDR-Eco (ctc GAA TTC atc ggc atg atg aag gag ttc (SEQ ID NO:61)) and hVDR-Hind (ctc AAG CTT tca gga gat ctc att gcc aaa c (SEQ ID NO:62)) primers and cloned into the MCS of the PM DNA-BD vector in between Eco RI and Hind III restriction endonuclease recognition sites.

To produce an in-frame Gal4DBD-THRα fusion expression vector, the hormone binding domain of THRα (amino-acids 119-410) was amplified by PCR using hTHRα-Eco (ctc GAA TTC ggc atg gcc atg gac ttg gtt (SEQ ID NO:63)) and hTHRα-Hind (ctc AAG CTT tta gac ttc ctg atc ctc aaa g (SEQ ID NO:64)) primers and cloned into the MCS of the PM DNA-BD vector in between Eco RI and Hind III restriction endonuclease recognition sites.

To produce an in-frame Gal4DBD-CAR fusion, the hormone binding domain of CAR (amino-acids 103-348) was amplified by PCR using hCAR-Eco (CTC GAA TTC atg agg aaa gac atg ata ctg (SEQ ID NO:65)) and hCAR-Hind (CTC AAG CTT tca gct gca gat ctc ctg gag (SEQ ID NO:66)) primers and cloned into the MCS of the PM DNA-BD vector in between Eco RI and Hind III restriction endonuclease recognition sites.

To produce five distinct 4×Gal4 RTUs, luciferase gene in 4×Gal4-luciferase vector was replaced with five SEAP-derived reporter polynucleotides each carrying single HpaI restriction endonuclease cleavage site in a position that is unique for each reporter polynucleotide.

Each of the Gal4DBD-CAR, Gal4DBD-GR, Gal4DBD-THR, Gal4DBD-VDR, and Gal4DBD-ER fusion expression cassettes was excised from its plasmid backbone and inserted into a backbone of one of the 4×Gal4 RTUs to produce five distinct five distinct NR RTUs. Schematics of the resulting NR RTUs are shown in FIG. 17. Thus, each of the five NR RTUs was made to comprise a vector backbone that included both a NR LBD-Gal4DBD fusion expression cassette and a 4×Gal4 reporter transcription unit. Expression of the NR LBD-Gal4DBD chimeric protein is under control of Simian virus 40 (SV40) promoter. The Hpa I restriction endonuclease cleavage site was located within the reporter polynucleotide sequence at a unique position.

Figure 19B:
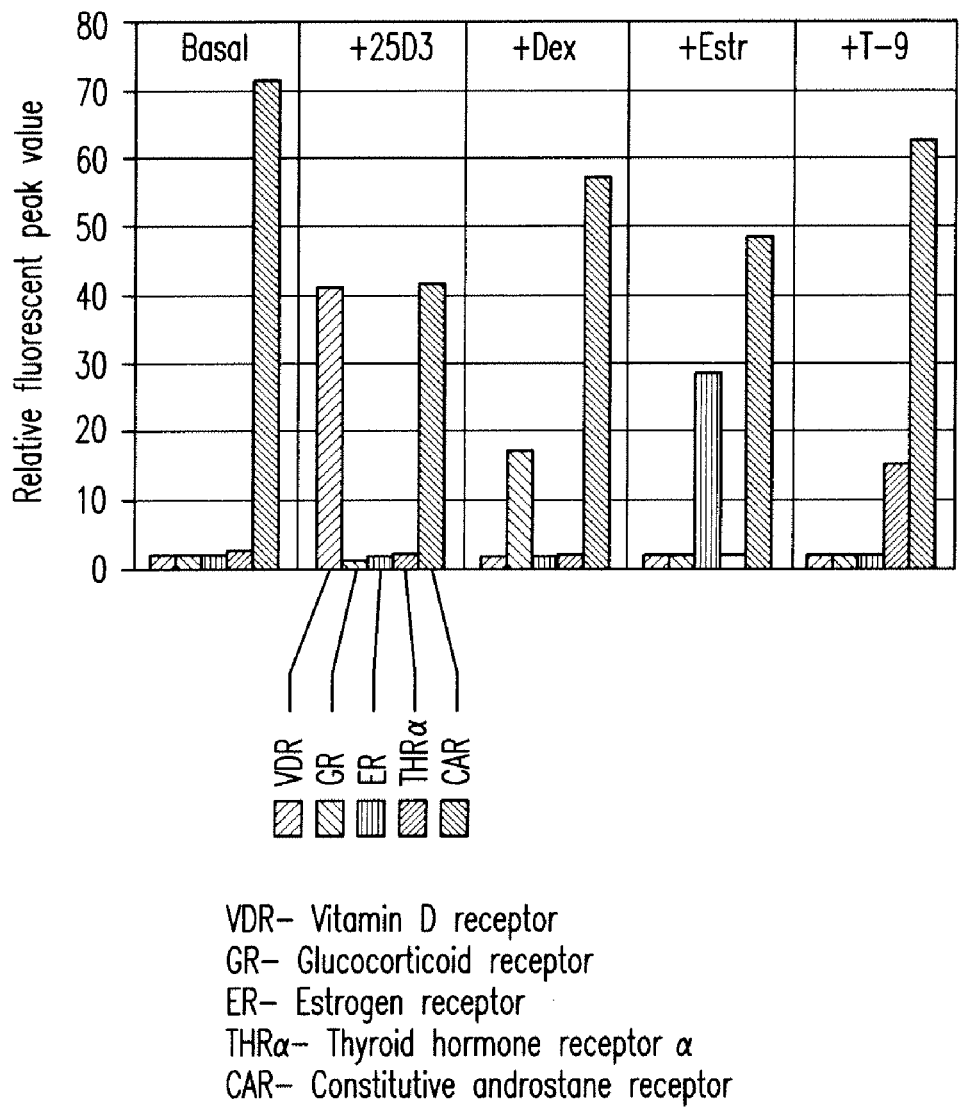

6.7.2. Profiling of Trans-activation Potential of Five Human Nuclear Receptors The outline of the experimental approach is illustrated in FIG. 18. Because all NR RTUs are constructed using identical Gal4 DBDs, all five NR RTUs were individually transfected into HEK293 cells. Twenty-four hrs after transfection the cells were resuspended, combined and re-plated into five individual tissue culture plates. The next day, after mixing and re-plating, the cells were induced by either specific ligand for THRα (3,3',5-Triiodo-L-thyronine T3, 20 ng/ml), specific ligand for VDR (25-dihydroxyvitamin D3, 1 ug/ml), specific ligand for ERα (estradiol, 100 nM ), or by specific ligand for GR (dexamethasone, 10 uM). All inductions were for 6 hrs. Total RNA was isolated from induced and non-induced (control) cells. Reporter transcripts were amplified by RT-PCR, labeled and digested with Hpa I restriction endonuclease as described above. Serial dilutions of each sample were analyzed by capillary electrophoresis. Capillary electrophoregramms are shown on FIG. 19A. Quantification of the reporter peaks shows strong basal transcriptional activity of the CAR RTU relative to other NR RTUs from control cells. Addition of the distinct NR ligands resulted in very specific changes in relative values of the reporter peaks produced by the corresponding NR RTU. Thus, VDR-specific ligand, 25-dihydroxyvitamin D3, increased VDR RTU-specific reporter peak's value (20 fold). Dexamethazone specifically increased reporter peak produced by GR RTU (10 fold). Estradiol and T9 stimulated their corresponding RTUs by, respectively 15 and 10 folds. (FIG. 19B).

6.8. Example 8

This example demonstrates RTUs and methods for profiling activities of mitogen-activated protein kinases.

Mitogen-activated protein kinases (MAPKs) control a plethora of biological processes such as embryogenesis, cell differentiation, cell proliferation, and cell death. MAPKs comprise a growing number of serine/threonine protein kinases that mediate signal transduction in response to variety of extracellular stimuli, such as growth factors, cytokines and DNA damaging agents. The MAPKs are engaged in distributing the signals from upstream components of the signaling network to downstream targets by a common mechanism that involves protein modification cascade (FIG. 20A). MAP kinases require tyrosine and threonine phosphorylation, both catalyzed by MAP kinase kinases, MAPKKs, to exert their biological activity. Five distinct groups of MAPKs have been identified including the extracellular signal-regulated kinases (ERKs 1,2), stress-activated protein kinases p38 (p38 $\alpha$, $\beta$, $\gamma$, $\delta$), c-Jun amino-terminal kinases (JNKs 1,2,3), ERK3, and ERK5.

Transcription based approaches have been developed to assay activity of the kinases, downstream targets of which include known transcription factors. Kinase mediated protein modifications may influence both the ability of the transcription factor to bind DNA, and its ability to recruit co-activators (trans-activation potential). The transcription based kinase assays usually utilize chimeric transcription factors with altered DNA binding specificity. In the most common embodiment of this approach, the chimera comprises in frame fusion of the trans-activation domain (TAD) of the transcription factor with DNA binding domain (DBD) of Gal4 protein, a yeast transcription factor which possesses a well characterized and highly specific DNA binding properties. In a typical experimental design the Gal4-DBD-TAD chimera expression construct is co-introduced into cells of interests along with a reporter construct that comprises Gal4 DNA binding cis-elements operationally linked to a reporter gene (FIG. 20B). Thus, expression level of the reporter gene serves as a measure of the trans-activation potential of the TAD of the chimeric factor and, therefore may be indicative of the status of the kinase pathway that leads to the TAD modification.

To construct individual TAD reporter transcription units (TAD RTUs), plasmid cDNA clones encoding for human c-Jun (GENBANK™ Acc. No. BC006175), ATF2 (GENBANK™ Acc. No. BC026175), and Elk-1(GENBANK™ Acc. No. BC056150) were obtained from Open Biosystems (Huntsville, AL, USA). Gal4 DNA binding domain (Gal4DBD) expression vector, PM DNA-BD, was purchased from BD Biosciences (Palo Alto, CA, USA), and 4×Gal4-luciferase reporter construct is from Promega (Madison, WI, USA).

The trans-activating domains (TAD) of each transcription factor were amplified by PCR and cloned into PM DNA-BD vector to produce functional in frame Gal4DBD-TAD fusion genes operably linked to SV40 promoter.

The TAD of c-Jun (amino-acids 1-246) was amplified by PCR using Jun-Eco (CTCT GAA TTC ATGACTGCAAA-GATGGAAACG (SEQ ID NO:67)) and Jun-Bam (CTCT AAG CTT GTCGATGGGGGACAGGGGCGG (SEQ ID NO:68)) primers, and cloned into the MCS of PM DNA-BD, in between EcoRI and Bam HI restriction endonuclease sites.

The TAD of ATF2 (amino-acids 1-110) was amplified by PCR using ATF2-Bam (CTCT GGATCC Ctgaaattcaagttacatgtgaat (SEQ ID NO:69)) and ATF2-Xba (aagagggataaatctagaggcat (SEQ ID NO:70)) primers, and cloned into the MCS of PM DNA-BD, in between Bam HI and Xba I restriction endonuclease sites.

The TAD of Elk-1 (amino-acids 307-428) was amplified by PCR using Elk1-Eco (tctc GAA TTC ATCTCCCAGCCG-CAGAAGGGC (SEQ ID NO:71)) and Elk1-Hind (tctc AAG CTT TCATGGCTTCTGGGGCCCTGG (SEQ ID NO:72)) primers, and cloned into the MCS of PM DNA-BD, in between Eco RI and Hind III restriction endonuclease sites.

To produce three distinct 4×Gal4 RTUs, luciferase gene in 4×Gal4-luciferase vector was replaced with three SEAP-derived reporter polynucleotides, as described above, each carrying single HpaI restriction endonuclease cleavage site in a position that is unique for each reporter polynucleotide.

To produce three TAD RTUs, each of the Gal4DBD-Jun, Gal4DBD-ATF2, and Gal4DBD-Elk1 fusion expression cassettes was excised from its plasmid backbone along with SV40 promoter and polyadenylation signal, and inserted into backbone of the assigned 4×Gal4 RTU. Schematics of the resulting NR RTUs are shown in FIG. 20B.

6.8.1. Use of HpaI-tagged Reporter RTU Library for Characterization of Kinase Inhibitors Phorbol ester (PMA) initiates signaling cascade that results in preferential activation of ERK1/2 family members of MAP kinases. Elk-1 transcription factor is a specific downstream target of ERKs. Phosphorylation of Ser383 residue in the Elk-1 transcriptional activation domain (TAD) by ERK plays critical role and triggers its active conformation. U0126, a non-competitive inhibitor of MEK1/2 activation, specifically prevents stimulation-dependent activation of ERK1/2 pathway.

The HpaI-tagged reporter RTU library described in the previous subsection was used to assess the status of three major MAPK pathways in parallel. Because all three TAD RTUs above are constructed using identical Gal4 DBDs and identical cis-acting gal4 DNA binding sites, separate transfections were performed in which the TAD RTUs were individually transfected into HEK293 cells. Twenty-four hrs after transfection the cells were combined and re-plated into five individual tissue culture plates. The next day, after re-plating, cells were induced by either PMA alone (10 uM) or by PMA in the presence of the inhibitor U0126 (2.5 uM). The induction was performed for 6 hours. Total RNA was isolated from induced and non-induced (control) cells. Reporter transcripts were amplified by RT-PCR, labeled and digested with Hpa I restriction endonuclease. Serial dilutions of each sample were analyzed by capillary electrophoresis. Quantification of the reporter peaks corresponding to each individual TAD RTU was performed as described in Section 6.1. Results representative of two independent experiments are shown in FIG. 21. Relatively strong basal transcriptional activity of the c-Jun and ATF2 TAD RTUs was observed in control cells. Consistent with published reports, addition of PMA resulted in very strong (~20-fold) activation of the Elk-1 TAD RTU, while the activity of ATF2 and c-Jun TAD RTUs remained unchanged. As expected, the addition of U0126 specifically inhibited PMA-induced, but not basal, activity of the Elk-1 TAD RTU. These results, therefore, demonstrate accuracy, sensitivity and specificity of the methods provided herein.

6.9. Example 9

This example describes the construction of a population of 40 RTUs to profile phenotypes.

6.9.1. RTU Cis-regulatory Elements

The list of targets that can be assessed by 40 RTUs includes the transcription factors that regulate different biological processes, e.g., cell cycle, inflammation, differentiation, and oxidative metabolism. Most of these RTUs are listed in Table 3. Some of transcription factors (e.g., c-myc, E2F, HIF-1a) appear to be dysregulated in many cancer types, while others are involved in a more specific set of cancers. To assess these transcription factors, synthetic promoters can be used wherein a minimal TATA box is fused with multimeric copies of the transcription factor's binding sites. Thus, the transcription of these RTUs can be largely indicative of the activity of a single transcription factor of interest. Several RTUs with naturally occurring promoters of genes whose deregulated transcription was detected in many types of cancer can be constructed. Among those genes are GADD45 and GADD153 that are activated upon DNA damage, and the catalytic subunit of telomerase (hTERT) that is transcriptionally activated in most cancers. As the naturally occurring gene promoters are regulated by multiple transcription factors, the RTUs of this group can be used for assessing not a single transcription factor activity, but, rather, more complex activities of the pathways that regulate gene expression in a specific cancer.

TABLE 3

| Transcription Factors | Response element or consensus | SEQ ID NO | Biological Function | Role in Tumors | Reference |
|---|---|---|---|---|---|
| Ap1 (c-jun/c-fos) | TGACTAA | 73 | JNK pathway: Proliferatiaon, Differentiation, Stress responses | Deregulated in most tumors | Woodgett (1990) Semin Cancer Biol. 1(6): 389-97 |
| CSL | CTCCCCAA | 74 | Notch pathway: Differentiation, Homeostatis | Up regulated T-cell leukemia | Radtke and Raj (2003) Nat Rev Cancer 3(10): 756-67 |
| Gli1, Gli2 | GACCACCCA | 75 | Sonic hedgehog pathway: Differentiation | Basal cell carcinomas, medulloblastomas | Yoon et al. (2002) J Biol Chem. 277(7): 5548-55; Ikram et al. (2004) J Invest Dermatol. 122(6): 1503-9 |
| Runx family: | AACCACA/PuACCPuCA | 76 | | | |
| Runx1 | AACCACA/PuACCPuCA | | Hematopoiesis | Leukemias | Coffman (2003) Cell Biol Int. 27(4): 315-24; Otto et al. (2003) J Cell Biochem. 89(1): 9-18 |
| Runx2 | AACCACA/PuACCPuCA | | Osteogenesis | Cleidocronial displasia | Coffman (2003) Cell Biol Int. 27(4): 315-24; Otto et al. (2003) J Cell Biochem. 89(1): 9-18 |
| Runx3 | AACCACA/PuACCPuCA | | Neurogenesis | Gastric cancer | Coffman (2003) Cell Biol Int. 27(4): 315-24; Otto et al. (2003) J Cell Biochem. 89(1): 9-18 |
| Ap-2 | GCCNNNGGC | 77 | Embryonic morphogenesis and adult differentiation | Melanomas | Huang et al. (1998) EMBO J. 17(15): 4358-69 |
| SNAIL | CACCTG | 78 | EMT during mesoderm formulation | Epithelial tumors | Battle et al. (2003) |
| Ets family | GGAA/T | 79 | MAP kinases mediated signaling: Differentiation | Control mestastatic potential of many epithelial tumors | Hsu et al. (2004) J Cell Biochem. 91(5): 896-903 |

TABLE 3-continued

| Transcription Factors | Response element or consensus | SEQ ID NO | Biological Function | Role in Tumors | Reference |
|---|---|---|---|---|---|
| FoxO family | A/GTAAAT/CA | 80 | Development, metabolic pathways | Translocates in ALL and rabdomyosarcomas | Brunet et al. (1999) Cell 96(6): 857-68; Accili and Arden (2004) Cell 117(4): 421-6 |
| C/EBPbeta | A/GTTGCGC/TAAC/T | 81 | Differentiation, Immune responses | Mutates in AML | Grimm and Rosen (2003) J Mammary Gland Biol Neoplasia 8(2): 191-20 |
| Stat3 | GCTTCCCGAACGTT | 82 | Jak/STAT pathway: Differentiation, Inflammation, Apoptosis | Constitutively activated by oncogenes and tumor viruses | Turkson and Jove (2000) Oncogene 19(56): 6613-26 |
| SRF | GATGTCCatattaGGACATC | 83 | Controls transcription of immediate growth responses genes | Cooperates with Ets transcription factors | Murai and Treisman (2002) Mol Cell Biol. 22(20): 7083-92 |
| E2F | TTTCCCGC | 84 | Cell cycle progression | Deregulated in most human cancers | Bell and Ryan (2004) Cell Death Differ. 11(2): 137-42 |
| c-Myc | CACGTG | 85 | Cell growth, proliferation and survival | Overexpressed in many tumors | Secombe et al. (2004) Cell 117(2): 153-6 |
| HIFalpha | GCCCTACGTGCTGTCTCA | 86 | Oxygene homeostatis | Induced in tumors by local hypoxia | Semenza (2003) Nat Rev Cancer 3(10): 721-32 |
| Egr-1 | CGCCCSCGC | 87 | Cell growth, differentiation and survival | Promotes growth of many tumors | Baron et al. (2003) Oncogene 22(27): 4194-204 |
| NRF2 | GCTCTTCCGGT | 88 | Antioxidative responses | Induced in tumors by chemopreventive agents | Kwak et al. (2002) Mol Cell Biol. 22(9): 2883-92 |
| MyoD | CAGCTC | 89 | Skeletal muscle development | Marker in rabdomyosarcomas | Sebire and Malone (2003) J Clin Pathol. 56(6): 412-6 |
| Sox9 | TTCAAAGGCGCCTGTTT | 90 | Chondrogenesis | Marker in chondrosarcomas | Wehrli et al. (2003) Hum Pathol. 34(3): 263-9. |
| WT1 | GCGGGGGCG or TCCTCCTCCTCCTCTCC | 91, 92 | Renal development and sex determination | Mutated in Wilms tumors, overexpressed in many other tumors | Loeb and Sukumar (2002) Int J Hematol. 76(2): 117-26 |
| PAX family | CGTCACGG/CTTG/CA/G | 93 | Development, stem cell pluropotency | Deregulated and translocated in many types of cancer | Chi and Epstein (2002) Trends Genet. 18(1): 41-7 |
| Promoters | | | | | |
| hTERT promoter | hTERT promoter | | Telomere maintenance | Overexpressed in most tumors | Gu and Fang (2003) Cancer Biol Ther. 2(4 Suppl 1): S64-70 |
| Gadd45 promoter | Gadd45 promoter | | DNA damage response | Induced by chemotherapy | Johnson et al. (2002) Mol Cancer Ther. 1(14): 1293-304 |
| Gadd153 promoter | Gadd153 promoter | | DNA damage response | Induced by chemotherapy | Johnson et al. (2002) Mol Cancer Ther. 1(14): 1293-304 |

6.9.2. RTU Reporter Sequences

As demonstrated in Section 6.3 above, in most cases, the introduction of a processing tag (e.g., HpaI site) at a variable position within the reporter sequence has no significant affect on the reporter sequences transcription efficacy. Indeed, >85% of reporters produced by this design have comparable efficacies of transcription, with the standard deviation<20%. Therefore, constructing appropriate reporter sequences for the additional RTUs should not be an issue. There should also be no problem with including the additional RTUs into the multiplex system. The maximal number of RTUs that this system can accommodate is determined by the resolution of the detection. In this system, for example, the HpI-digested fragments are separated by using capillary gel electrophoresis of the ABI sequencer. According to the manufacturer, use of the ABI sequencer allows quantitative assessment of peaks of DNA fragments in the range of 100 to 600 bp with the resolution of 1 bp. In other words, the system can accommodate up to 500 RTUs that differ by 1 bp. In the RTU population that can be generated, the processed products can differ by 5 bps, thus 100 of those reporters can be accommodated.

6.9.3. Assembling and Testing the Population of 40 RTUs

The constructed RTUs can be verified by sequencing. An initial functional testing of the individual RTUs can be performed in a transient transfection assay, by stimulating cells with an appropriate inducer or by co-transfecting expression vectors with dominant-negative inhibitors or dominant-positive activators of the transcription factor or promoter of interest, as was done in Examples 6-8 above. The RTUs can be assessed by RT-PCR of the reporter sequence mRNA.

The population of 40 RTUs can be prepared as an equimolar mix of RTUs and transiently transfected into a target cell line (e.g., 293 cells), and batches of transfected cells can be stimulated in parallel with known inducers of individual RTUs. The reporter RNA can be amplified by RT-PCR, digested with HpaI, and resolved, as described in the working examples above. The linearity of amplification can be assessed, as in the working examples above, by assessing the peak values of several calibrating SV40 or CMV RTUs added to the system at various molar ratios. When PCR amplification is within a linear range, the ratios of the peaks of the calibrating RTUs correspond to the ratios of the concentrations of these constructs within the system. A skewed peaks ratio indicates an over-amplification.

6.10. Example 10

This example describes applications of the RTU population for cancer research and drug discovery.

6.10.1. Identification of a disease state

This example describes how generating a transcription factor profile database in human cancer lines of the NC160 collection and in the normal counterparts can be used to identify a disease state in a cell with an unknown disease state, such as cell from a biopsy of a patient.

Table 4 lists the normal primary epithelial cells and matching cancer cell lines of the same origin that can be used. These cells were selected based on: (1) the availability of the primary epithelial cells; (2) the availability of a matching set of extensively characterized cancer cell lines of the same tissue origins from the NCI60 collection; (3) the availability of large arrays of data on these cells, including the databases of cell viability upon treatment with tens of thousands compounds and the databases of the drug-inducible gene expression profiles.

Reference profiles in the normal epithelial cells are generated using a RTU population as described herein. The activity profiles of the RTUs are obtained by following the protocols described in the working examples above. For example, the different primary cells are transfected in parallel batches with the reporter system containing an equimolar mix of 30 RTUs and a series of calibrating SV40 RTUs and CMV RTUs taken at different concentrations. One day later, reporter RNA are amplified, processed by HpaI digestion, and resolved on the capillary gel electrophoresis. The relative values of transcriptional activities of individual RTUs can be calculated by using the values of the corresponding peaks of the electrophoregram. To account for a possible non-linearity of PCR amplification, the peak values can be calculated by using a calibration curve derived from the peak values of series of calibrating SV40 RTUs, similar to that described in the working examples.

As demonstrated in the working examples, the profile of transcription factor activities is highly reproducible in established cancer cell lines. To determine if this is the case with primary cells, several assessments for each cell type at different passages can establish the conditions when the cells show a reproducible pattern of transcription factor activities.

Having obtained the normalized relative values of RTUs, the profiles of transcription factor activities in the primary cells of different origin can be generated. To account for variations in the efficacy of transfection and detection in different cells, the normalization on an average level of transcription factor activities in the transfection can be used, that is, the internal normalization. This normalization procedure utilized in the working examples was demonstrated to provide an accurate assessment of transcription factor activity profiles in different cell lines. The internal normalization was adapted from the cDNA array hybridization technique. By analogy with cDNA array hybridization, the more individual RTUs there are within the reporter system, the better the internal normalization should work.

In addition to the generated profiles of transcription factor activities in normal cells, the transcription factor profiles in cancer cell lines of the same origin, such as those provided in Table 4 in this example, can be assessed.

Having generated the profiles of both normal (or non-diseased) cells as well as cancerous cell lines, these profiles are used to compare to profiles generated from cells of unknown disease state, for example, from a biopsy. Where matching profiles are observed, an identification of the state, non-diseased or diseased, is made for the cell of unknown disease state.

TABLE 4

| Normal Human Cell Types (Cat#) | Vendor | NCI60 cell lines |
| --- | --- | --- |
|  |  | Astrocytomas/ Gliablastomas |
| Astrocytes (CC-2565) | Clonetics | SF-268 |
|  |  | SF-295 |
|  |  | SF-539 |
|  |  | SNB-19 |
|  |  | SNB75 |
|  |  | SNB-78 |
|  |  | U251 |

TABLE 4-continued

| Normal Human Cell Types (Cat#) | Vendor | NCI60 cell lines |
|---|---|---|
| | | Renal Carcinomas |
| Renal epithelial (CC-2556) | Clonetics | A498 |
| Renal cortical epithelial (CC-2554) | Clonetics | CAKI-1 |
| | | ACHN |
| | | 786-0 |
| | | UO-31 |
| | | SN12C |
| | | SN12K1 |
| | | Breast Carcinomas |
| Mammary epithelial (CC-2551) | Clonetics | MCF7 |
| | | NCI/ADR-RES |
| | | MDA-MB-231 |
| | | MDA-MB-435 |
| | | BT-549 |
| | | HS 578T |
| | | MDA-MB-468 |
| | | Melanomas |
| Melanocytes (C-124XX) | PromoCell | Lox IMVI |
| | | MALME-3M |
| | | M14 |
| | | SK-MEL-2 |
| | | SK-MEL-5 |
| | | SK-MEL-28 |
| | | UACC-257 |
| | | UACC-62 |
| | | RPMI-7951 |
| | | M19-MEL |
| | | Prostate Carcinomas |
| Prostate epithelial (CC-2555) | Clonetics | PC-3 |
| | | DU-145 |

6.10.2. Drug Screening

This example describes how profiles of RTU activity generated in cells treated with anti-cancer agents can used to identify potential novel drug therapies. In particular, a set of standard anti-cancer agents from the NCI's Developmental Therapeutic Program (DTP) can be assessed in the NCI60 cell lines to generate a database of the activity profiles elicited by the drugs.

A list of extensively characterized standard anti-cancer drugs can be found via the web site of the National Cancer Institute of the U.S. National Institutes of Health (see www.dtp.nci.nih.gov/docs/cancer/cancer_data.html). For each cell line to be tested, 15 to 25 drugs that kill the particular cell line, and an equal number of reference drugs that do not affect the cell viability can be selected (the data on the sensitivity of particular cells to the drugs is also available at the aforementioned web site).

To perform a drug assessment, a target cell line is transiently transfected with an RTU population as described herein. Cells are aliquoted into wells of a 96-well plate. Although 6-well plates were used in the working examples, due to the high sensitivity of PCR-based detection, only about a $\frac{1}{20}$ of the isolated RNA was used. Therefore, one well of a 96-well plate should provide sufficient amount of RNA for the analysis. One day after transfection, tested drugs are added to cells at the concentrations and for the period of time that have been used in previously published studies on cDNA array gene expression profiling (e.g., Scherf et al. (2000) *Nat Genet.* 24(3):236-44). A single 96-well plate should be able to accommodate an assay of 30 to 50 drugs for one cell line performed in duplicate.

At the end of incubation, cells are lysed, and total RNA isolated, amplified, processed, and detected, as described above in the working examples. Relative activities of individual RTUs can be calculated and normalized, and fold-induction (or fold-inhibition) will be assessed according to protocols of previously discussed. Although the use of a RTU population, as described herein, has a large dynamic range, some situations may arise when the peak values of some RTUs will be much higher or lower than the average. This situation is not desirable, because it increases the error. To equalize the heights of the peaks, the concentration of the particular RTU plasmid within the system can be correspondingly adjusted.

By analyzing the activities of many transcription factors in cancer and normal cells, previously unavailable data about the activities of numerous transcription factors and pathways in cancer biology can be obtained. By examining the alterations in the signal transduction in response to drugs, a database of transcription factor activities comprising the molecular profiles of drugs in several different cancer cell lines can be generated. Activity profiles generated in cells treated to potential new drug can used to identify those that are likely to have a benefit against a cancer where the profile of the potential new drug matches those generated by known anti-cancer drugs.

Although the foregoing invention has been described in some detail by way of illustration and example for purposes of clarity of understanding, it will be apparent to those skilled in the art that certain changes and modifications of the invention may be practiced that are intended to fall within the scope of the appended claims.

All publications and patent applications mentioned in this application, including any and all nucleic acid sequences referred to by accession number or otherwise, are herein incorporated by reference in their entireties for any and all purposes.

What is claimed:

1. A reporter transcription unit (RTU) population comprising polynucleotide RTUs, each RTU comprising
   a reporter sequence;
   a processing tag located in the reporter sequence; and
   a cis-regulatory element operably linked to the reporter sequence, wherein transcription of the reporter sequence is modulated by the cis-regulatory element; and
   wherein the reporter sequences of any two RTUs in the population, outside of the processing tags, are identical or substantially identical, wherein the processing tags are identical between any two RTUs in the population, and wherein the reporter sequences of any two RTUs operably linked to non-identical cis-regulatory elements are distinguishable by the locations of the processing tags in the reporter sequences.

2. The RTU population of claim 1, wherein a trans-acting factor binds to at least one cis-regulatory element.

3. The RTU population of claim 1, wherein the reporter sequences between any two RTUs in the population, outside of the processing tags, are substantially identical.

4. The RTU population of claim 3, wherein the substantially identical reporter sequences differ by less than 10 nucleotides.

5. The RTU population of claim 3, wherein the substantially identical reporter sequences differ by 1 nucleotide.

6. The RTU population of claim 1, wherein the reporter sequences, outside of the processing tags, are identical between any two RTUs in the population.

7. The RTU population of claim 1, wherein the reporter sequences, including the processing tags, between any two RTUs in the population comprise an identical number of nucleotides.

8. The RTU population of claim 7, wherein the positions of the processing tags in the reporter sequences differ by at least 1 to 15 nucleotides between any two RTUs in the population.

9. The RTU population of claim 8, wherein the reporter sequences, outside of the processing tags, are identical between any two RTUs in the population.

10. The RTU population of claim 1, wherein the processing tag for each RTU in the population is selected from the group consisting of:
    a) a thymine, adenine, cytosine, or guanine nucleotide residue;
    b) an endonuclease recognition site;
    c) a primer sequence;
    d) a polyadenylation termination signal; and
    e) a mutation in the reporter sequence comprising a deletion, insertion, or substitution.

11. The RTU population of claim 10, wherein the processing tag is selected from the group consisting of: a thymine, adenine, cytosine, or guanine nucleotide residue; and an endonuclease recognition site.

12. The RTU population of claim 1, wherein at least one of the RTUs in the population comprises a cis-regulatory element selected from the group consisting of a promoter, an enhancer, an RNA stability signal, and a polyadenylation signal or a combination thereof.

13. The RTU population of claim 1, wherein, for each RTU in the population, the cis-regulatory element comprises a promoter or an enhancer, and has at least one binding site for a DNA-binding protein.

14. The RTU population of claim 13, wherein the binding site is a transcription factor binding site.

15. The RTU population of claim 13, wherein the cis-regulatory element modulates the stability or maturation of the reporter species.

16. The RTU population of claim 1, wherein each RTU in the population further comprises a 5' and a 3' primer sequence that flank the reporter sequence.

17. The RTU population of claim 1, wherein at least one of the RTUs in the population comprises an intron.

18. A reporter transcription unit (RTU) population comprising polynucleotide RTUs, each RTU comprising
    a reporter sequence;
    a processing tag located in the reporter sequence; and
    a cis-regulatory element operably linked to the reporter sequence, wherein transcription of the reporter sequence is modulated by binding of a trans-acting factor to the cis-regulatory element; and
    wherein the reporter sequences of any two RTUs in the population, outside of the processing tags, are identical or substantially identical, wherein the processing tags are identical between any two RTUs in the population, and wherein the reporter sequences of any two RTUs operably linked to cis-regulatory elements modulated by non-identical trans-acting factors are distinguishable by the locations of the processing tags in the reporter sequences.

19. A population of vectors comprising the RTU population of claim 1.

20. The population of vectors of claim 19, wherein each vector is selected from the group consisting of a plasmid, a phagemid, a retroviral vector, a lentiviral vector, an adenoviral vector, and an adeno-associated vector.

21. A cell comprising the RTU population of claim 1.

22. The cell of claim 21, wherein the RTU population is stably incorporated into the genome of said cell.

23. The cell of claim 21, wherein the cell is selected from the group consisting of a plant, a bacterium, a fungus, and a vertebrate.

24. The cell of claim 21, wherein the cell is an embryonic stem cell.

25. A tissue comprising the cell of claim 21.

26. The tissue of claim 25, wherein said tissue comprises a biopsy sample, an autopsy sample, or a slice tissue culture.

27. A population of cells comprising the RTU population of claim 1, wherein each cell of the cell population comprises at least one RTU member of the RTU population.

28. A population of cells comprising the RTU population of claim 1, wherein each cell of the cell population comprises each member of the RTU population.

29. A non-human organism comprising the cell of claim 21.

30. A kit comprising the RTU population of claim 1.

31. A kit comprising a cell, wherein the cell comprises the RTU population of claim 1.

32. A kit comprising a vector population, wherein the vector population comprises the RTU population of claim 1.

33. A tissue comprising the population of cells of claim 27.

34. A tissue comprising the population of cells of claim 28.

35. A non-human organism comprising the population of cells of claim 27.

36. A non-human organism comprising the population of cells of claim 28.

* * * * *

SEQUENCE LISTING

```
<160> NUMBER OF SEQ ID NOS: 93

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
```
tgcagattgc gcaatctgca                                           20

<210> SEQ ID NO 2
<211> LENGTH: 27
<212> TYPE: DNA
<213> ORGANISM: Artificial Sequence
<220> FEATURE:
<223> OTHER INFORMATION: Oligonucleotide

<400> SEQUENCE: 2
agagattgcc tgacgtcaga gagctag                                   27

<210> SEQ ID NO 3
<211> LENGTH: 25
<212> TYPE: DNA
<213> ORGANISM: Artificial Sequence
<220> FEATURE:
<223> OTHER INFORMATION: Oligonucleotide

<400> SEQUENCE: 3
atttaagttt cgcgcccttt ctcaa                                     25

<210> SEQ ID NO 4
<211> LENGTH: 25
<212> TYPE: DNA
<213> ORGANISM: Artificial Sequence
<220> FEATURE:
<223> OTHER INFORMATION: Oligonucleotide

<400> SEQUENCE: 4
tacaggcata acggttccgt agtga                                     25

<210> SEQ ID NO 5
<211> LENGTH: 9
<212> TYPE: DNA
<213> ORGANISM: Artificial Sequence
<220> FEATURE:
<223> OTHER INFORMATION: Oligonucleotide

<400> SEQUENCE: 5 gcggggcg                                                         9

<210> SEQ ID NO 6
<211> LENGTH: 21
<212> TYPE: DNA
<213> ORGANISM: Artificial Sequence
<220> FEATURE:
<223> OTHER INFORMATION: Oligonucleotide

<400> SEQUENCE: 6
cgcttgatga ctcagccgga a                                         21

<210> SEQ ID NO 7
<211> LENGTH: 26
<212> TYPE: DNA
<213> ORGANISM: Artificial Sequence
<220> FEATURE:
<223> OTHER INFORMATION: Oligonucleotide

<400> SEQUENCE: 7
gatcgaactg accgcccgcg gcccgt                                    26

<210> SEQ ID NO 8
<211> LENGTH: 10
<212> TYPE: DNA

```
<213> ORGANISM: Artificial Sequence
<220> FEATURE:
<223> OTHER INFORMATION: Oligonucleotide

<400> SEQUENCE: 8 rctcattaay                                                              10

<210> SEQ ID NO 9
<211> LENGTH: 34
<212> TYPE: DNA
<213> ORGANISM: Artificial Sequence
<220> FEATURE:
<223> OTHER INFORMATION: Oligonucleotide

<400> SEQUENCE: 9
gtccaaagtc aggtcacagt gacctgatca agtt                                   34

<210> SEQ ID NO 10
<211> LENGTH: 21
<212> TYPE: DNA
<213> ORGANISM: Artificial Sequence
<220> FEATURE:
<223> OTHER INFORMATION: Oligonucleotide

<400> SEQUENCE: 10
gatctcgagc aggaagttcg a                                                 21

<210> SEQ ID NO 11
<211> LENGTH: 24
<212> TYPE: DNA
<213> ORGANISM: Artificial Sequence
<220> FEATURE:
<223> OTHER INFORMATION: Oligonucleotide

<400> SEQUENCE: 11
aaatacgaga tccaccgaga ctcc                                              24

<210> SEQ ID NO 12
<211> LENGTH: 22
<212> TYPE: DNA
<213> ORGANISM: Artificial Sequence
<220> FEATURE:
<223> OTHER INFORMATION: Oligonucleotide

<400> SEQUENCE: 12
gcaggaacag cgccgataca at                                                22

<210> SEQ ID NO 13
<211> LENGTH: 679
<212> TYPE: DNA
<213> ORGANISM: Artificial Sequence
<220> FEATURE:
<223> OTHER INFORMATION: Oligonucleotide

<400> SEQUENCE: 13
aaatacgaga tccaccgaga ctccacactg gacccctccc tgatggagat gacagaggct       60
gccctgcgcc tgctgagcag gaaccccgc ggcttcttcc tcttcgtgga gggtggtcgc       120
atcgaccatg gtcatcatga aagcagggct taccgggcac tgactgagac gatcatgttc      180
gacgacgcca ttgagagggc gggccagctc accagcgagg aggacacgct gagcctcgtc      240
actgccgacc actcccacgt cttctccttc ggaggctacc ccctgcgagg gagctccatc      300
ttcgggctgg cccctggcaa ggcccgggac aggaaggcct acacggtcct cctatacgga      360
aacggtccag gctatgtgct caaggacggc gcccggccgg atgttaccga gagcgagagc      420
```

```
gggagcccng agtatcggca gcagtcagca gtgccctgg acgaagagac ccacgcaggc    480
gaggacgtgg cggtgttcgc gcgcggcccg caggcgcacc tggttcacgg cgtgcaggag    540
cagaccttca tagcgcacgt catggccttc gccgcctgcc tggagcccta caccgcctgc    600
gacctggcgc cccccgccgg caccaccgac gccgcgcacc cgggttactc tagatagatt    660
gtatcggcgc tgttcctgc                                                 679

<210> SEQ ID NO 14
<211> LENGTH: 684
<212> TYPE: DNA
<213> ORGANISM: Artificial Sequence
<220> FEATURE:
<223> OTHER INFORMATION: Oligonucleotide

<400> SEQUENCE: 14
aaatacgaga tccaccgaga ctccacactg gaccctccc tgatggagat gacagaggct     60
gccctgcgcc tgctgagcag gaaccccgc ggcttcttcc tcttcgtgga gggtggtcgc    120
atcgaccatg gtcatcatga aagcagggct taccgggcac tgactgagac gatcatgttc    180
gacgacgcca ttgagagggc gggccagctc accagcgagg aggacacgct gagcctcgtc    240
actgccgacc actcccacgt cttctccttc ggaggctacc ccctgcgagg gagctccatc    300
ttcgggctgg cccctggcaa ggcccgggac aggaaggcct acacggtcct cctatacgga    360
aacggtccag gctatgtgct caaggacggc gcccggccgg atgttaccga gagcgagagc    420
gggagccccg agtatcggca gcagtcagca gtgccctgg acgaagagac ccacgcaggc    480
gaggacgtgg cggtgttcgc gcgcggcccg caggcgcacc tggttcacgg cgtgcaggag    540
cagaccttca tagcgcacgt catggccttc gccgcctgcc tgttaacgag ccctacaccg    600
cctgcgacct ggcgcccccc gccggcacca cgacgccgc gcacccgggt tactctagat    660
agattgtatc ggcgctgttc ctgc                                           684

<210> SEQ ID NO 15
<211> LENGTH: 683
<212> TYPE: DNA
<213> ORGANISM: Artificial Sequence
<220> FEATURE:
<223> OTHER INFORMATION: Oligonucleotide

<400> SEQUENCE: 15
aaatacgaga tccaccgaga ctccacactg gaccctccc tgatggagat gacagaggct     60
gccctgcgcc tgctgagcag gaaccccgc ggcttcttcc tcttcgtgga gggtggtcgc    120
atcgaccatg gtcatcatga aagcagggct taccgggcac tgactgagac gatcatgttc    180
gacgacgcca ttgagagggc gggccagctc accagcgagg aggacacgct gagcctcgtc    240
actgccgacc actcccacgt cttctccttc ggaggctacc ccctgcgagg gagctccatc    300
ttcgggctgg cccctggcaa ggcccgggac aggaaggcct acacggtcct cctatacgga    360
aacggtccag gctatgtgct caaggacggc gcccggccgg atgttaccga gagcgagagc    420
gggagccccg agtatcggca gcagtcagca gtgccctgg acgaagagac ccacgcaggc    480
gaggacgtgg cggtgttcgc gcgcggcccg caggcgcacc tggttcacgg cgtgcaggag    540
cagaccttca tagcgcacgt catggccttc gttaaccgcc tgcctggagc cctacaccgc    600
ctgcgacctg gcgcccccg ccggcaccac cgacgccgcg cacccgggtt actctagata    660
gattgtatcg gcgctgttcc tgc                                            683
```

<210> SEQ ID NO 16
<211> LENGTH: 679
<212> TYPE: DNA
<213> ORGANISM: Artificial Sequence
<220> FEATURE:
<223> OTHER INFORMATION: Oligonucleotide

<400> SEQUENCE: 16

```
aaatacgaga tccaccgaga ctccacactg gacccctccc tgatggagat gacagaggct      60
gccctgcgcc tgctgagcag gaaccccgc ggcttcttcc tcttcgtgga gggtggtcgc     120
atcgaccatg gtcatcatga aagcagggct taccgggcac tgactgagac gatcatgttc     180
gacgacgcca ttgagagggc gggccagctc accagcgagg aggacacgct gagcctcgtc     240
actgccgacc actcccacgt cttctccttc ggaggctacc ccctgcgagg gagctccatc     300
ttcgggctgg cccctggcaa ggcccgggac aggaaggcct acacggtcct cctatacgga     360
aacggtccag gctatgtgct caaggacggc gcccggccgg atgttaccga gagcgagagc     420
gggagccccg agtatcggca gcagtcagca gtgcccctgg acgaagagac ccacgcaggc     480
gaggacgtgg cggtgttcgc gcgcggcccg caggcgcacc tggttcacgg cgtgcaggag     540
cagaccttca tagcgcacgt taacgccttc gccgcctgcc tggagcccta caccgcctgc     600
gacctggcgc ccccgccgg caccaccgac gccgcgcacc cgggttactc tagatagatt     660
gtatcggcgc tgttcctgc                                                  679
```

<210> SEQ ID NO 17
<211> LENGTH: 683
<212> TYPE: DNA
<213> ORGANISM: Artificial Sequence
<220> FEATURE:
<223> OTHER INFORMATION: Oligonucleotide

<400> SEQUENCE: 17

```
aaatacgaga tccaccgaga ctccacactg gacccctccc tgatggagat gacagaggct      60
gccctgcgcc tgctgagcag gaaccccgc ggcttcttcc tcttcgtgga gggtggtcgc     120
atcgaccatg gtcatcatga aagcagggct taccgggcac tgactgagac gatcatgttc     180
gacgacgcca ttgagagggc gggccagctc accagcgagg aggacacgct gagcctcgtc     240
actgccgacc actcccacgt cttctccttc ggaggctacc ccctgcgagg gagctccatc     300
ttcgggctgg cccctggcaa ggcccgggac aggaaggcct acacggtcct cctatacgga     360
aacggtccag gctatgtgct caaggacggc gcccggccgg atgttaccga gagcgagagc     420
gggagccccg agtatcggca gcagtcagca gtgcccctgg acgaagagac ccacgcaggc     480
gaggacgtgg cggtgttcgc gcgcggcccg caggcgcacc tggttcacgg cgtgcaggag     540
cagaccttca tagcgttaac acgtcatggc cttcgccgcc tgcctggagc cctacaccgc     600
ctgcgacctg gcgccccccg ccggcaccac cgacgccgcg cacccgggtt actctagata     660
gattgtatcg gcgctgttcc tgc                                             683
```

<210> SEQ ID NO 18
<211> LENGTH: 682
<212> TYPE: DNA
<213> ORGANISM: Artificial Sequence
<220> FEATURE:
<223> OTHER INFORMATION: Oligonucleotide

<400> SEQUENCE: 18

```
aaatacgaga tccaccgaga ctccacactg gacccctccc tgatggagat gacagaggct      60
```

```
gccctgcgcc tgctgagcag gaaccccgc ggcttcttcc tcttcgtgga gggtggtcgc      120
atcgaccatg gtcatcatga aagcagggct taccgggcac tgactgagac gatcatgttc     180
gacgacgcca ttgagagggc gggccagctc accagcgagg aggacacgct gagcctcgtc     240
actgccgacc actcccacgt cttctccttc ggaggctacc ccctgcgagg gagctccatc     300
ttcgggctgg cccctggcaa ggcccgggac aggaaggcct acacggtcct cctatacgga     360
aacggtccag gctatgtgct caaggacggc gcccggccgg atgttaccga gagcgagagc     420
gggagccccg agtatcggca gcagtcagca gtgcccctgg acgaagagac ccacgcaggc     480
gaggacgtgg cggtgttcgc gcgcggcccg caggcgcacc tggttcacgg cgtgcaggag     540
cagaccgtta acatagcgca cgtcatggcc ttcgccgcct gcctgagcc ctacaccgcc      600 tgcgacctgg cgcccccgc cggcaccacc gacgccgcgc acccgggtta ctctagatag      660
attgtatcgg cgctgttcct gc                                              682
```

```
<210> SEQ ID NO 19
<211> LENGTH: 684
<212> TYPE: DNA
<213> ORGANISM: Artificial Sequence
<220> FEATURE:
<223> OTHER INFORMATION: Oligonucleotide

<400> SEQUENCE: 19
aaatacgaga tccaccgaga ctccacactg gaccccctccc tgatggagat gacagaggct    60
gccctgcgcc tgctgagcag gaaccccgc ggcttcttcc tcttcgtgga gggtggtcgc     120
atcgaccatg gtcatcatga aagcagggct taccgggcac tgactgagac gatcatgttc    180
gacgacgcca ttgagagggc gggccagctc accagcgagg aggacacgct gagcctcgtc    240
actgccgacc actcccacgt cttctccttc ggaggctacc ccctgcgagg gagctccatc    300
ttcgggctgg cccctggcaa ggcccgggac aggaaggcct acacggtcct cctatacgga    360
aacggtccag gctatgtgct caaggacggc gcccggccgg atgttaccga gagcgagagc    420
gggagccccg agtatcggca gcagtcagca gtgcccctgg acgaagagac ccacgcaggc    480
gaggacgtgg cggtgttcgc gcgcggcccg caggcgcacc tggttcacgg cgtgcagtta    540
acgagcagac cttcatagcg cacgtcatgg ccttcgccgc ctgcctggag ccctacaccg    600
cctgcgacct ggcgcccccc gccggcacca ccgacgccgc gcacccgggt tactctagat    660
agattgtatc ggcgctgttc ctgc                                           684
```

```
<210> SEQ ID NO 20
<211> LENGTH: 679
<212> TYPE: DNA
<213> ORGANISM: Artificial Sequence
<220> FEATURE:
<223> OTHER INFORMATION: Oligonucleotide

<400> SEQUENCE: 20
aaatacgaga tccaccgaga ctccacactg gaccccctccc tgatggagat gacagaggct    60
gccctgcgcc tgctgagcag gaaccccgc ggcttcttcc tcttcgtgga gggtggtcgc     120
atcgaccatg gtcatcatga aagcagggct taccgggcac tgactgagac gatcatgttc    180
gacgacgcca ttgagagggc gggccagctc accagcgagg aggacacgct gagcctcgtc    240
actgccgacc actcccacgt cttctccttc ggaggctacc ccctgcgagg gagctccatc    300
ttcgggctgg cccctggcaa ggcccgggac aggaaggcct acacggtcct cctatacgga    360
```

```
aacggtccag gctatgtgct caaggacggc gcccggccgg atgttaccga gagcgagagc    420
gggagccccg agtatcggca gcagtcagca gtgcccctgg acgaagagac ccacgcaggc    480
gaggacgtgg cggtgttcgc gcgcggcccg caggcgcacc tggttaacgg cgtgcaggag    540
cagaccttca tagcgcacgt catggccttc gccgcctgcc tggagcccta caccgcctgc    600
gacctggcgc cccccgccgg caccaccgac gccgcgcacc cgggttactc tagatagatt    660
gtatcggcgc tgttcctgc                                                 679

<210> SEQ ID NO 21
<211> LENGTH: 681
<212> TYPE: DNA
<213> ORGANISM: Artificial Sequence
<220> FEATURE:
<223> OTHER INFORMATION: Oligonucleotide

<400> SEQUENCE: 21
aaatacgaga tccaccgaga ctccacactg gacccctccc tgatggagat gacagaggct     60
gccctgcgcc tgctgagcag gaaccccgc ggcttcttcc tcttcgtgga gggtggtcgc    120
atcgaccatg gtcatcatga aagcagggct taccgggcac tgactgagac gatcatgttc    180
gacgacgcca ttgagagggc gggccagctc accagcgagg aggacacgct gagcctcgtc    240
actgccgacc actcccacgt cttctccttc ggaggctacc ccctgcgagg gagctccatc    300
ttcgggctgg cccctggcaa ggcccgggac aggaaggcct acacggtcct cctatacgga    360
aacggtccag gctatgtgct caaggacggc gcccggccgg atgttaccga gagcgagagc    420
gggagccccg agtatcggca gcagtcagca gtgcccctgg acgaagagac ccacgcaggc    480
gaggacgtgg cggtgttcgc gcgcggcccg caggcgttaa cctggttcac ggcgtgcagg    540
agcagacctt catagcgcac gtcatggcct tcgccgcctg cctggagccc tacaccgcct    600
gcgacctggc gcccccgcc ggcaccaccg acgccgcgca cccgggttac tctagataga    660
ttgtatcggc gctgttcctg c                                              681

<210> SEQ ID NO 22
<211> LENGTH: 683
<212> TYPE: DNA
<213> ORGANISM: Artificial Sequence
<220> FEATURE:
<223> OTHER INFORMATION: Oligonucleotide

<400> SEQUENCE: 22
aaatacgaga tccaccgaga ctccacactg gacccctccc tgatggagat gacagaggct     60
gccctgcgcc tgctgagcag gaaccccgc ggcttcttcc tcttcgtgga gggtggtcgc    120
atcgaccatg gtcatcatga aagcagggct taccgggcac tgactgagac gatcatgttc    180
gacgacgcca ttgagagggc gggccagctc accagcgagg aggacacgct gagcctcgtc    240
actgccgacc actcccacgt cttctccttc ggaggctacc ccctgcgagg gagctccatc    300
ttcgggctgg cccctggcaa ggcccgggac aggaaggcct acacggtcct cctatacgga    360
aacggtccag gctatgtgct caaggacggc gcccggccgg atgttaccga gagcgagagc    420
gggagccccg agtatcggca gcagtcagca gtgcccctgg acgaagagac ccacgcaggc    480
gaggacgtgg cggtgttcgc gcgcggcccg ttaacaggcg cacctggttc acggcgtgca    540
ggagcagacc ttcatagcgc acgtcatggc cttcgccgcc tgcctggagc cctacaccgc    600
ctgcgacctg gcgcccccg ccggcaccac cgacgccgcg cacccgggtt actctagata    660
gattgtatcg gcgctgttcc tgc                                            683
```

<210> SEQ ID NO 23
<211> LENGTH: 683
<212> TYPE: DNA
<213> ORGANISM: Artificial Sequence
<220> FEATURE:
<223> OTHER INFORMATION: Oligonucleotide

<400> SEQUENCE: 23

```
aaatacgaga tccaccgaga ctccacactg gaccccctccc tgatggagat gacagaggct      60
gccctgcgcc tgctgagcag gaaccccccgc ggcttcttcc tcttcgtgga gggtggtcgc     120
atcgaccatg gtcatcatga aagcagggct taccgggcac tgactgagac gatcatgttc     180
gacgacgcca ttgagagggc gggccagctc accagcgagg aggacacgct gagcctcgtc     240
actgccgacc actcccacgt cttctccttc ggaggctacc ccctgcgagg gagctccatc     300
ttcgggctgg ccctggcaa ggcccgggac aggaaggcct acacggtcct cctatacgga     360
aacggtccag gctatgtgct caaggacggc gcccggccgg atgttaccga gagcgagagc     420
gggagccccg agtatcggca gcagtcagca gtgcccctgg acgaagagac ccacgcaggc     480
gaggacgtgg cggtgttcgc gcgttaacgg cccgcaggcg cacctggttc acggcgtgca     540
ggagcagacc ttcatagcgc acgtcatggc cttcgccgcc tgcctggagc cctacaccgc     600
ctgcgacctg gcgcccccccg ccggcaccac cgacgccgcg cacccgggtt actctagata     660
gattgtatcg gcgctgttcc tgc                                              683
```

<210> SEQ ID NO 24
<211> LENGTH: 681
<212> TYPE: DNA
<213> ORGANISM: Artificial Sequence
<220> FEATURE:
<223> OTHER INFORMATION: Oligonucleotide

<400> SEQUENCE: 24

```
aaatacgaga tccaccgaga ctccacactg gaccccctccc tgatggagat gacagaggct      60
gccctgcgcc tgctgagcag gaaccccccgc ggcttcttcc tcttcgtgga gggtggtcgc     120
atcgaccatg gtcatcatga aagcagggct taccgggcac tgactgagac gatcatgttc     180
gacgacgcca ttgagagggc gggccagctc accagcgagg aggacacgct gagcctcgtc     240
actgccgacc actcccacgt cttctccttc ggaggctacc ccctgcgagg gagctccatc     300
ttcgggctgg ccctggcaa ggcccgggac aggaaggcct acacggtcct cctatacgga     360
aacggtccag gctatgtgct caaggacggc gcccggccgg atgttaccga gagcgagagc     420
gggagccccg agtatcggca gcagtcagca gtgcccctgg acgaagagac ccacgcaggc     480
gaggacgtgg cggtgttaac gcgcgcggcc cgcaggcgca cctggttcac ggcgtgcagg     540
agcagacctt catagcgcac gtcatggcct tcgccgcctg cctggagccc tacaccgcct     600
gcgacctggc gcccccgcc ggcaccaccg acgccgcgca cccgggttac tctagataga     660
ttgtatcggc gctgttcctg c                                                681
```

<210> SEQ ID NO 25
<211> LENGTH: 683
<212> TYPE: DNA
<213> ORGANISM: Artificial Sequence
<220> FEATURE:
<223> OTHER INFORMATION: Oligonucleotide

<400> SEQUENCE: 25

```
aaatacgaga tccaccgaga ctccacactg gaccccctccc tgatggagat gacagaggct    60
gccctgcgcc tgctgagcag gaaccccgc ggcttcttcc tcttcgtgga gggtggtcgc   120
atcgaccatg gtcatcatga aagcagggct taccgggcac tgactgagac gatcatgttc   180
gacgacgcca ttgagagggc gggccagctc accagcgagg aggacacgct gagcctcgtc   240
actgccgacc actcccacgt cttctccttc ggaggctacc ccctgcgagg gagctccatc   300
ttcgggctgg cccctggcaa ggcccgggac aggaaggcct acacggtcct cctatacgga   360
aacggtccag gctatgtgct caaggacggc gcccggccgg atgttaccga gagcgagagc   420
gggagccccg agtatcggca gcagtcagca gtgcccctgg acgaagagac ccacgcaggc   480
gaggacgtta acggcggtgt tcgcgcgcgg cccgcaggcg cacctggttc acggcgtgca   540
ggagcagacc ttcatagcgc acgtcatggc cttcgccgcc tgcctggagc cctacaccgc   600
ctgcgacctg gcgccccccg ccggcaccac cgacgccgcg cacccgggtt actctagata   660
gattgtatcg gcgctgttcc tgc                                          683
```

<210> SEQ ID NO 26
<211> LENGTH: 683
<212> TYPE: DNA
<213> ORGANISM: Artificial Sequence
<220> FEATURE:
<223> OTHER INFORMATION: Oligonucleotide

<400> SEQUENCE: 26

```
aaatacgaga tccaccgaga ctccacactg gaccccctccc tgatggagat gacagaggct    60
gccctgcgcc tgctgagcag gaaccccgc ggcttcttcc tcttcgtgga gggtggtcgc   120
atcgaccatg gtcatcatga aagcagggct taccgggcac tgactgagac gatcatgttc   180
gacgacgcca ttgagagggc gggccagctc accagcgagg aggacacgct gagcctcgtc   240
actgccgacc actcccacgt cttctccttc ggaggctacc ccctgcgagg gagctccatc   300
ttcgggctgg cccctggcaa ggcccgggac aggaaggcct acacggtcct cctatacgga   360
aacggtccag gctatgtgct caaggacggc gcccggccgg atgttaccga gagcgagagc   420
gggagccccg agtatcggca gcagtcagca gtgcccctgg acgaagagac ccacgcaggt   480
taacgaggac gtggcggtgt tcgcgcgcgg cccgcaggcg cacctggttc acggcgtgca   540
ggagcagacc ttcatagcgc acgtcatggc cttcgccgcc tgcctggagc cctacaccgc   600
ctgcgacctg gcgccccccg ccggcaccac cgacgccgcg cacccgggtt actctagata   660
gattgtatcg gcgctgttcc tgc                                          683
```

<210> SEQ ID NO 27
<211> LENGTH: 685
<212> TYPE: DNA
<213> ORGANISM: Artificial Sequence
<220> FEATURE:
<223> OTHER INFORMATION: Oligonucleotide

<400> SEQUENCE: 27

```
aaatacgaga tccaccgaga ctccacactg gaccccctccc tgatggagat gacagaggct    60
gccctgcgcc tgctgagcag gaaccccgc ggcttcttcc tcttcgtgga gggtggtcgc   120
atcgaccatg gtcatcatga aagcagggct taccgggcac tgactgagac gatcatgttc   180
gacgacgcca ttgagagggc gggccagctc accagcgagg aggacacgct gagcctcgtc   240
actgccgacc actcccacgt cttctccttc ggaggctacc ccctgcgagg gagctccatc   300
ttcgggctgg cccctggcaa ggcccgggac aggaaggcct acacggtcct cctatacgga   360
```

```
aacggtccag gctatgtgct caaggacggc gcccggccgg atgttaccga gagcgagagc    420
gggagccccg agtatcggca gcagtcagca gtgcccctgg acgaagagac ccagttaacc    480
gcaggcgagg acgtggcggt gttcgcgcgc ggcccgcagg cgcacctggt tcacggcgtg    540
caggagcaga ccttcatagc gcacgtcatg gccttcgccg cctgcctgga gccctacacc    600
gcctgcgacc tggcgccccc cgccggcacc accgacgccg cgcacccggg ttactctaga    660
tagattgtat cggcgctgtt cctgc                                          685
```

<210> SEQ ID NO 28
<211> LENGTH: 684
<212> TYPE: DNA
<213> ORGANISM: Artificial Sequence
<220> FEATURE:
<223> OTHER INFORMATION: Oligonucleotide

<400> SEQUENCE: 28

```
aaatacgaga tccaccgaga ctccacactg gacccctccc tgatggagat gacagaggct     60
gccctgcgcc tgctgagcag gaaccccgc ggcttcttcc tcttcgtgga gggtggtcgc    120
atcgaccatg gtcatcatga aagcagggct taccgggcac tgactgagac gatcatgttc    180
gacgacgcca ttgagagggc gggccagctc accagcgagg aggacacgct gagcctcgtc    240
actgccgacc actcccacgt cttctccttc ggaggctacc ccctgcgagg gagctccatc    300
ttcgggctgg cccctggcaa ggcccgggac aggaaggcct acacggtcct cctatacgga    360
aacggtccag gctatgtgct caaggacggc gcccggccgg atgttaccga gagcgagagc    420
gggagccccg agtatcggca gcagtcagca gtgcccctgt taacgacgaa gagacccacg    480
caggcgagga cgtggcggtg ttcgcgcgcg ccccgcaggc gcacctggtt cacggcgtgc    540
aggagcagac cttcatagcg cacgtcatgg ccttcgccgc ctgcctggag ccctacaccg    600
cctgcgacct ggcgcccccc gccggcacca ccgacgccgc gcacccgggt tactctagat    660
agattgtatc ggcgctgttc ctgc                                           684
```

<210> SEQ ID NO 29
<211> LENGTH: 679
<212> TYPE: DNA
<213> ORGANISM: Artificial Sequence
<220> FEATURE:
<223> OTHER INFORMATION: Oligonucleotide

<400> SEQUENCE: 29

```
aaatacgaga tccaccgaga ctccacactg gacccctccc tgatggagat gacagaggct     60
gccctgcgcc tgctgagcag gaaccccgc ggcttcttcc tcttcgtgga gggtggtcgc    120
atcgaccatg gtcatcatga aagcagggct taccgggcac tgactgagac gatcatgttc    180
gacgacgcca ttgagagggc gggccagctc accagcgagg aggacacgct gagcctcgtc    240
actgccgacc actcccacgt cttctccttc ggaggctacc ccctgcgagg gagctccatc    300
ttcgggctgg cccctggcaa ggcccgggac aggaaggcct acacggtcct cctatacgga    360
aacggtccag gctatgtgct caaggacggc gcccggccgg atgttaccga gagcgagagc    420
gggagccccg agtatcggca gcagttaaca gtgcccctgg acgaagagac ccacgcaggc    480
gaggacgtgg cggtgttcgc gcgcggcccg caggcgcacc tggttcacgg cgtgcaggag    540
cagaccttca tagcgcacgt catggccttc gccgcctgcc tggagcccta caccgcctgc    600
gacctggcgc ccccgccgg caccaccgac gccgcgcacc cgggttactc tagatagatt    660
```

```
gtatcggcgc tgttcctgc                                               679
```

<210> SEQ ID NO 30
<211> LENGTH: 683
<212> TYPE: DNA
<213> ORGANISM: Artificial Sequence
<220> FEATURE:
<223> OTHER INFORMATION: Oligonucleotide

<400> SEQUENCE: 30

```
aaatacgaga tccaccgaga ctccacactg gaccccctccc tgatggagat gacagaggct    60
gccctgcgcc tgctgagcag gaaccccgc ggcttcttcc tcttcgtgga gggtggtcgc    120
atcgaccatg gtcatcatga aagcagggct taccgggcac tgactgagac gatcatgttc    180
gacgacgcca ttgagagggc gggccagctc accagcgagg aggacacgct gagcctcgtc    240
actgccgacc actcccacgt cttctccttc ggaggctacc ccctgcgagg gagctccatc    300
ttcgggctgg cccctggcaa ggcccgggac aggaaggcct acacggtcct cctatacgga    360
aacggtccag gctatgtgct caaggacggc gcccggccgg atgttaccga gagcgagagc    420
gggagccccg agtatcggtt aacagcagtc agcagtgccc ctggacgaag agacccacgc    480
aggcgaggac gtggcggtgt tcgcgcgcgg cccgcaggcg cacctggttc acggcgtgca    540
ggagcagacc ttcatagcgc acgtcatggc cttcgccgcc tgcctggagc cctacaccgc    600
ctgcgacctg gcgcccccg ccggcaccac cgacgccgcg cacccgggtt actctagata    660
gattgtatcg gcgctgttcc tgc                                           683
```

<210> SEQ ID NO 31
<211> LENGTH: 683
<212> TYPE: DNA
<213> ORGANISM: Artificial Sequence
<220> FEATURE:
<223> OTHER INFORMATION: Oligonucleotide

<400> SEQUENCE: 31

```
aaatacgaga tccaccgaga ctccacactg gaccccctccc tgatggagat gacagaggct    60
gccctgcgcc tgctgagcag gaaccccgc ggcttcttcc tcttcgtgga gggtggtcgc    120
atcgaccatg gtcatcatga aagcagggct taccgggcac tgactgagac gatcatgttc    180
gacgacgcca ttgagagggc gggccagctc accagcgagg aggacacgct gagcctcgtc    240
actgccgacc actcccacgt cttctccttc ggaggctacc ccctgcgagg gagctccatc    300
ttcgggctgg cccctggcaa ggcccgggac aggaaggcct acacggtcct cctatacgga    360
aacggtccag gctatgtgct caaggacggc gcccggccgg atgttaccga gagcgagagc    420
gggagccccg ttaacgtatc ggcagcagtc agcagtgccc ctggacgaag agacccacgc    480
aggcgaggac gtggcggtgt tcgcgcgcgg cccgcaggcg cacctggttc acggcgtgca    540
ggagcagacc ttcatagcgc acgtcatggc cttcgccgcc tgcctggagc cctacaccgc    600
ctgcgacctg gcgcccccg ccggcaccac cgacgccgcg cacccgggtt actctagata    660
gattgtatcg gcgctgttcc tgc                                           683
```

<210> SEQ ID NO 32
<211> LENGTH: 683
<212> TYPE: DNA
<213> ORGANISM: Artificial Sequence
<220> FEATURE:
<223> OTHER INFORMATION: Oligonucleotide

<400> SEQUENCE: 32

-continued

```
aaatacgaga tccaccgaga ctccacactg gacccctccc tgatggagat gacagaggct      60
gccctgcgcc tgctgagcag gaaccccgc ggcttcttcc tcttcgtgga gggtggtcgc     120
atcgaccatg gtcatcatga aagcagggct taccgggcac tgactgagac gatcatgttc    180
gacgacgcca ttgagagggc gggccagctc accagcgagg aggacacgct gagcctcgtc    240
actgccgacc actcccacgt cttctccttc ggaggctacc ccctgcgagg gagctccatc    300
ttcgggctgg cccctggcaa ggcccgggac aggaaggcct acacggtcct cctatacgga    360
aacggtccag gctatgtgct caaggacggc gcccggccgg atgttaccga gagcgagagc    420
gggttaacgc cccgagtatc ggcagcagtc agcagtgccc ctggacgaag agacccacgc    480
aggcgaggac gtggcggtgt tcgcgcgcgg cccgcaggcg cacctggttc acggcgtgca    540
ggagcagacc ttcatagcgc acgtcatggc cttcgccgcc tgcctggagc cctacaccgc    600
ctgcgacctg gcgccccccg ccggcaccac cgacgccgcg cacccgggtt actctagata    660
gattgtatcg gcgctgttcc tgc                                             683
```

<210> SEQ ID NO 33
<211> LENGTH: 683
<212> TYPE: DNA
<213> ORGANISM: Artificial Sequence
<220> FEATURE:
<223> OTHER INFORMATION: Oligonucleotide

<400> SEQUENCE: 33

```
aaatacgaga tccaccgaga ctccacactg gacccctccc tgatggagat gacagaggct      60
gccctgcgcc tgctgagcag gaaccccgc ggcttcttcc tcttcgtgga gggtggtcgc     120
atcgaccatg gtcatcatga aagcagggct taccgggcac tgactgagac gatcatgttc    180
gacgacgcca ttgagagggc gggccagctc accagcgagg aggacacgct gagcctcgtc    240
actgccgacc actcccacgt cttctccttc ggaggctacc ccctgcgagg gagctccatc    300
ttcgggctgg cccctggcaa ggcccgggac aggaaggcct acacggtcct cctatacgga    360
aacggtccag gctatgtgct caaggacggc gcccggccgg atgttaccga gagttaacga    420
gagcgggagc cccgagtatc ggcagcagtc agcagtgccc ctggacgaag agacccacgc    480
aggcgaggac gtggcggtgt tcgcgcgcgg cccgcaggcg cacctggttc acggcgtgca    540
ggagcagacc ttcatagcgc acgtcatggc cttcgccgcc tgcctggagc cctacaccgc    600
ctgcgacctg gcgccccccg ccggcaccac cgacgccgcg cacccgggtt actctagata    660
gattgtatcg gcgctgttcc tgc                                             683
```

<210> SEQ ID NO 34
<211> LENGTH: 679
<212> TYPE: DNA
<213> ORGANISM: Artificial Sequence
<220> FEATURE:
<223> OTHER INFORMATION: Oligonucleotide

<400> SEQUENCE: 34

```
aaatacgaga tccaccgaga ctccacactg gacccctccc tgatggagat gacagaggct      60
gccctgcgcc tgctgagcag gaaccccgc ggcttcttcc tcttcgtgga gggtggtcgc     120
atcgaccatg gtcatcatga aagcagggct taccgggcac tgactgagac gatcatgttc    180
gacgacgcca ttgagagggc gggccagctc accagcgagg aggacacgct gagcctcgtc    240
actgccgacc actcccacgt cttctccttc ggaggctacc ccctgcgagg gagctccatc    300
```

-continued

| | |
|---|---|
| ttcgggctgg cccctggcaa ggcccgggac aggaaggcct acacggtcct cctatacgga | 360 |
| aacggtccag gctatgtgct caaggacggc gcccggccgg atgttaacga gagcgagagc | 420 |
| gggagcccg agtatcggca gcagtcagca gtgcccctgg acgaagagac ccacgcaggc | 480 |
| gaggacgtgg cggtgttcgc gcgcggcccg caggcgcacc tggttcacgg cgtgcaggag | 540 |
| cagaccttca tagcgcacgt catggccttc gccgcctgcc tggagcccta caccgcctgc | 600 |
| gacctggcgc ccccgccgg caccaccgac gccgcgcacc cgggttactc tagatagatt | 660 |
| gtatcggcgc tgttcctgc | 679 |

<210> SEQ ID NO 35
<211> LENGTH: 683
<212> TYPE: DNA
<213> ORGANISM: Artificial Sequence
<220> FEATURE:
<223> OTHER INFORMATION: Oligonucleotide

<400> SEQUENCE: 35

| | |
|---|---|
| aaatacgaga tccaccgaga ctccacactg gaccctccc tgatggagat gacagaggct | 60 |
| gccctgcgcc tgctgagcag gaaccccgc ggcttcttcc tcttcgtgga gggtggtcgc | 120 |
| atcgaccatg gtcatcatga aagcagggct taccgggcac tgactgagac gatcatgttc | 180 |
| gacgacgcca ttgagagggc gggccagctc accagcgagg aggacacgct gagcctcgtc | 240 |
| actgccgacc actcccacgt cttctccttc ggaggctacc ccctgcgagg gagctccatc | 300 |
| ttcgggctgg cccctggcaa ggcccgggac aggaaggcct acacggtcct cctatacgga | 360 |
| aacggtccag gctatgtgtt aactcaagga cggcgcccgg ccggatgtta ccgagagcga | 420 |
| gagcgggagc ccgagtatc ggcagcagtc agcagtgccc ctggacgaag agacccacgc | 480 |
| aggcgaggac gtggcggtgt tcgcgcgcgg cccgcaggcg cacctggttc acggcgtgca | 540 |
| ggagcagacc ttcatagcgc acgtcatggc cttcgccgcc tgcctggagc cctacaccgc | 600 |
| ctgcgacctg gcgccccccg ccggcaccac cgacgccgcg cacccgggtt actctagata | 660 |
| gattgtatcg gcgctgttcc tgc | 683 |

<210> SEQ ID NO 36
<211> LENGTH: 683
<212> TYPE: DNA
<213> ORGANISM: Artificial Sequence
<220> FEATURE:
<223> OTHER INFORMATION: Oligonucleotide

<400> SEQUENCE: 36

| | |
|---|---|
| aaatacgaga tccaccgaga ctccacactg gaccctccc tgatggagat gacagaggct | 60 |
| gccctgcgcc tgctgagcag gaaccccgc ggcttcttcc tcttcgtgga gggtggtcgc | 120 |
| atcgaccatg gtcatcatga aagcagggct taccgggcac tgactgagac gatcatgttc | 180 |
| gacgacgcca ttgagagggc gggccagctc accagcgagg aggacacgct gagcctcgtc | 240 |
| actgccgacc actcccacgt cttctccttc ggaggctacc ccctgcgagg gagctccatc | 300 |
| ttcgggctgg cccctggcaa ggcccgggac aggaaggcct acacggtcct cctatacgga | 360 |
| aacggtccag gttaactatg tgctcaagga cggcgcccgg ccggatgtta ccgagagcga | 420 |
| gagcgggagc ccgagtatc ggcagcagtc agcagtgccc ctggacgaag agacccacgc | 480 |
| aggcgaggac gtggcggtgt tcgcgcgcgg cccgcaggcg cacctggttc acggcgtgca | 540 |
| ggagcagacc ttcatagcgc acgtcatggc cttcgccgcc tgcctggagc cctacaccgc | 600 |
| ctgcgacctg gcgccccccg ccggcaccac cgacgccgcg cacccgggtt actctagata | 660 |

```
gattgtatcg gcgctgttcc tgc                                              683

<210> SEQ ID NO 37
<211> LENGTH: 679
<212> TYPE: DNA
<213> ORGANISM: Artificial Sequence
<220> FEATURE:
<223> OTHER INFORMATION: Oligonucleotide

<400> SEQUENCE: 37
aaatacgaga tccaccgaga ctccacactg gacccctccc tgatggagat gacagaggct       60
gccctgcgcc tgctgagcag gaaccccgc ggcttcttcc tcttcgtgga gggtggtcgc      120
atcgaccatg gtcatcatga aagcagggct taccgggcac tgactgagac gatcatgttc      180
gacgacgcca ttgagagggc gggccagctc accagcgagg aggacacgct gagcctcgtc      240
actgccgacc actcccacgt cttctccttc ggaggctacc ccctgcgagg gagctccatc      300
ttcgggctgg cccctggcaa ggcccgggac aggaaggcct acacggtcct cctatacgtt      360
aacggtccag gctatgtgct caaggacggc gcccggccgg atgttaccga gagcgagagc      420
gggagccccg agtatcggca gcagtcagca gtgcccctgg acgaagagac ccacgcaggc      480
gaggacgtgg cggtgttcgc gcgcggcccg caggcgcacc tggttcacgg cgtgcaggag      540
cagaccttca tagcgcacgt catggccttc gccgcctgcc tggagcccta caccgcctgc      600
gacctggcgc cccccgccgg caccaccgac gccgcgcacc cgggttactc tagatagatt      660
gtatcggcgc tgttcctgc                                                   679

<210> SEQ ID NO 38
<211> LENGTH: 682
<212> TYPE: DNA
<213> ORGANISM: Artificial Sequence
<220> FEATURE:
<223> OTHER INFORMATION: Oligonucleotide

<400> SEQUENCE: 38
aaatacgaga tccaccgaga ctccacactg gacccctccc tgatggagat gacagaggct       60
gccctgcgcc tgctgagcag gaaccccgc ggcttcttcc tcttcgtgga gggtggtcgc      120
atcgaccatg gtcatcatga aagcagggct taccgggcac tgactgagac gatcatgttc      180
gacgacgcca ttgagagggc gggccagctc accagcgagg aggacacgct gagcctcgtc      240
actgccgacc actcccacgt cttctccttc ggaggctacc ccctgcgagg gagctccatc      300
ttcgggctgg cccctggcaa ggcccgggac aggaaggcct acacggttaa cctcctatac      360
ggaaacggtc caggctatgt gctcaaggac ggcgcccggc cggatgttac cgagagcgag      420
agcgggagcc ccgagtatcg gcagcagtca gcagtgcccc tggacgaaga gacccacgca      480
ggcgaggacg tggcggtgtt cgcgcgcggc ccgcaggcgc acctggttca cggcgtgcag      540
gagcagacct tcatagcgca cgtcatggcc ttcgccgcct gcctggagcc ctacaccgcc      600
tgcgacctgg cgcccccgc cggcaccacc gacgccgcgc acccgggtta ctctagatag      660
attgtatcgg cgctgttcct gc                                               682

<210> SEQ ID NO 39
<211> LENGTH: 684
<212> TYPE: DNA
<213> ORGANISM: Artificial Sequence
<220> FEATURE:
<223> OTHER INFORMATION: Oligonucleotide
```

<400> SEQUENCE: 39

```
aaatacgaga tccaccgaga ctccacactg gacccctccc tgatggagat gacagaggct    60
gccctgcgcc tgctgagcag gaaccccgc ggcttcttcc tcttcgtgga gggtggtcgc   120
atcgaccatg gtcatcatga aagcagggct taccgggcac tgactgagac gatcatgttc   180
gacgacgcca ttgagagggc gggccagctc accagcgagg aggacacgct gagcctcgtc   240
actgccgacc actcccacgt cttctccttc ggaggctacc ccctgcgagg gagctccatc   300
ttcgggctgg cccctggcaa ggcccgggac aggaagttaa cgcctacacg gtcctcctat   360
acggaaacgg tccaggctat gtgctcaagg acggcgcccg gccggatgtt accgagagcg   420
agagcgggag ccccgagtat cggcagcagt cagcagtgcc cctggacgaa gagacccacg   480
caggcgagga cgtggcggtg ttcgcgcgcg gcccgcaggc gcacctggtt cacggcgtgc   540
aggagcagac cttcatagcg cacgtcatgg ccttcgccgc ctgcctggag ccctacaccg   600
cctgcgacct ggcgcccccc gccggcacca ccgacgccgc gcacccgggt tactctagat   660
agattgtatc ggcgctgttc ctgc                                          684
```

<210> SEQ ID NO 40
<211> LENGTH: 682
<212> TYPE: DNA
<213> ORGANISM: Artificial Sequence
<220> FEATURE:
<223> OTHER INFORMATION: Oligonucleotide

<400> SEQUENCE: 40

```
aaatacgaga tccaccgaga ctccacactg gacccctccc tgatggagat gacagaggct    60
gccctgcgcc tgctgagcag gaaccccgc ggcttcttcc tcttcgtgga gggtggtcgc   120
atcgaccatg gtcatcatga aagcagggct taccgggcac tgactgagac gatcatgttc   180
gacgacgcca ttgagagggc gggccagctc accagcgagg aggacacgct gagcctcgtc   240
actgccgacc actcccacgt cttctccttc ggaggctacc ccctgcgagg gagctccatc   300
ttcgggctgg cccctggcaa ggcccgggtt aacaggaagg cctacacggt cctcctatac   360
ggaaacggtc caggctatgt gctcaaggac ggcgcccggc cggatgttac cgagagcgag   420
agcgggagcc ccgagtatcg gcagcagtca gcagtgcccc tggacgaaga gacccacgca   480
ggcgaggacg tggcggtgtt cgcgcgcggc ccgcaggcgc acctggttca cggcgtgcag   540
gagcagacct tcatagcgca cgtcatggcc ttcgccgcct gcctggagcc ctacaccgcc   600
tgcgacctgg cgcccccgc cggcaccacc gacgccgcg acccgggtta ctctagatag   660
attgtatcgg cgctgttcct gc                                            682
```

<210> SEQ ID NO 41
<211> LENGTH: 684
<212> TYPE: DNA
<213> ORGANISM: Artificial Sequence
<220> FEATURE:
<223> OTHER INFORMATION: Oligonucleotide

<400> SEQUENCE: 41

```
aaatacgaga tccaccgaga ctccacactg gacccctccc tgatggagat gacagaggct    60
gccctgcgcc tgctgagcag gaaccccgc ggcttcttcc tcttcgtgga gggtggtcgc   120
atcgaccatg gtcatcatga aagcagggct taccgggcac tgactgagac gatcatgttc   180
gacgacgcca ttgagagggc gggccagctc accagcgagg aggacacgct gagcctcgtc   240
actgccgacc actcccacgt cttctccttc ggaggctacc ccctgcgagg gagctccatc   300
```

```
ttcgggctgg cccctggcaa gttaacgccc gggacaggaa ggcctacacg gtcctcctat    360
acggaaacgg tccaggctat gtgctcaagg acggcgcccg gccggatgtt accgagagcg    420
agagcgggag ccccgagtat cggcagcagt cagcagtgcc cctggacgaa gagacccacg    480
caggcgagga cgtggcggtg ttcgcgcgcg gcccgcaggc gcacctggtt cacggcgtgc    540
aggagcagac cttcatagcg cacgtcatgg ccttcgccgc ctgcctggag ccctacaccg    600
cctgcgacct ggcgcccccc gccggcacca ccgacgccgc gcacccgggt tactctagat    660
agattgtatc ggcgctgttc ctgc                                           684
```

```
<210> SEQ ID NO 42
<211> LENGTH: 683
<212> TYPE: DNA
<213> ORGANISM: Artificial Sequence
<220> FEATURE:
<223> OTHER INFORMATION: Oligonucleotide

<400> SEQUENCE: 42
aaatacgaga tccaccgaga ctccacactg gacccctccc tgatggagat gacagaggct     60
gccctgcgcc tgctgagcag gaaccccgc ggcttcttcc tcttcgtgga gggtggtcgc    120
atcgaccatg gtcatcatga aagcagggct taccgggcac tgactgagac gatcatgttc    180
gacgacgcca ttgagagggc gggccagctc accagcgagg aggacacgct gagcctcgtc    240
actgccgacc actcccacgt cttctccttc ggaggctacc ccctgcgagg gagctccatc    300
ttcgggctgg ttaaccccctg caaggcccg ggacaggaag gcctacacgg tcctcctata    360
cggaaacggt ccaggctatg tgctcaagga cggcgcccgg ccggatgtta ccgagagcga    420
gagcgggagc cccgagtatc ggcagcagtc agcagtgccc ctggacgaag agacccacgc    480
aggcgaggac gtggcggtgt tcgcgcgcgg cccgcaggcg cacctggttc acggcgtgca    540
ggagcagacc ttcatagcgc acgtcatggc cttcgccgcc tgcctggagc cctacaccgc    600
ctgcgacctg gcgcccccg ccggcaccac cgacgccgcg cacccgggtt actctagata    660
gattgtatcg gcgctgttcc tgc                                           683
```

```
<210> SEQ ID NO 43
<211> LENGTH: 682
<212> TYPE: DNA
<213> ORGANISM: Artificial Sequence
<220> FEATURE:
<223> OTHER INFORMATION: Oligonucleotide

<400> SEQUENCE: 43
aaatacgaga tccaccgaga ctccacactg gacccctccc tgatggagat gacagaggct     60
gccctgcgcc tgctgagcag gaaccccgc ggcttcttcc tcttcgtgga gggtggtcgc    120
atcgaccatg gtcatcatga aagcagggct taccgggcac tgactgagac gatcatgttc    180
gacgacgcca ttgagagggc gggccagctc accagcgagg aggacacgct gagcctcgtc    240
actgccgacc actcccacgt cttctccttc ggaggctacc ccctgcgagg gagctccatc    300
gttaacgggc tggcccctgg caaggcccgg acaggaagg cctacacggt cctcctatac    360
ggaaacggtc caggctatgt gctcaaggac ggcgcccggc cggatgttac cgagagcgag    420
agcgggagcc ccgagtatcg gcagcagtca gcagtgccc tggacgaaga gacccacgca    480
ggcgaggacg tggcggtgtt cgcgcgcgg ccgcaggcgc acctggttca cggcgtgcag    540
gagcagacct tcatagcgca cgtcatggcc ttcgccgcct gcctggagcc ctacaccgcc    600
```

```
tgcgacctgg cgccccccgc cggcaccacc gacgccgcgc acccgggtta ctctagatag    660
attgtatcgg cgctgttcct gc                                            682
```

<210> SEQ ID NO 44
<211> LENGTH: 683
<212> TYPE: DNA
<213> ORGANISM: Artificial Sequence
<220> FEATURE:
<223> OTHER INFORMATION: Oligonucleotide

<400> SEQUENCE: 44

```
aaatacgaga tccaccgaga ctccacactg gacccctccc tgatggagat gacagaggct     60
gccctgcgcc tgctgagcag gaaccccgc ggcttcttcc tcttcgtgga gggtggtcgc    120
atcgaccatg gtcatcatga aagcagggct taccgggcac tgactgagac gatcatgttc    180
gacgacgcca ttgagagggc gggccagctc accagcgagg aggacacgct gagcctcgtc    240
actgccgacc actcccacgt cttctccttc ggaggctacc ccctgcgagg gagttaactc    300
catcttcggg ctggcccctg gcaaggcccg ggacaggaag gcctacacgg tcctcctata    360
cggaaacggt ccaggctatg tgctcaagga cggcgcccgg ccggatgtta ccgagagcga    420
gagcgggagc cccgagtatc ggcagcagtc agcagtgccc ctggacgaag acccacgc     480 aggcgaggac gtggcggtgt tcgcgcgcgg cccgcaggcg cacctggttc acggcgtgca    540
ggagcagacc ttcatagcgc acgtcatggc cttcgccgcc tgcctggagc cctacaccgc    600
ctgcgacctg gcgccccccg ccggcaccac cgacgccgcg cacccgggtt actctagata    660
gattgtatcg gcgctgttcc tgc                                           683
```

<210> SEQ ID NO 45
<211> LENGTH: 683
<212> TYPE: DNA
<213> ORGANISM: Artificial Sequence
<220> FEATURE:
<223> OTHER INFORMATION: Oligonucleotide

<400> SEQUENCE: 45

```
aaatacgaga tccaccgaga ctccacactg gacccctccc tgatggagat gacagaggct     60
gccctgcgcc tgctgagcag gaaccccgc ggcttcttcc tcttcgtgga gggtggtcgc    120
atcgaccatg gtcatcatga aagcagggct taccgggcac tgactgagac gatcatgttc    180
gacgacgcca ttgagagggc gggccagctc accagcgagg aggacacgct gagcctcgtc    240
actgccgacc actcccacgt cttctccttc ggaggctacc ccctgttaac gagggagctc    300
catcttcggg ctggcccctg gcaaggcccg ggacaggaag gcctacacgg tcctcctata    360
cggaaacggt ccaggctatg tgctcaagga cggcgcccgg ccggatgtta ccgagagcga    420
gagcgggagc cccgagtatc ggcagcagtc agcagtgccc ctggacgaag acccacgc     480 aggcgaggac gtggcggtgt tcgcgcgcgg cccgcaggcg cacctggttc acggcgtgca    540
ggagcagacc ttcatagcgc acgtcatggc cttcgccgcc tgcctggagc cctacaccgc    600
ctgcgacctg gcgccccccg ccggcaccac cgacgccgcg cacccgggtt actctagata    660
gattgtatcg gcgctgttcc tgc                                           683
```

<210> SEQ ID NO 46
<211> LENGTH: 10
<212> TYPE: DNA
<213> ORGANISM: Artificial Sequence
<220> FEATURE:
<223> OTHER INFORMATION: Oligonucleotide

```
<400> SEQUENCE: 46 gggamttycc                                                              10

<210> SEQ ID NO 47
<211> LENGTH: 10
<212> TYPE: DNA
<213> ORGANISM: Artificial Sequence
<220> FEATURE:
<223> OTHER INFORMATION: Oligonucleotide

<400> SEQUENCE: 47
agaatgttct                                                              10

<210> SEQ ID NO 48
<211> LENGTH: 15
<212> TYPE: DNA
<213> ORGANISM: Artificial Sequence
<220> FEATURE:
<223> OTHER INFORMATION: Oligonucleotide

<400> SEQUENCE: 48
tagtttcact ttccc                                                        15

<210> SEQ ID NO 49
<211> LENGTH: 20
<212> TYPE: DNA
<213> ORGANISM: Artificial Sequence
<220> FEATURE:
<223> OTHER INFORMATION: Oligonucleotide

<400> SEQUENCE: 49
ggacatgccc gggcatgtcc                                                   20

<210> SEQ ID NO 50
<211> LENGTH: 15
<212> TYPE: DNA
<213> ORGANISM: Artificial Sequence
<220> FEATURE:
<223> OTHER INFORMATION: Oligonucleotide

<400> SEQUENCE: 50
aagatcaaag ggggt                                                        15

<210> SEQ ID NO 51
<211> LENGTH: 9
<212> TYPE: DNA
<213> ORGANISM: Artificial Sequence
<220> FEATURE:
<223> OTHER INFORMATION: Oligonucleotide

<400> SEQUENCE: 51 agccagaca                                                                9

<210> SEQ ID NO 52
<211> LENGTH: 9
<212> TYPE: DNA
<213> ORGANISM: Artificial Sequence
<220> FEATURE:
<223> OTHER INFORMATION: Oligonucleotide

<400> SEQUENCE: 52 ggcgcsagc                                                                9

<210> SEQ ID NO 53
```

-continued

```
<211> LENGTH: 8
<212> TYPE: DNA
<213> ORGANISM: Artificial Sequence
<220> FEATURE:
<223> OTHER INFORMATION: Oligonucleotide

<400> SEQUENCE: 53 tgacgtma                                                                   8

<210> SEQ ID NO 54
<211> LENGTH: 12
<212> TYPE: DNA
<213> ORGANISM: Artificial Sequence
<220> FEATURE:
<223> OTHER INFORMATION: Oligonucleotide

<400> SEQUENCE: 54
aggacaaggt ca                                                             12

<210> SEQ ID NO 55
<211> LENGTH: 30
<212> TYPE: DNA
<213> ORGANISM: Artificial Sequence
<220> FEATURE:
<223> OTHER INFORMATION: Oligonucleotide

<400> SEQUENCE: 55
ggtcacagtg acctaggtca cagtgaccta                                          30

<210> SEQ ID NO 56
<211> LENGTH: 19
<212> TYPE: DNA
<213> ORGANISM: Artificial Sequence
<220> FEATURE:
<223> OTHER INFORMATION: Oligonucleotide

<400> SEQUENCE: 56
gcggtacatt ttgttctag                                                      19

<210> SEQ ID NO 57
<211> LENGTH: 30
<212> TYPE: DNA
<213> ORGANISM: Artificial Sequence
<220> FEATURE:
<223> OTHER INFORMATION: Primer

<400> SEQUENCE: 57
ctccggatcc aggctggaat gaacctggaa                                          30

<210> SEQ ID NO 58
<211> LENGTH: 30
<212> TYPE: DNA
<213> ORGANISM: Artificial Sequence
<220> FEATURE:
<223> OTHER INFORMATION: Primer

<400> SEQUENCE: 58
ctcaagcttt cacttttgat gaaacagaag                                          30

<210> SEQ ID NO 59
<211> LENGTH: 30
<212> TYPE: DNA
<213> ORGANISM: Artificial Sequence
<220> FEATURE:
<223> OTHER INFORMATION: Primer

<400> SEQUENCE: 59
```

-continued ctcgaattca tgttgaaaca caagcgccag                                                  30

<210> SEQ ID NO 60
<211> LENGTH: 30
<212> TYPE: DNA
<213> ORGANISM: Artificial Sequence
<220> FEATURE:
<223> OTHER INFORMATION: Primer

<400> SEQUENCE: 60
ctcggatcct cagactgtgg cagggaaacc                                                  30

<210> SEQ ID NO 61
<211> LENGTH: 30
<212> TYPE: DNA
<213> ORGANISM: Artificial Sequence
<220> FEATURE:
<223> OTHER INFORMATION: Primer

<400> SEQUENCE: 61
ctcgaattca tcggcatgat gaaggagttc                                                  30

<210> SEQ ID NO 62
<211> LENGTH: 31
<212> TYPE: DNA
<213> ORGANISM: Artificial Sequence
<220> FEATURE:
<223> OTHER INFORMATION: Primer

<400> SEQUENCE: 62
ctcaagcttt caggagatct cattgccaaa c                                                31

<210> SEQ ID NO 63
<211> LENGTH: 30
<212> TYPE: DNA
<213> ORGANISM: Artificial Sequence
<220> FEATURE:
<223> OTHER INFORMATION: Primer

<400> SEQUENCE: 63
ctcgaattcg gcatggccat ggacttggtt                                                  30

<210> SEQ ID NO 64
<211> LENGTH: 31
<212> TYPE: DNA
<213> ORGANISM: Artificial Sequence
<220> FEATURE:
<223> OTHER INFORMATION: Primer

<400> SEQUENCE: 64
ctcaagcttt tagacttcct gatcctcaaa g                                                31

<210> SEQ ID NO 65
<211> LENGTH: 30
<212> TYPE: DNA
<213> ORGANISM: Artificial Sequence
<220> FEATURE:
<223> OTHER INFORMATION: Primer

<400> SEQUENCE: 65
ctcgaattca tgaggaaaga catgatactg                                                  30

<210> SEQ ID NO 66
<211> LENGTH: 30
<212> TYPE: DNA

```
<213> ORGANISM: Artificial Sequence
<220> FEATURE:
<223> OTHER INFORMATION: Oligonucleotide

<400> SEQUENCE: 66 ctcaagctttt cagctgcaga tctcctggag                              30

<210> SEQ ID NO 67
<211> LENGTH: 31
<212> TYPE: DNA
<213> ORGANISM: Artificial Sequence
<220> FEATURE:
<223> OTHER INFORMATION: Primer

<400> SEQUENCE: 67
ctctgaattc atgactgcaa agatggaaac g                             31

<210> SEQ ID NO 68
<211> LENGTH: 31
<212> TYPE: DNA
<213> ORGANISM: Artificial Sequence
<220> FEATURE:
<223> OTHER INFORMATION: Primer

<400> SEQUENCE: 68
ctctaagctt gtcgatgggg gacaggggcg g                             31

<210> SEQ ID NO 69
<211> LENGTH: 33
<212> TYPE: DNA
<213> ORGANISM: Artificial Sequence
<220> FEATURE:
<223> OTHER INFORMATION: Primer

<400> SEQUENCE: 69
ctctggatcc tgaaattcaa gttacatgtg aat                           33

<210> SEQ ID NO 70
<211> LENGTH: 24
<212> TYPE: DNA
<213> ORGANISM: Artificial Sequence
<220> FEATURE:
<223> OTHER INFORMATION: Primer

<400> SEQUENCE: 70 aagagggat aaatctagag gcat                                      24

<210> SEQ ID NO 71
<211> LENGTH: 31
<212> TYPE: DNA
<213> ORGANISM: Artificial Sequence
<220> FEATURE:
<223> OTHER INFORMATION: Primer

<400> SEQUENCE: 71
tctcgaattc atctcccagc cgcagaaggg c                             31

<210> SEQ ID NO 72
<211> LENGTH: 31
<212> TYPE: DNA
<213> ORGANISM: Artificial Sequence
<220> FEATURE:
<223> OTHER INFORMATION: Oligonucleotide

<400> SEQUENCE: 72
tctcaagctt tcatggcttc tggggccctg g                             31
```

```
<210> SEQ ID NO 73
<211> LENGTH: 7
<212> TYPE: DNA
<213> ORGANISM: Artificial Sequence
<220> FEATURE:
<223> OTHER INFORMATION: Oligonucleotide

<400> SEQUENCE: 73 tgactaa                                                                  7

<210> SEQ ID NO 74
<211> LENGTH: 8
<212> TYPE: DNA
<213> ORGANISM: Artificial Sequence
<220> FEATURE:
<223> OTHER INFORMATION: Oligonucleotide

<400> SEQUENCE: 74 ctccccaa                                                                 8

<210> SEQ ID NO 75
<211> LENGTH: 9
<212> TYPE: DNA
<213> ORGANISM: Artificial Sequence
<220> FEATURE:
<223> OTHER INFORMATION: Oligonucleotide

<400> SEQUENCE: 75 gaccaccca                                                                9

<210> SEQ ID NO 76
<211> LENGTH: 13
<212> TYPE: DNA
<213> ORGANISM: Artificial Sequence
<220> FEATURE:
<223> OTHER INFORMATION: Oligonucleotide

<400> SEQUENCE: 76
aaccacracc rca                                                          13

<210> SEQ ID NO 77
<211> LENGTH: 9
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: 4, 5, 6
<223> OTHER INFORMATION: n = A,T,C or G

<400> SEQUENCE: 77 gccnnnggc                                                                9

<210> SEQ ID NO 78
<211> LENGTH: 6
<212> TYPE: DNA
<213> ORGANISM: Artificial Sequence
<220> FEATURE:
<223> OTHER INFORMATION: Oligonucleotide

<400> SEQUENCE: 78 cacctg                                                                   6

<210> SEQ ID NO 79
```

```
<211> LENGTH: 4
<212> TYPE: DNA
<213> ORGANISM: Artificial Sequence
<220> FEATURE:
<223> OTHER INFORMATION: Oligonucleotide

<400> SEQUENCE: 79 ggaw                                                                        4

<210> SEQ ID NO 80
<211> LENGTH: 7
<212> TYPE: DNA
<213> ORGANISM: Artificial Sequence
<220> FEATURE:
<223> OTHER INFORMATION: Oligonucleotide

<400> SEQUENCE: 80 rtaaaya                                                                     7

<210> SEQ ID NO 81
<211> LENGTH: 10
<212> TYPE: DNA
<213> ORGANISM: Artificial Sequence
<220> FEATURE:
<223> OTHER INFORMATION: Oligonucleotide

<400> SEQUENCE: 81 rttgcgyaay                                                                 10

<210> SEQ ID NO 82
<211> LENGTH: 14
<212> TYPE: DNA
<213> ORGANISM: Artificial Sequence
<220> FEATURE:
<223> OTHER INFORMATION: Oligonucleotide

<400> SEQUENCE: 82
gcttcccgaa cgtt                                                            14

<210> SEQ ID NO 83
<211> LENGTH: 20
<212> TYPE: DNA
<213> ORGANISM: Artificial Sequence
<220> FEATURE:
<223> OTHER INFORMATION: Oligonucleotide

<400> SEQUENCE: 83
gatgtccata ttaggacatc                                                      20

<210> SEQ ID NO 84
<211> LENGTH: 8
<212> TYPE: DNA
<213> ORGANISM: Artificial Sequence
<220> FEATURE:
<223> OTHER INFORMATION: Oligonucleotide

<400> SEQUENCE: 84 tttcccgc                                                                    8

<210> SEQ ID NO 85
<211> LENGTH: 6
<212> TYPE: DNA
<213> ORGANISM: Artificial Sequence
<220> FEATURE:
<223> OTHER INFORMATION: Oligonucleotide

<400> SEQUENCE: 85
``` cacgtg                                                            6

<210> SEQ ID NO 86
<211> LENGTH: 18
<212> TYPE: DNA
<213> ORGANISM: Artificial Sequence
<220> FEATURE:
<223> OTHER INFORMATION: Oligonucleotide

<400> SEQUENCE: 86
gccctacgtg ctgtctca                                               18

<210> SEQ ID NO 87
<211> LENGTH: 9
<212> TYPE: DNA
<213> ORGANISM: Artificial Sequence
<220> FEATURE:
<223> OTHER INFORMATION: Oligonucleotide

<400> SEQUENCE: 87 cgcccscgc                                                          9

<210> SEQ ID NO 88
<211> LENGTH: 11
<212> TYPE: DNA
<213> ORGANISM: Artificial Sequence
<220> FEATURE:
<223> OTHER INFORMATION: Oligonucleotide

<400> SEQUENCE: 88
gctcttccgg t                                                      11

<210> SEQ ID NO 89
<211> LENGTH: 6
<212> TYPE: DNA
<213> ORGANISM: Artificial Sequence
<220> FEATURE:
<223> OTHER INFORMATION: Oligonucleotide

<400> SEQUENCE: 89 cagctc                                                             6

<210> SEQ ID NO 90
<211> LENGTH: 17
<212> TYPE: DNA
<213> ORGANISM: Artificial Sequence
<220> FEATURE:
<223> OTHER INFORMATION: Oligonucleotide

<400> SEQUENCE: 90
ttcaaaggcg cctgttt                                                17

<210> SEQ ID NO 91
<211> LENGTH: 9
<212> TYPE: DNA
<213> ORGANISM: Artificial Sequence
<220> FEATURE:
<223> OTHER INFORMATION: Oligonucleotide

<400> SEQUENCE: 91 gcggggggcg                                                         9

<210> SEQ ID NO 92
<211> LENGTH: 17
<212> TYPE: DNA

```
<213> ORGANISM: Artificial Sequence
<220> FEATURE:
<223> OTHER INFORMATION: Oligonucleotide

<400> SEQUENCE: 92
tcctcctcct cctctcc                                                    17

<210> SEQ ID NO 93
<211> LENGTH: 12
<212> TYPE: DNA
<213> ORGANISM: Artificial Sequence
<220> FEATURE:
<223> OTHER INFORMATION: Oligonucleotide

<400> SEQUENCE: 93
cgtcacgstt sr                                                         12
```